US008524879B2

(12) United States Patent
Davidson et al.

(10) Patent No.: US 8,524,879 B2
(45) Date of Patent: Sep. 3, 2013

(54) RNA INTERFERENCE SUPPRESION OF NEURODEGENERATIVE DISEASES AND METHODS OF USE THEREOF

(75) Inventors: Beverly L. Davidson, North Liberty, IA (US); Haibin Xia, Iowa City, IA (US); Qinwen Mao, Iowa City, IA (US); Henry Paulson, Iowa City, IA (US); Ryan L. Boudreau, Iowa City, IA (US); Scott Harper, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 12/774,019

(22) Filed: May 5, 2010

(65) Prior Publication Data

US 2011/0111491 A1   May 12, 2011

Related U.S. Application Data

(63) Continuation of application No. 10/859,751, filed on Jun. 2, 2004, now abandoned, which is a continuation-in-part of application No. PCT/US03/16887, filed on May 26, 2003, which is a continuation-in-part of application No. 10/430,351, filed on May 5, 2003, now abandoned, which is a continuation of application No. 10/322,086, filed on Dec. 17, 2002, now abandoned, which is a continuation-in-part of application No. 10/212,322, filed on Aug. 5, 2002, now abandoned.

(51) Int. Cl.
C07H 21/04 (2006.01)

(52) U.S. Cl.
USPC .............. 536/24.5; 536/24.31; 536/24.1

(58) Field of Classification Search
None
See application file for complete search history.

(56) References Cited

U.S. PATENT DOCUMENTS

| 4,683,202 | A | 7/1987 | Mullis |
| 4,873,192 | A | 10/1989 | Kunkel |
| 4,962,091 | A | 10/1990 | Eppstein et al. |
| 5,350,674 | A | 9/1994 | Boenisch et al. |
| 5,580,859 | A | 12/1996 | Felgner et al. |
| 5,585,362 | A | 12/1996 | Wilson et al. |
| 5,686,288 | A | 11/1997 | MacDonald et al. |
| 5,814,500 | A | 9/1998 | Dietz |
| 5,837,449 | A | 11/1998 | Monia et al. |
| 5,849,995 | A | 12/1998 | Hayden et al. |
| 5,902,880 | A | 5/1999 | Thompson |
| 5,922,602 | A | 7/1999 | Kumagai et al. |
| 5,928,906 | A | 7/1999 | Koster et al. |
| 5,972,704 | A | 10/1999 | Draper et al. |
| 6,001,990 | A | 12/1999 | Wands et al. |
| 6,177,246 | B1 | 1/2001 | Monia et al. |
| 6,387,616 | B1 | 5/2002 | Ozelius et al. |
| 6,420,345 | B1 | 7/2002 | Patel et al. |
| 6,468,524 | B1 | 10/2002 | Chiorini et al. |
| 6,479,291 | B2 | 11/2002 | Kumagai et al. |
| 6,506,559 | B1 | 1/2003 | Driver et al. |
| 6,531,647 | B1 | 3/2003 | Baulcombe et al. |
| 6,573,099 | B2 | 6/2003 | Graham |
| 6,596,535 | B1 | 7/2003 | Carter |
| 6,794,414 | B1 | 9/2004 | Steinman |
| 6,852,535 | B1 | 2/2005 | Thompson |
| 7,186,552 | B2 | 3/2007 | Wilson et al. |
| 7,902,352 | B2 | 3/2011 | Kaemmerer et al. |
| 2002/0086356 | A1 | 7/2002 | Tuschl et al. |
| 2002/0132788 | A1 | 9/2002 | Lewis et al. |
| 2002/0173478 | A1 | 11/2002 | Gewirtz |
| 2003/0051263 | A1 | 3/2003 | Fire et al. |
| 2003/0055020 | A1 | 3/2003 | Fire et al. |
| 2003/0056235 | A1 | 3/2003 | Fire et al. |
| 2003/0108923 | A1 | 6/2003 | Tuschl et al. |
| 2003/0143732 | A1 | 7/2003 | Fosnaugh et al. |
| 2003/0148519 | A1 | 8/2003 | Engelke et al. |
| 2003/0165853 | A1 | 9/2003 | Partridge et al. |
| 2004/0023390 | A1 | 2/2004 | Davidson et al. |
| 2004/0053875 | A1 | 3/2004 | Kreutzer et al. |
| 2004/0096843 | A1 | 5/2004 | Rossi et al. |
| 2004/0192629 | A1 | 9/2004 | Xu et al. |
| 2004/0241854 | A1 | 12/2004 | Davidson et al. |
| 2005/0042646 | A1 | 2/2005 | Davidson et al. |
| 2005/0074887 | A1 | 4/2005 | Rossi et al. |
| 2005/0096284 | A1* | 5/2005 | McSwiggen .................... 514/44 |
| 2005/0106731 | A1 | 5/2005 | Davidson et al. |
| 2005/0186586 | A1 | 8/2005 | Zamore et al. |
| 2005/0196862 | A1 | 9/2005 | Wooddell et al. |
| 2005/0197315 | A1 | 9/2005 | Taira et al. |
| 2005/0255086 | A1 | 11/2005 | Davidson et al. |
| 2006/0009408 | A1 | 1/2006 | Davidson et al. |
| 2006/0257912 | A1 | 11/2006 | Kaemmerer et al. |
| 2010/0008981 | A1 | 1/2010 | Kaemmerer et al. |
| 2010/0325746 | A9 | 12/2010 | Kaemmerer et al. |

FOREIGN PATENT DOCUMENTS

| DE | 10100586 | 4/2002 |
| DE | 10100588 | 7/2002 |
| EP | 1 144 623 | 10/2001 |
| EP | 1 214 945 | 6/2002 |

(Continued)

OTHER PUBLICATIONS

Abdallah et al., *Biology of the Cell*, 1995, 85(1):1-7.
Abdelgany et al., *Hum. Mol Genet.*, 2003, 12:2637-2644.
Adelman et al., *DNA*, 1983, 2:183.
Agrawal, *TIBTech*, 1996, 14:376-387.
Alisky et al., *Hum Gen Ther.*, 2000, 11:2315.
Alisky et al., *NeuroReport*, 2000, 11:2669.
Alisky et al., *Am J Pharmacogenomics*, 4(1):45-51 (2004).
Altschul et al., *JMB*, 1990, 215:403.
Altschul et al., *Nucleic Acids Res.* 1997, 25:3389.
Ambrose et al, *Somat Cell Mol Genet.*, 1994, 20:27-38.
Ancellin et al., *The Journal of Biological Chemistry*, 2002, 277:6667-6675.

(Continued)

*Primary Examiner* — Kimberly Chong
(74) *Attorney, Agent, or Firm* — Viksnins Harris & Padys PLLP

(57) ABSTRACT

The present invention is directed to small interfering RNA molecules (siRNA) targeted against nucleic acid sequence that encodes huntingtin or ataxin-1, and methods of using these siRNA molecules.

25 Claims, 34 Drawing Sheets

(56) References Cited

FOREIGN PATENT DOCUMENTS

| | | |
|---|---|---|
| WO | WO 90/14090 | 11/1990 |
| WO | WO 94/01550 | 1/1994 |
| WO | WO 94/07529 | 4/1994 |
| WO | WO 99/32619 | 7/1999 |
| WO | WO 99/49029 | 9/1999 |
| WO | WO 00/44895 | 8/2000 |
| WO | WO 01/29058 | 4/2001 |
| WO | WO 01/49844 | 7/2001 |
| WO | WO 01/70949 | 9/2001 |
| WO | WO 01/75164 | 10/2001 |
| WO | WO 02/44321 | 6/2002 |
| WO | WO 02/55692 | 7/2002 |
| WO | WO 02/55693 | 7/2002 |
| WO | WO 03/006477 | 1/2003 |
| WO | WO 03/008573 | 1/2003 |
| WO | WO 03/010180 | 2/2003 |
| WO | WO 03/022052 | 3/2003 |
| WO | WO 03/023015 | 3/2003 |
| WO | WO 03/048362 | 6/2003 |
| WO | WO 03/080807 | 10/2003 |
| WO | WO 2004/013280 | 2/2004 |
| WO | WO 2004/013355 | 2/2004 |
| WO | WO 2004/042027 | 5/2004 |
| WO | WO 2004/047872 | 6/2004 |
| WO | WO 2004/058940 | 7/2004 |
| WO | WO 2005/105995 | 11/2005 |
| WO | WO 2006/031267 | 3/2006 |
| WO | WO 2006/083800 | 8/2006 |

OTHER PUBLICATIONS

Anderson et al., *Gene Ther.*, 2000, 7(12):1034-1038.
Anderson, "Human Gene Therapy," *Nature*, 1998, 392:25-30.
Andreason and Evans, *Biotechniques*, 1988, 6:650.
Augood et al., *Ann. Neurol.*, 1999, 46:761-769.
Augood et al., *Neurology*, 2002, 59:445-448.
Bass, "The Short Answer," *Nature*, 2001, 411:428-429.
Bates et al., *Curr Opin Neurol.*, 2003, 16:465-470.
Batzer et al., *Nucl. Acids Res.*, 1991, 19:508.
Baulcombe, *Plant Mol. Biol.*, 1996, 32:79-88.
Behr et al., *PNAS*, 1989, 86:6982.
Bernstein et al., *Nature*, 2001, 409:363-366.
Bertrand et al., *RNA*, 1997 3(1):75-88.
Bledsoe et al., *NatBiot*, 2000, 18:964.
Boado et al., *J Pharmacol Exp Ther*. 2000, 295(1):239-243.
Boden et al., "Enhanced gene silencing of HIV-1 specific siRNA using microRNA designed hairpins", *Nucleic Acids Research*, vol. 32, No. 3, pp. 115-1158, 2004.
Branch, *TIBS*, 1998, 23:45-50.
Brantl, *Biochimica et Biophyscia Acta*, 2002, 1575:15-25.
Brash et al., *Molec. Cell. Biol.*, 1987, 7:2031.
Breakefield et al., *Neuron*, 2001, 31:9-12.
Bridge et al., *Nat Genet.*, 2003, 34:263-264.
Brooks et al., *PNAS*, 2002, 99:6216-6221.
Brummelkamp et al., "A system for stable expression of short interfering RNAs in mammalian cells", *Science*, vol. 296, pp. 550-553, 2002.
Brummelkamp et al., *Cancer Cell*, 2002, 2:243-247.
Burright et al., *Cell*, 1995, 82:937-948.
Capecchi, *Cell*, 1980, 22:479.
Caplen et al., *PNAS*, 2001, 98:9742-9747.
Caplen et al., *Hum. Mol. Genet.*, 2002, 11(2):175-184.
Carter et al., *J Neurosci.*, 1999, 19(8):3248-3257.
Cemal et al., *Hum. Mol. Genet.*, 2002, 11(9):1075-1094.
Chai et al., *Hum. Mol. Genet.*, 1999, 8:673-683.
Chai et al., *J. Neurosci.*, 1999, 19:10338-10347.
Chan et al., *Hum Mol Genet.*, 2000, 9(19):2811-2820.
Check, *Nature*, 2002, 417:779.
Check, *Nature*, 2004, 432, 136.
Chen et al., *Cell*, 2003, 113(4):457-468.
Chiu and Rana, *Mol. Cell.*, 2002, 10(3):549-561.
Clemens et al., *PNAS*, 2000, 97:6499-6503.
Cogoni et al., *Antonie Van Leeuwenhoek*, 1994, 65:205-209.
Corpet et al., *Nucl. Acids Res.*, 1988, 16:10881.
Cortez et al., *Science*, 2001, 294:1713-1716.
Couzin, *Science*, 2004, 306, 1124-1125.
Crea et al., *PNAS*, 1978, 75:5765.
Cullen, *Nat. Immunol.*, 2002, 3:597-599.
Czauderna et al., "Inducible shRNA expression for application in a prostate cancer mouse model", *Nucleic Acids Research*, vol. 31, No. 21, e127, Oxford University Press, 2003.
Czauderna et al., "Structural variations and stabilizing modifications of synthetic siRNAs in mammalian cells", Nucleic Acids Res, 31(11), pp. 2705-2716, 2003.
Dale et al., A test of the model to predict unusually stable RNA hairpin loop stability, *RNA*, 6, pp. 608-615, 2000.
Davidson et al., *Nat Rev.*, 2003, 4(5):353-364.
Davidson et al., *The Lancet Neurol.*, 2004, 3:145-149.
Davidson et al., *PNAS*, 2000, 97:3428-3432.
Davidson et al., *Meth Enzymol*, 392:145-173, (2005).
Deng et al. *J Org. Chem.*, 1999, 64:202-208.
Dillin, *PNAS*, 2003, 100:6289-6291.
Ding et al., *Aging Cell.*, 2003, 2:209-217.
Doench et al., *Genes Dev.*, 2003, 17(4):438-442.
Doheny et al., *Neurology*, 2002, 59:1244-1246.
Donze et al., *Nucleic Acids Research*, 2002, 30(10):1-4.
Elbashir et al., *Nature*, 2001, 411:494-498.
Elbashir et al., Genes and Development, 2001, 15:188-200.
Elbashir et al., *Embo J.*, 2001, 20(23):6877-6888.
Emamian et al., *Neuron*, 2003, 38:375-87.
Fahn et al., *Adv. Neurol.*, 1998, 78:1-10.
Felgner et al., *PNAS.*, 1987, 84:7413.
Feng et al., *Virology*, 2000 25;276(2):271-278.
Fernandez-Funez et al., *Nature*, 2000, 408:101-106.
Fire et al., *Nature*, 1998, 391:806-811.
Fujigasaki et al., "CAG repeat expansion in the Tata box-bidning protein gene causes autosomal dominant cerebellar ataxia", *Brain*, 124, pp. 1939-1947, 2001.
Garrus et al., *Cell*, 2001, 107:55-65.
Gaspar et al., *Am. J. Hum. Genet.*, 2001, 68(2):523-528.
Gitlin et al., *Nature*, 2002, 418:430-434.
Goeddel et al., *Nucleic Acids Res.*, 1980, 8:4057.
Gonzalez-Alegre et al., *Ann Neurol.*, 2003, 53:781-787.
Gonzalez-Alegre et al., *J Neurosci.*, 2005; 25(45):10502-9.
Goodchild et al., *Mov. Disord.*, 2002, 17(5):958, Abstract.
Goto et al., "Suppression of Huntingtin Gene Expression by siRNA: A Possible Therapeutic Tool for Huntington's Disease", *Neurology*, 60(5), Suppl 1, p. A286, Abstract P04.055, 2003.
Grishok et al., *Science*, 2000, 287:2494-2497.
Hamilton and Baulcombe, *Science*, 1999, 286:950-952.
Hammond et al., *Nat Rev Genet*. 2001;2(2):110-119.
Hammond et al., *Nature*, 2000, 404:293-296.
Hannon, *Nature*, 2002, 418:244-251.
Hague et al., *Exp Neurol.* 1997; 144; 139-46.
Harborth et al., *Journal of Cell Science*, 2001, 114:4557-4565.
Hardy et al., *Science*, 2002, 297(5580):353-356.
Harper et al., *Meth Mol Biol*, 309:219-236 (2005).
Harper et al., *PNAS*, 102(16):5820-5825, (2005).
Hasholt et al., *J Gene Med.* 2003;5(6):528-38.
Hewett et al., *Hum. Mol. Gen.*, 2000, 9:1403-1413.
Higgins et al., *CABIOS*, 1989, 5:151.
Higgins et al., *Gene*, 1988, 73:237.
Hilberg et al., *PNAS*, 1987, 84:5232.
Holen et al., "Positional effects of short interfering RNAs targeting the human coagulation trigger Tissue Factor", *Nucleic Acids Res*, 30(8), pp. 1757-6617, 2002.
Holland et al., *PNAS*, 1987, 84:8662.
Hornykiewicz et al., *N. Engl. J. Med.*, 1986, 315:347-353.
Houlden et al., *Neurology*, 2001, 56(12):1702-1706.
Huang et al., *CABIOS*, 1992, 8:155.
Hutton et al., *Nature*, 1998, 393:702-705.
Jacque et al., *Nature*, 2002, 418(6896):435-438.
Johnston, *Nature*, 1990, 346:776.
Kao et al., *J. Biol. Chem.*, 2004, 279:1942-1949.
Karlin and Altschul, *PNAS*, 1990, 87:2264.
Karlin and Altschul, *PNAS*, 1993, 90:5873.

Kato et al., *J Biol Chem.*, 2001, 76(24):21809-21820.
Kawasaki et al., *Nucleic Acids Res.*, 2003, 31(2):700-707.
Kennerdell et al., *Cell*:95, 1017-1026 (1998).
Kennerdell et al., *Nat Biotechnol.* 2000;18(8):896-898.
Ketting et al., *Nature*, 2000, 404:296-298.
Khvorova et al., 2003, *Cell*, 115:505.
Kisielow et al., *Biochem. J.*, 2002, 363:1-5.
Kitabwalla and Ruprecht, *N. Engl. J. Med.*, 2002, 347:1364-1367.
Klein et al., *Ann. Neurol.*, 2002, 52:675-679.
Klein et al., *Curr. Opin. Neurol.*, 2002, 4:491-497.
Konakova et al., *Arch. Neurol.*, 2001, 58:921-927.
Koseki et al., *J. Virol.*, 1999, 73:1868-1877.
Krichevsky and Kosik, *PNAS*, 2002, 99(18):11926-11929.
Kunath et al., *Nat Biotechnol*, 2003, 21:559-561.
Kunkel et al., *Meth. Enzymol.*, 1987, 154:367.
Kunkel, *PNAS*, 1985, 82:488.
Kustedjo et al., *J. Biol. Chem.*, 2000, 275:27933-27939.
Laccone et al., *Hum. Mutat.*, 1999, 13(6):497-502.
Lai et al., *PNAS*, 1989, 86:10006.
Larrick and Burck, "Gene Therapy," *Application of Molecular Biology*, 1999, Elsevier Science Publishing Co., Inc., New York, p. 71-104.
Lawn et al., *Nucleic Acids Res.*, 1981, 9:6103.
Lee et al., *Nature Biotechnology*, 2002, 19:500-505.
Lee et al., *Annu Rev Neurosci.*, 2001, 24:1121-1159.
Lee et al., *Cell*, 2004, 117:69-81.
Leger et al., *J. Cell. Sci.*, 1994, 107:3403-3412.
Leung et al., *Neurogenetics*, 2001, 3:133-143.
Lewis et al., *Science*, 2001, 293(5534):1487-1491.
Lin et al., *Hum. Mol. Genet.*, 2001, 10(2):137-144.
Liu et al., "Specific inhibition of Huntington's disease gene expression by siRNAs in cultured cells", *Proc Japan Acad.*, 79, Ser. B, pp. 293-298, 2003.
Loeffler et al., *J. Neurochem.*, 1990, 54:1812.
Lotery et al., *Hum Gene Ther.*, 2002, 13:689-696.
Manche et al., *Mol. Cell Biol.*, 1992, 12:5238.
Margolis and Ross, *Trends Mol. Med.*, 2001, 7:479-482.
Martinez et al., *Cell*, 2002, 110(5):563-574.
Martinez et al., *PNAS*, 2002, 99:14849-14854.
McCaffrey et al., *Nature*, 2002, 418(6893):38-39.
McManus et al., *Nature Reviews Genetics*, 2002, 3(10):737-747.
McManus et al., *RNA*, 8, pp. 842-850, 2002.
Meinkoth and Wahl, *Anal. Biochem.*, 1984, 138:267.
Mercola et al., *Cancer Gene Therapy*, 1995, 2:47-59.
Miller et al., *Nucleic Acids Research*, 32(2), pp. 661-668, 2004.
Miller et al., *PNAS*, 2003, 100:7195-7200.
Miller, et al., *Mol. Cell. Biol.*, 1990, 10:4239.
Minks et al., *J. Biol. Chem.*, 1979, 254:10180.
Miyagishi et al., "Strategies for generation of an siRNA expression library directed against the human genome", *Oligonucleotides*, vol. 13, pp. 325-333, 2003.
Miyagishi et al., *Nature Biotechnology*, 2002, 19:497-499.
Molling, *J Mol Med.*, 1997, 75(4):242-246.
Moulder et al., *J. Neurosci.*, 1999, 19:705-715.
Mullan et al., *Nature Genetics*, 1992, 1:345-347.
Myers and Miller, *CABIOS*, 1988, 4:11.
Nasir et al., *Cell*, 1995, 81:811-823.
Needleman and Wunsch, *JMB*, 1970, 48:443.
Nellemann et al., *Mol Cell Neurosci.* 2000;16(4):313-323.
Nykanen et al., *Cell*, 2001, 107:309-321.
Oddo et al., *Neuron*, 2003, 39(3):409-421.
Ogura and Wilkinson, *Genes Cells*, 2001, 6:575-597.
Ohtsuka et al., *JBC*, 1985, 260:2605.
Okabe et al., *FEBS Lett.*, 1997, 407:313-319.
Ooboshi et al., *Arterioscler. Thromb. Vasc. Biol.*, 1997, 17:1786-1792.
Ozelius et al., *Genomics*, 1999, 62:377-384.
Ozelius et al., *Nature Genetics*, 1997, 17:40-48.
Paddison et al., *Genes and Development*, 2002, 16:948-958.
Paddison et al., *PNAS*, 2002, 99:1443-1448.
Pardoll et al., *Immunity*, 1995, 3(2):165-169.
Paul et al., *Nature Biotechnology*, 2002, 29:505-508.
Paule et al., *Nucleic Acids Research*, 2000, 28:1283-1298.
Paulson et al., *Ann. Neurol.*, 1997, 41(4):453-462.
Pearson and Lipman, *PNAS*, 1988, 85:2444.
Pearson et al., *Meth. Mol. Biol.*, 1994, 24:307.
Pham et al., *Cell*, 2004, 117:83-94.
Pittman et al., *J. Neurosci.*, 1993, 13(9):3669-3680.
Poorkaj et al., *Ann. Neurol.*, 1998, 43:815-825.
Promega siRNA Designer, SiLentGene U6 Cassette RNA Interference Version 1.1, May 2003, www.promega.com/siRNADesigner/program/default.asp.
Quantin et al., *PNAS*, 1992, 89:2581.
Reynolds et al., *Nat. Biotechnol,.* 2004, 22:326-30.
Rosenfeld et al., *Science*, 1991, 252:431.
Rossolini et al., *Mol. Cell. Probes*, 1994, 8:91.
Rubinson et al., *Nature Genetics*, 2003, 33:401-406.
Scharfmann et al., *PNAS*, 1991, 88:4626.
Schilling et al., *Hum Mol Genet.*, 1999, 8(3):397-407.
Schilling et al., *Neurobiol Dis.*, 2001, 8:405-418.
Schramke et al., *Nature*, 2005, 435:1275-1279.
Schwarz et al., *Cell*, 2003, 115(2):199-208.
Schwarz et al., *Mol. Cell.*, 2002, 10(3):537-548.
Sharp, *Genes and Development*, 1999, 13:139-141.
Shi et al., *RNA*, 2000, 6:1069-1076.
Shipley et al., *J. Biol. Chem.*, 1993, 268:12193.
Sisodia et al., *Nat Rev.*, 2002, 3(4):281-290.
Sledz et al., *Nat Cell Biol.*, 2003, 5:834-839.
Smith et al., *Adv. Appl. Math.*, 1981, 2:482.
Song et al., *Nat. Med.*, 2003, 9:347-351.
Stein et al., *J. Virol.*, 1999, 73:3424-3429.
Stein et al., *RNA*, 2003, 9(2):187-192.
Sui et al., *PNAS*, 2002, 99:(8)5515-5520.
Svoboda et al., *Development*, 2000, 127:4147-4156.
Tabara et al., *Cell*, 1999, 99:123-132.
Tanemura et al., *J. Neurosci.*, 2002, 22(1):133-141.
Tang et al., *Genes Dev.*, 2003, 17(1):49-63.
Ternin, "Retrovirus vectors for gene transfer", *Gene Transfer*, Kucherlapati R, Ed., pp. 149-187, Plenum, 1986.
Tijsterman et al., *Cell*, 2004; 117(1):1-3.
Timmons et al., *Nature*, 1998, 395:854.
Tritz et al., "Screening Promoters for Optimal Expression of Ribozymes", 1999, pp. 115-123, in Intracellular Ribozyme Applications: Principles and Protocols, Horizon Scientific Press.
Trottier et al., *Nature*, 1995, 378(6555):403-406.
Turner et al., *Mol. Biotech.*, 1995, 3:225.
Tuschl, *Nat. Biotechnol.*, 2002, 20:446-448.
Valerio et al., *Gene*, 1989, 84:419.
Verma et al., *Nature*, 1997, 389:239-242.
Victor et al., *EMBO Reports*, 3(1), pp. 50-55,2002.
Viera et al., *Meth. Enzymol.*, 1987, 153:3.
Wagner et al., *Nature*, 1998, 391:744-745.
Walker et al., *Neurology*, 2002, 58:120-124.
Waterhouse et al., *PNAS*, 1998, 95:13959-13964.
Wianny et al., *Nat. Cell Biol.*, 2000, 2:70-75.
Xia et al., *Nat. Biotechnol.*, 2001, 19:640-644.
Xia et al., *Nat Med*, 10(8):775-776 (2004).
Xia et al., "RNAi suppresses polyglutamine-induced neurodegeneration in a model of spinocerebellar ataxia", *Nat Med*, 10(8), pp. 816-820, 2004.
Xia et al., "siRNA-mediated gene silencing in vitro and in vivo", *Nature Biotechnology*, vol. 20, pp. 1006-1010, 2002.
Xiao et al., *Journal of Virology*, 73(5), pp. 3994-4003, 1999.
Yamamoto et al., *Cell*, 2000, 101(1):57-66.
Yang et al., *Molecular and Cellular Biology*, 2001, 21:7807-7816.
Yu et al., *PNAS.*, 2002, 99:(9)6047-6052.
Yu et al., "Mutant Huntingtin causes contex-dependent neurodegenration in mice with Huntington's Disease", *Journal of Neuroscience*, vol. 23, pp. 2193-2202, 2003.
Zamore et al., *Cell*, 2000, 101:25-33.
Zeng et al., *PNAS*, 2003, 100(17):9779-9784.
Zeng et al., *RNA*, 2003, 9(1), 112-123.
Zoghbi and On, *Annu. Rev. Neurosci.*, 2000, 23:217-247.

* cited by examiner siGFP　siβgluc
Fig. 1F
Fig. 1G
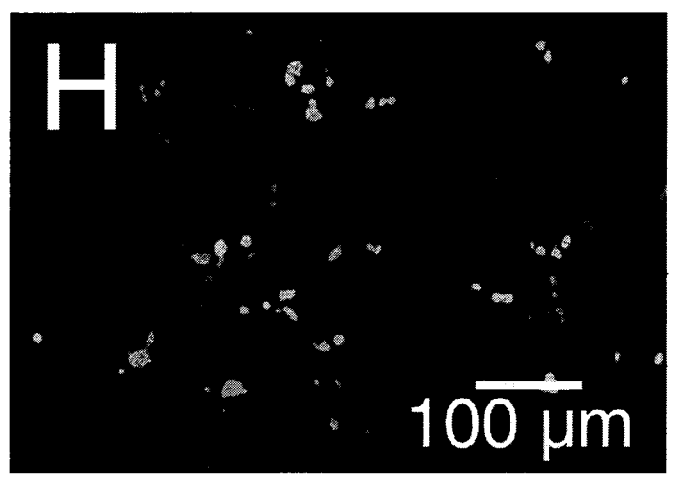
Fig. 1H

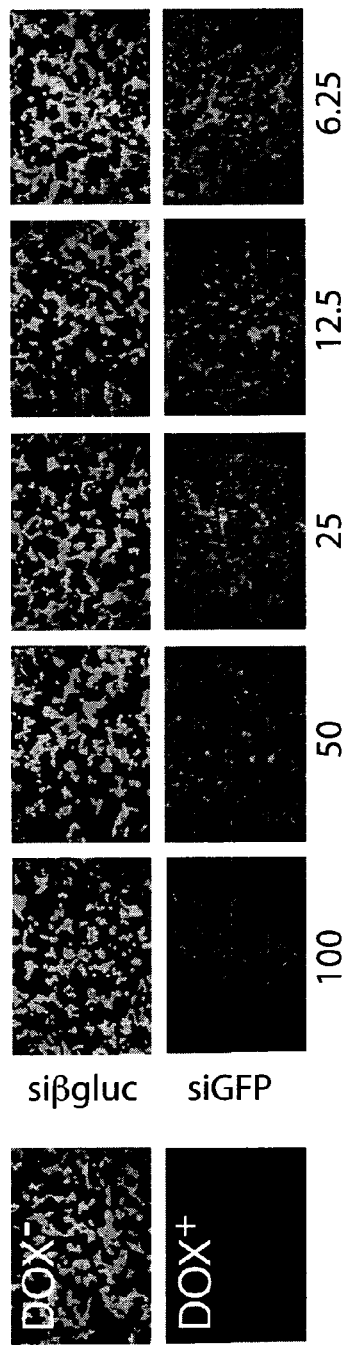
Fig. 3A
Fig. 3B
Fig. 3C

Ataxin-1

Tet-responsive H1 promoter

SEQUENCE LISTING

<160> NUMBER OF SEQ ID NOS: 17

<210> SEQ ID NO 1
<211> LENGTH: 40
<212> TYPE: DNA
<213> ORGANISM: Artificial Sequence
<220> FEATURE:
<223> OTHER INFORMATION: CMV primers

<400> SEQUENCE: 1
aaggtaccag atcttagtta ttaatagtaa tcaattacgg                    40

<210> SEQ ID NO 2
<211> LENGTH: 43
<212> TYPE: DNA
<213> ORGANISM: Artificial Sequence
<220> FEATURE:
<223> OTHER INFORMATION: CMV primers

<400> SEQUENCE: 2
gaatcgatgc atgcctcgag acggttcact aaaccagctc tgc                43

<210> SEQ ID NO 3
<211> LENGTH: 69
<212> TYPE: DNA
<213> ORGANISM: Artificial Sequence
<220> FEATURE:
<223> OTHER INFORMATION: Poly-A oligonucleotide primers

<400> SEQUENCE: 3
ctagaactag taataaagga tcctttattt tcattggatc cgtgtgttgg tttttttgtgt    60 gcggccgcg                                                             69

<210> SEQ ID NO 4
<211> LENGTH: 69
<212> TYPE: DNA
<213> ORGANISM: Artificial Sequence
<220> FEATURE:

<223> OTHER INFORMATION: Poly-A oligonucleotide primers

<400> SEQUENCE: 4
tcgacgcggc cgcacacaaa aaaccaacac acggatccaa tgaaaataaa ggatccttta    60
ttactagtt                                                           69

<210> SEQ ID NO 5
<211> LENGTH: 21
<212> TYPE: DNA
<213> ORGANISM: Artificial Sequence
<220> FEATURE:
<223> OTHER INFORMATION: Total RNA probes

<400> SEQUENCE: 5
cacaagctgg agtacaacta c                                             21

<210> SEQ ID NO 6
<211> LENGTH: 22
<212> TYPE: DNA
<213> ORGANISM: Artificial Sequence
<220> FEATURE:
<223> OTHER INFORMATION: Total RNA probes

<400> SEQUENCE: 6
gtacttgtac tccagctttg tg                                            22

<210> SEQ ID NO 7
<211> LENGTH: 21
<212> TYPE: DNA
<213> ORGANISM: Homo sapien

<400> SEQUENCE: 7
aagaaagaac tttcagctac c                                             21

<210> SEQ ID NO 8
<211> LENGTH: 19
<212> TYPE: DNA
<213> ORGANISM: Homo sapien

<400> SEQUENCE: 8
agaactttca gctaccaag                                                19

<210> SEQ ID NO 9
<211> LENGTH: 21
<212> TYPE: DNA
<213> ORGANISM: Homo sapien

<400> SEQUENCE: 9
aaagaacttt cagctaccaa g                                             21

<210> SEQ ID NO 10
<211> LENGTH: 19
<212> TYPE: DNA
<213> ORGANISM: Homo sapien

<400> SEQUENCE: 10
tgcctcaaca aagttatca                                                19

<210> SEQ ID NO 11
<211> LENGTH: 21
<212> TYPE: DNA
<213> ORGANISM: Homo sapien

<400> SEQUENCE: 11

-continued

```
aatgcctcaa caaagttatc a                                              21

<210> SEQ ID NO 12
<211> LENGTH: 21
<212> TYPE: DNA
<213> ORGANISM: Homo sapien

<400> SEQUENCE: 12
gaggaagagg aggaggccga c                                              21

<210> SEQ ID NO 13
<211> LENGTH: 21
<212> TYPE: DNA
<213> ORGANISM: Homo sapien

<400> SEQUENCE: 13
ggacacaagg ctgagcagca g                                              21

<210> SEQ ID NO 14
<211> LENGTH: 51
<212> TYPE: DNA
<213> ORGANISM: Homo sapien

<400> SEQUENCE: 14
cagcagcacc tcagcagggc tgcaggatta gtcaaccacc tcagcagggc t             51

<210> SEQ ID NO 15
<211> LENGTH: 6
<212> TYPE: DNA
<213> ORGANISM: Homo sapien

<400> SEQUENCE: 15 actagt                                                               6

<210> SEQ ID NO 16
<211> LENGTH: 10
<212> TYPE: DNA
<213> ORGANISM: Homo sapien

<400> SEQUENCE: 16
cttcctgtca                                                           10

<210> SEQ ID NO 17
<211> LENGTH: 21
<212> TYPE: DNA
<213> ORGANISM: Homo sapien

<400> SEQUENCE: 17
aagaggagga ggccgacgcc c                                              21
```

RNA INTERFERENCE SUPPRESION OF NEURODEGENERATIVE DISEASES AND METHODS OF USE THEREOF

CLAIM OF PRIORITY

This application is a continuation of U.S. application Ser. No. 10/859,751, filed on Jun. 2, 2004, which is a continuation-in-part of International Application No. PCT/US2003/016887, filed on May 26, 2003, which is a continuation-in-part of U.S. application Ser. No. 10/430,351 filed on May 5, 2003, which is a continuation of U.S. application Ser. No. 10/322,086 filed on Dec. 17, 2002, which is a continuation-in-part application of U.S. application Ser. No. 10/212,322, filed Aug. 5, 2002. All of these applications are incorporated by reference herein.

STATEMENT REGARDING FEDERALLY SPONSORED RESEARCH OR DEVELOPMENT

This invention was made with government support from the National Institutes of Health (NS044494, NS38712, HD44093, DK54759, and NX22920). The Government has certain rights in this invention.

BACKGROUND OF THE INVENTION

Double-stranded RNA (dsRNA) can induce sequence-specific posttranscriptional gene silencing in many organisms by a process known as RNA interference (RNAi). However, in mammalian cells, dsRNA that is 30 base pairs or longer can induce sequence-nonspecific responses that trigger a shutdown of protein synthesis. RNA fragments are the sequence-specific mediators of RNAi. Interference of gene expression by these small interfering RNA (siRNA) is now recognized as a naturally occurring strategy for silencing genes in *C. elegans, Drosophila*, plants, and in mouse embryonic stem cells, oocytes and early embryos.

SUMMARY OF THE INVENTION

The dominant polyglutamine expansion diseases, which include Spinocerebellar ataxia type 1 (SCA1) and Huntington's disease (HD), are progressive, untreatable neurodegenerative disorders. In inducible mouse models of SCA1 and HD, repression of mutant allele expression improves disease phenotypes. Thus, therapies designed to inhibit disease gene expression would be beneficial. In this study, the ability of RNA interference (RNAi) to inhibit polyglutamine-induced neurodegeneration caused by mutant ataxin-1 was evaluated in a mouse model of SCA1. Upon intracerebellar injection, recombinant AAV vectors expressing shRNAs profoundly improved motor coordination, restored cerebellar morphology, and resolved characteristic ataxin-1 inclusions in Purkinje cells of SCA1 mice. The present invention provides methods of using RNAi in vivo to treat dominant neurodegenerative diseases. "Treating" as used herein refers to ameliorating at least one symptom of, curing and/or preventing the development of a disease or a condition.

In certain embodiment of the invention, siRNAs are employed to inhibit expression of a target gene. By "inhibit expression" is meant to reduce, diminish or suppress expression of a target gene. Expression of a target gene may be inhibited via "gene silencing." Gene silencing refers to the suppression of gene expression, e.g., transgene, heterologous gene and/or endogenous gene expression, which may be mediated through processes that affect transcription and/or through processes that affect post-transcriptional mechanisms. In some embodiments, gene silencing occurs when siRNA initiates the degradation of the mRNA transcribed from a gene of interest in a sequence-specific manner via RNA interference, thereby preventing translation of the gene's product (for a review, see Brantl, 2002).

The present invention provides an isolated RNA duplex that has a first strand of RNA and a second strand of RNA, wherein the first strand has at least 15 contiguous nucleotides encoded by shSCA1.F10 (SEQ ID NO:13) or shSCA1.F11 (SEQ ID NO:14), and wherein the second strand is complementary to at least 12 contiguous nucleotides of the first strand. In one embodiment, the first strand of RNA is encoded by shSCA1.F10 or by shSCA1.F11. As used herein the term "encoded by" is used in a broad sense, similar to the term "comprising" in patent terminology. For example, the statement "the first strand of RNA is encoded by SEQ ID NO:13" means that the first strand of RNA sequence corresponds to the RNA sequence transcribed from the DNA sequence indicated in SEQ ID NO:13, but may also contain additional nucleotides at either the 3' end or at the 5' end of the RNA molecule.

The present invention also provides an RNA duplex (under physiological conditions) having a first strand of RNA and a second strand of RNA, wherein the first strand has at least 15 contiguous nucleotides encoded by (a) shHDEx2.1 (5'-AA-GAAAGAACTTTCAGCTACC-3', SEQ ID NO:7)), (b) shHDEx2.2 19 nt (5'-AGAACTTTCAGCTACCAAG-3' (SEQ ID NO:8)), (c) shHDEx2.2 21 nt (5'-AAAGAACTTTCAGC-TACCAAG-3' (SEQ ID NO:9)), (d) shHDEx3.1 19 nt (5'-TGCCTCAACAAAGTTATCA-3' (SEQ ID NO:10)), or (e) shHDEx3.1 21 nt (5'-AATGCCTCAACAAAGTTATCA-3' (SEQ ID NO:11)), (f) siEX58#1 (5'-GAGGAAGAGGAG-GAGGCCGAC-3' (SEQ ID NO:12)), or (g) siEX58#2 (5'-AAGAGGAGGAGGCCGACGCCC-3' (SEQ ID NO:17)) and wherein the second strand is complementary to at least 12 contiguous nucleotides of the first strand.

In certain embodiments, the RNA duplex described above is between 15 and 30 base pairs in length, such as 19 or 21 base pairs in length. In certain embodiments, the first and/or second strand further comprises an overhang, such as a 3' overhang region, a 5' overhang region, or both 3' and 5' overhang regions. The two strands of RNA in the siRNA may be completely complementary, or one or the other of the strands may have an "overhang region" (i.e., a portion of the RNA that does not bind with the second strand). Such an overhang region may be from 1 to 10 nucleotides in length.

In certain embodiments, in the RNA duplex described above may, the first strand and the second strand are operably linked by means of an RNA loop strand to form a hairpin structure to form a duplex structure and a loop structure. In certain embodiments, the loop structure contains from 4 to 10 nucleotides, such as 4, 5 or 6 nucleotides.

The present invention further provides expression cassettes containing a nucleic acid encoding at least one strand of the RNA duplex described above. The expression cassette may further contain a promoter, such as a regulatable promoter or a constitutive promoter. Examples of suitable promoters include a CMV, RSV, pol II or pol III promoter. The expression cassette may further contain a polyadenylation signal (such as a synthetic minimal polyadenylation signal) and/or a marker gene.

The present invention also provides vectors containing the expression cassettes described above. Examples of appropriate vectors include adenoviral, lentiviral, adeno-associated viral (AAV), poliovirus, HSV, or murine Maloney-based viral vectors. In one embodiment, the vector is an adenoviral vector. In certain embodiments, a vector may contain two expression cassettes, a first expression cassette containing a nucleic acid encoding the first strand of the RNA duplex and a second expression cassette containing a nucleic acid encoding the second strand of the RNA duplex.

The present invention provides cells (such as a mammalian cell) containing the expression cassette or vectors described above. The present invention also provides a non-human mammal containing the expression cassette or vectors described above.

The present invention provides a method of suppressing the accumulation of huntingtin or ataxin-1 in a cell by introducing a ribonucleic acid (RNA) described above into the cell in an amount sufficient to suppress accumulation of huntingtin or ataxin-1 in the cell. In certain embodiments, the accumulation of huntingtin or ataxin-1 is suppressed by at least 10%. The accumulation of huntingtin or ataxin-1 is suppressed by at least 10%, 20%, 30%, 40%, 50%, 60%, 70% 80%, 90% 95%, or 99%.

The present invention provides a method of preventing cytotoxic effects of mutant huntingtin or ataxin-1 in a cell by introducing a ribonucleic acid (RNA) described above into the cell in an amount sufficient to suppress accumulation of huntingtin or ataxin-1, and wherein the RNA prevents cytotoxic effects of huntingtin or ataxin-1 in the ocular tissue cell.

The present invention provides a method to inhibit expression of a huntingtin or ataxin-1 gene in a cell by introducing a ribonucleic acid (RNA) described above into the cell in an amount sufficient to inhibit expression of the huntingtin or ataxin-1, and wherein the RNA inhibits expression of the huntingtin or ataxin-1 gene. The huntingtin or ataxin-1 is inhibited by at least 10%, 20%, 30%, 40%, 50%, 60%, 70% 80%, 90% 95%, or 99%.

The present invention provides a method to inhibit expression of a huntingtin or ataxin-1 gene in a mammal (e.g., a human) by (a) providing a mammal containing a neuronal cell, wherein the neuronal cell contains the huntingtin or ataxin-1 gene and the neuronal cell is susceptible to RNA interference, and the huntingtin or ataxin-1 gene is expressed in the neuronal cell; and (b) contacting the mammal with a ribonucleic acid (RNA) or a vector described above, thereby inhibiting expression of the huntingtin or ataxin-1 gene. In certain embodiments, the accumulation of huntingtin or ataxin-1 is suppressed by at least 10%. The huntingtin or ataxin-1 is inhibited by at least 10%, 20%, 30%, 40%, 50%, 60%, 70% 80%, 90% 95%, or 99%. In certain embodiments, the cell located in vivo in a mammal.

The present invention provides a viral vector comprising a promoter and a micro RNA (miRNA) shuttle containing an embedded siRNA specific for a target sequence. In certain embodiments, the promoter is an inducible promoter. In certain embodiments, the vector is an adenoviral, lentiviral, adeno-associated viral (AAV), poliovirus, HSV, or murine Maloney-based viral vector. In certain embodiments, the targeted sequence is a sequence associated with a condition amenable to siRNA therapy, such as a neurodegenerative disease. An example of neurodegenerative diseases is a trinucleotide-repeat disease, such as a disease associated with polyglutamine repeats. These diseases include Huntington's disease or a spinocerebellar ataxia (SCA). Examples of SCA diseases are SCA1, SCA2, SCA3, SCA6, SCA7, or SCA17. The target sequence of the present invention, in certain embodiments, is a sequence encoding ataxin-1 or huntingtin.

The present invention provides a method of preventing cytotoxic effects of neurodegenerative disease in a mammal in need thereof, by introducing the vector encoding a miRNA described in the preceding paragraph into a cell in an amount sufficient to suppress accumulation of a protein associated with the neurodegenerative disease, and wherein the RNA prevents cytotoxic effects of neurodegenerative disease.

The present invention also provides a method to inhibit expression of a protein associated with the neurodegenerative disease in a mammal in need thereof, by introducing the vector encoding a miRNA described above into a cell in an amount sufficient to inhibit expression of the protein associated with the neurodegenerative disease, wherein the RNA inhibits expression of the protein associated with the neurodegenerative disease. The huntingtin or ataxin-1 is inhibited by at least 10%, 20%, 30%, 40%, 50%, 60%, 70% 80%, 90% 95%, or 99%.

The present invention provides a method to inhibit expression of huntingtin or ataxin-1 in a mammal in need thereof by (a) providing a mammal containing a neuronal cell, wherein the neuronal cell contains the huntingtin or ataxin-1 gene and the neuronal cell is susceptible to RNA interference, and the huntingtin or ataxin-1 gene is expressed in the neuronal cell; and (b) contacting the mammal the vector encoding a miRNA described above, thereby inhibiting expression of the huntingtin or ataxin-1 gene. The huntingtin or ataxin-1 is inhibited by at least 10%, 20%, 30%, 40%, 50%, 60%, 70% 80%, 90% 95%, or 99%.

BRIEF DESCRIPTION OF THE FIGURES

This patent or application file contains at least one drawing executed in color. Copies of this patent or patent application publication with color drawing(s) will be provided by the Office upon request and payment of the necessary fee.

FIG. 1A-J. siRNA expressed from CMV promoter constructs and in vitro effects. (A) A cartoon of the expression plasmid used for expression of functional siRNA in cells. The CMV promoter was modified to allow close juxtaposition of the hairpin to the transcription initiation site, and a minimal polyadenylation signal containing cassette was constructed immediately 3' of the MCS (mCMV, modified CMV; mpA, minipA). (B, C) Fluorescence photomicrographs of HEK293 cells 72 h after transfection of pEGFPN1 and pCMVβgal (control), or pEGFPN1 and pmCMVsiGFPmpA, respectively. (D) Northern blot evaluation of transcripts harvested from pmCMVsiGFPmpA (lanes 3, 4) and pmCMVsiβ-galmpA (lane 2) transfected HEK293 cells. Blots were probed with $^{32}$P-labeled sense oligonucleotides. Antisense probes yielded similar results (not shown). Lane 1, $^{32}$P-labeled RNA markers. AdsiGFP infected cells also possessed appropriately sized transcripts (not shown). (E) Northern blot for evaluation of target mRNA reduction by siRNA (upper panel). The internal control GAPDH is shown in the lower panel. HEK293 cells were transfected with pEGFPN1 and pmCMVsiGFPmpA, expressing siGFP, or plasmids expressing the control siRNA as indicated. pCMVeGFPx, which expresses siGFPx, contains a large poly(A) cassette from SV40 large T and an unmodified CMV promoter, in contrast to pmCMVsiGFPmpA shown in (A). (F) Western blot with anti-GFP antibodies of cell lysates harvested 72 h after transfection with pEGFPN1 and pCMVsiGFPmpA, or pEGFPN1 and pmCMVsiβglucmpA. (G, H) Fluorescence photomicrographs of HEK293 cells 72 h after transfection of pEGFPN1 and pCMVsiGFPx, or pEGFPN1 and pmCMVsiβglucmpA, respectively. (I, J) siRNA reduces expression from endogenous alleles. Recombinant adenoviruses were generated from pmCMVsiβglucmpA and pmCMVsiGFPmpA and purified. HeLa cells were infected with 25 infectious viruses/cell (MOI=25) or mock-infected (control) and cell lysates harvested 72 h later. (I) Northern blot for β-glucuronidase mRNA levels in Adsiβgluc and AdsiGFP transduced cells. GAPDH was used as an internal control for loading. (J) The concentration of β-glucuronidase activity in lysates quantified by a fluorometric assay. (Stein 1999).

FIG. 3A-D. siGFP gene transfer reduces Q19-eGFP expression in cell lines. PC12 cells expressing the polyglutamine repeat Q19 fused to eGFP (eGFP-Q19) under tetracycline repression (A, bottom left) were washed and dox-free media added to allow eGFP-Q19 expression (A, top left). Adenoviruses were applied at the indicated multiplicity of infection (MOI) 3 days after dox removal. (A) eGFP fluorescence 3 days after adenovirus-mediated gene transfer of Adsiβgluc (top panels) or AdsiGFP (bottom panels). (B, C) Western blot analysis of cell lysates harvested 3 days after infection at the indicated MOIs demonstrate a dose-dependent decrease in GFP-Q19 protein levels. NV, no virus. Top lanes, eGFP-Q19. Bottom lanes, actin loading controls. (D) Quantitation of eGFP fluorescence. Data represent mean total area fluorescence±standard deviation in 4 low power fields/well (3 wells/plate).

n=9 for saline injected SCA1 mice. WT mice given shLacZ were not significantly different than WT mice treated with saline, shSCA1, or left untreated (data not shown).

Figure 8A:
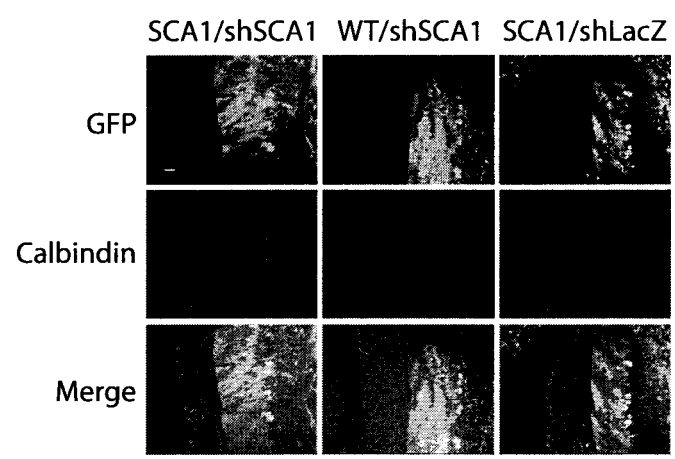
Figure 8B:
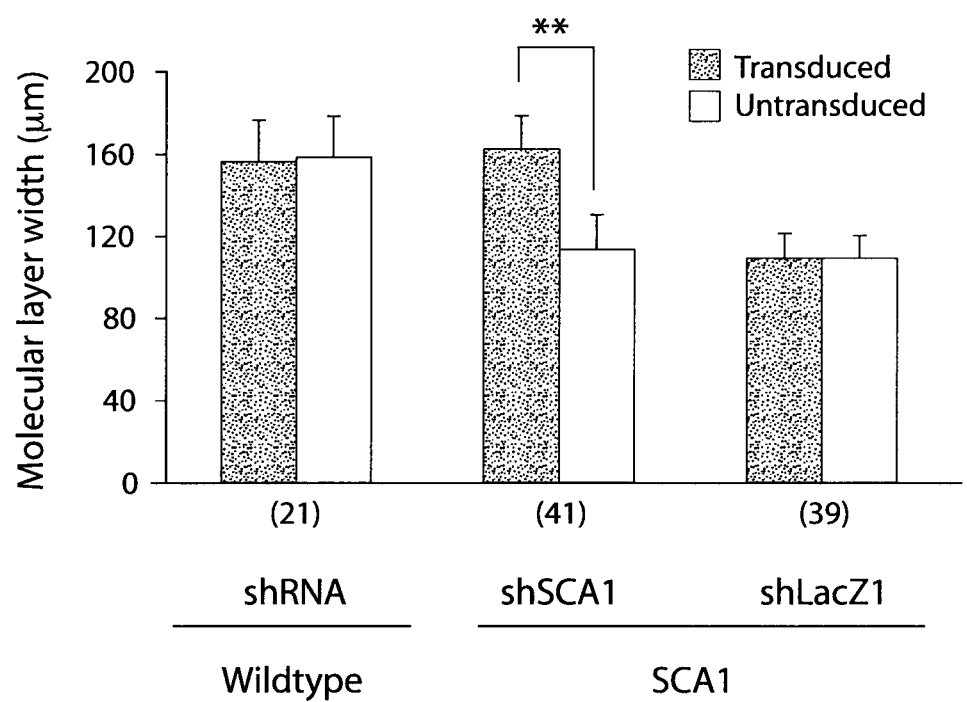
Figure 8C:
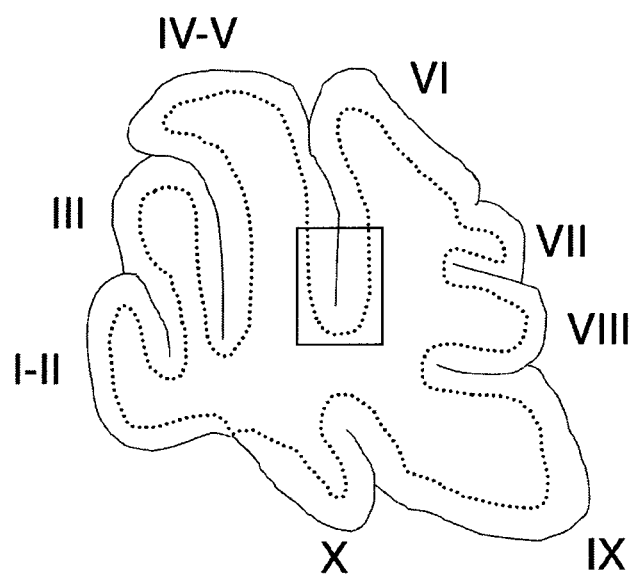

FIG. 8A-C. SCA1 neuropathology is improved by shRNAs directed to ataxin-1. (A) SCA and wildtype mice were injected with AAVshSCA1.F10mi or AAVshLacZ at week 7, and sacrificed 9 weeks later for cerebellar pathology. Calbindin immunofluorescence (IF) (middle panels) and hrGFP expression (top panels) were evaluated. Merged images (bottom panels) demonstrate that hrGFP+ molecular layers from AAVshSCA-injected SCA1 mice have calbindin staining similar to wildtype mice. Panels are representative of 100 or 40 sections evaluated for AAVshSCA1.F10mi-treated SCA1 or wildtype mice, respectively, and 80 sections from AAVshLacZ-treated mice. Bar in upper left panel=50 μm and is representative of all images. (B) The molecular layer width in transduced (solid bars), and untransduced (open bars) lobules from wildtype and SCA1 mice was measured. The data demonstrate significant protection following shSCA1.F10mi therapy. **, $P<0.001$. Numbers below bars refer to numbers of sections measured/group. Molecular layer widths from wildtype mice given AAVs expressing shLacZ or shSCA1.F10mi were indistinguishable and were pooled for comparison to SCA1 mice cerebella (designated shRNA). (C) Photomicrographs shown in A, and FIG. 10, are from the region boxed.

Figure 9:
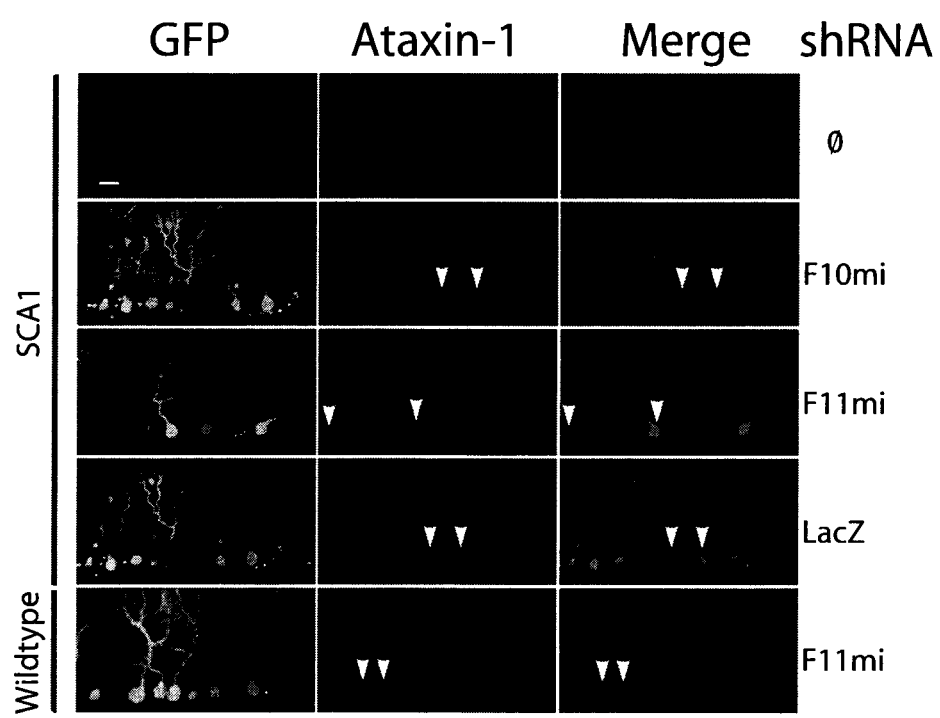

FIG. 9. Effects of shSCA1.F10mi and shSCA1.F11mi on ataxin-1 expression in mice cerebella. SCA1 transgenic or wildtype mice were injected with the indicated shRNA-expressing AAVs, and cerebella harvested 1 week later and processed for hrGFP fluorescence, and ataxin-1 IF. The top panels are from untreated SCA1 mice. The arrowheads in the middle and merged panels depict pairs of Purkinje cells, one transduced (hrGFP+), and one untransduced (hrGFP−), highlighting the extent of reduction in transgenic ataxin-1(Q82) expression from mice injected with AAVshSCA1.F10mi and AAVshSCA1.F11mi, but not AAVshLacZ. Mouse ataxin-1 IF is weak, but notable, in wildtype mice (lower middle panel), and its expression is not reduced following shSCA1.F11mi-treatment. Bar=25 μm and refers to all panels.

Figure 10A:
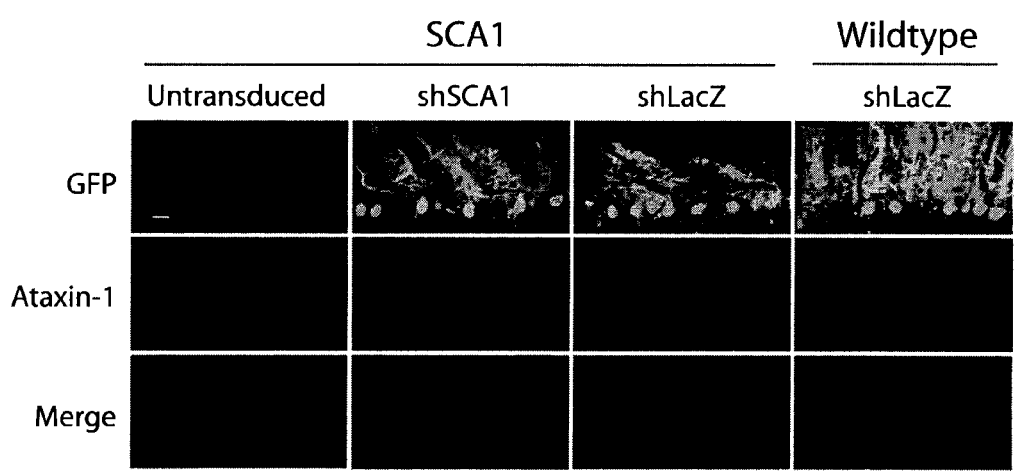
Figure 10B:
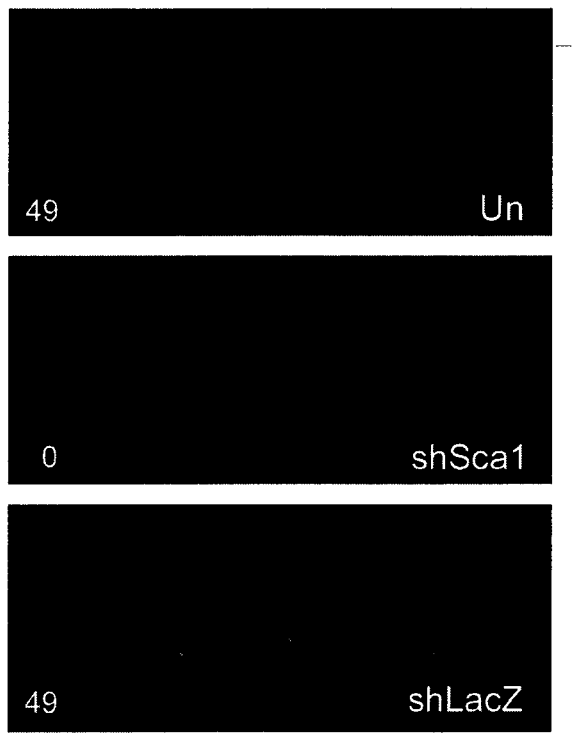

FIG. 10A-B. RNAi reduces intranuclear inclusions in transduced cells. (A) Inclusions in transduced (hrGFP+) vs. untransduced cells. Brains from SCA1 and wildtype mice were harvested 9 weeks after gene transfer (16 weeks of age) and processed to evaluate hrGFP fluorescence and ataxin-1 IF. Bar=25 μm and is representative of all images. (B) Higher magnification of merged hrGFP and ataxin-1 positive cells. There are punctate ataxin-1 inclusions and robust nuclear staining in untransduced (Un) or AAVshLacZ transduced SCA1 Purkinje cells (top and bottom, respectively), but not AAVshSCA1.F10mi transduced ones (middle panel; see also FIG. 11). Numbers in lower left refer to % intranuclear inclusion-positive Purkinje cells in ~400 cells scored.

Figure 11:

FIG. 11. Reductions in ataxin-1 inclusions in SCA1 mice requires transduction. Sections from SCA1 mice injected 9 weeks earlier with AAVshSCA1.F10mi were evaluated for hrGFP expression to identify transduced cells, and ataxin-1 inclusions using IF, as described in the Methods and to the legend of FIG. 4. The photomicrographs demonstrate that ataxin-1 inclusions are noted in untransduced cells, but not transduced cells, from AAVshSCA1.F10mi-treated mice Bar=25 μm.

Figure 12:
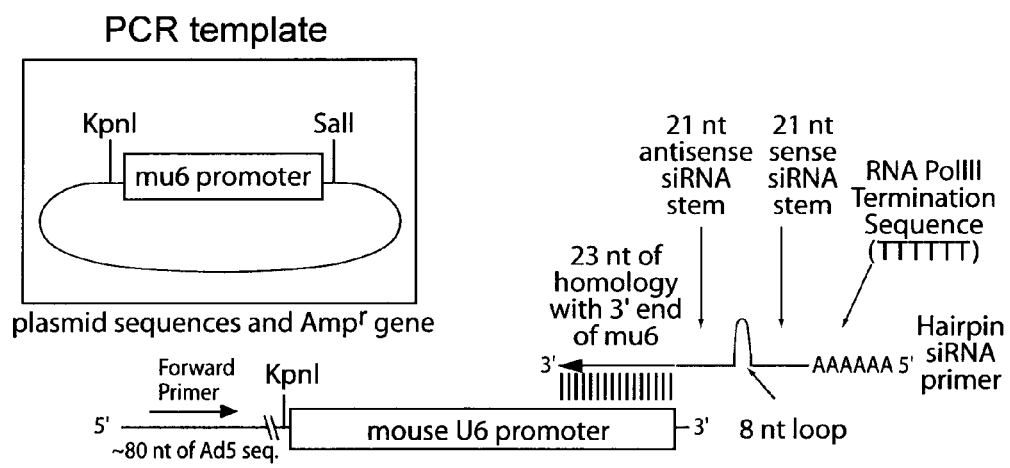

FIG. 12. PCR method for cloning hairpins. A 79 nt primer is used with the Ampr template. Pfu and DMSO are used in the amplification reaction. Products are ligated directly into pCR-Blunt Topo (Invitrogen) and Kanr resistant colonies picked and sequenced. Positive clones can be used directly.

Figure 13:
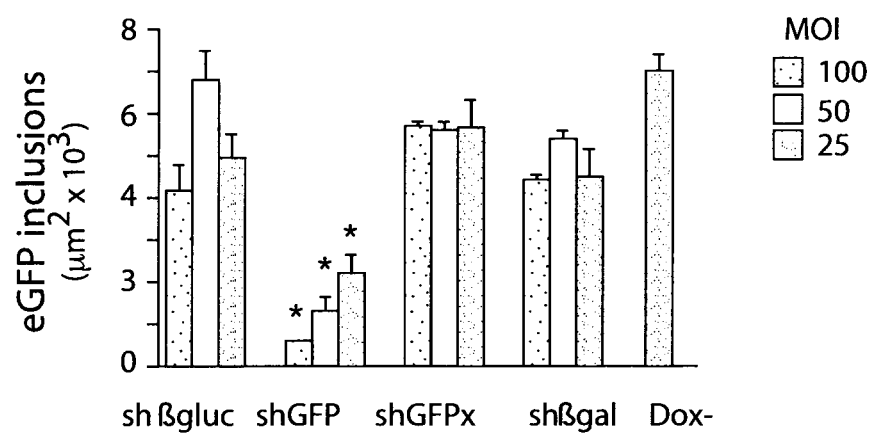

FIG. 13. Reduction of eGFP inclusions after transduction with 25, 50 or 100 viruses/cell into cultures with pre-formed aggregates. Note dose-dependent response with shGFP vectors only.

Figure 14:
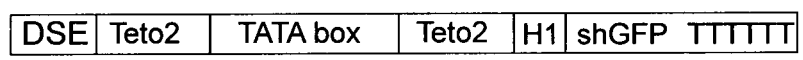
Figure 14:
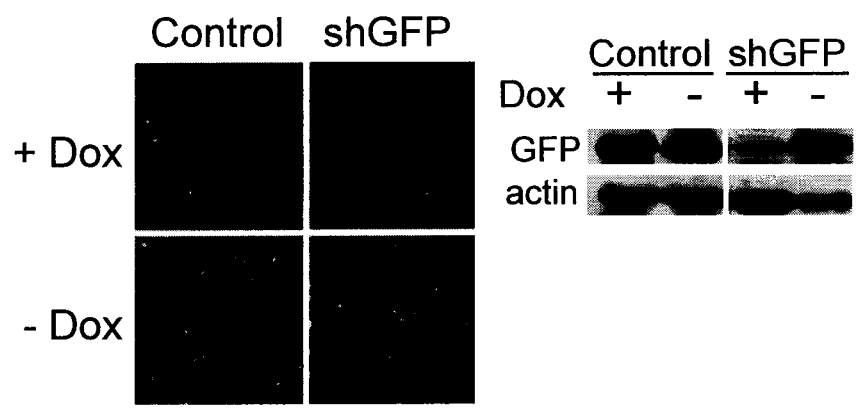

FIG. 14. Regulated RNAi. Two Teto2 sequences were placed up- and down-stream of the TATA box of the H1 promoter element (cartoon). Either control shRNA or shGFP was placed into the cassette for expression of hairpins. Plasmids expressing GFP and the hairpin constructs were transfected into a cell line expressing the TetR (tet-repressor). GFP fluorescence (left panels) or western blot (right panels) was evaluated in the absence (TetR binding) or presence (TetR off) of doxycycline.

Figure 15:
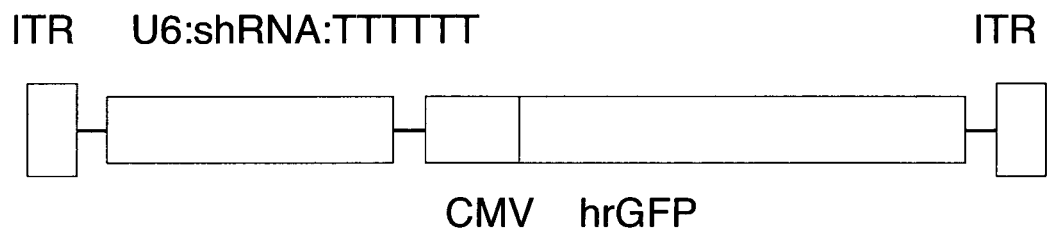

FIG. 15. Top, FIV construct. Bottom, AAV construct. Both express the hrGFP reporter so that transduced cells can be readily evaluated for shRNA efficacy (as in FIGS. 3 and 4).

DETAILED DESCRIPTION OF THE INVENTION

Modulation of gene expression by endogenous, noncoding RNAs is increasingly appreciated as a mechanism playing a role in eukaryotic development, maintenance of chromatin structure and genomic integrity (McManus, 2002). Recently, techniques have been developed to trigger RNA interference (RNAi) against specific targets in mammalian cells by introducing exogenously produced or intracellularly expressed siRNAs (Elbashir, 2001a, 2001b, 2001c; Brummelkamp, 2002). These methods have proven to be quick, inexpensive and effective for knockdown experiments in vitro and in vivo (Elbashir, 2001a, 2001b, 2001c; Brummelkamp, 2002; McCaffrey, 2002; Xia, 2002). The ability to accomplish selective gene silencing has led to the hypothesis that siRNAs might be employed to suppress gene expression for therapeutic benefit (Xia, 2002; Jacque, 2002; Gitlin, 2002).

RNA interference is now established as an important biological strategy for gene silencing, but its application to mammalian cells has been limited by nonspecific inhibitory effects of long double-stranded RNA on translation. Moreover, delivery of interfering RNA has largely been limited to administration of RNA molecules. Hence, such administration must be performed repeatedly to have any sustained effect. The present inventors have developed a delivery mechanism that results in specific silencing of targeted genes through expression of small interfering RNA (siRNA). The inventors have markedly diminished expression of exogenous and endogenous genes in vitro and in vivo in brain and liver, and further apply this novel strategy to a model system of a major class of neurodegenerative disorders, the polyglutamine diseases, to show reduced polyglutamine aggregation in cells. This strategy is generally useful in reducing expression of target genes in order to model biological processes or to provide therapy for dominant human diseases.

Disclosed herein is a strategy that results in substantial silencing of targeted alleles via siRNA. Use of this strategy results in markedly diminished in vitro and in vivo expression of targeted alleles. This strategy is useful in reducing expression of targeted alleles in order to model biological processes or to provide therapy for human diseases. For example, this strategy can be applied to a major class of neurodegenerative disorders, the polyglutamine diseases, as is demonstrated by the reduction of polyglutamine aggregation in cells following application of the strategy. As used herein the term "substantial silencing" means that the mRNA of the targeted allele is inhibited and/or degraded by the presence of the introduced siRNA, such that expression of the targeted allele is reduced by about 10% to 100% as compared to the level of expression seen when the siRNA is not present. Generally, when an allele is substantially silenced, it will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, 98%, 99% or even 100% reduction expression as compared to when the siRNA is not present. As used herein the term "substantially normal activity" means the level of expression of an allele when an siRNA has not been introduced to a cell.

Dominantly inherited diseases, including polyQ neurodegenerative disorders, are ideal candidates for siRNA-based therapy. The polyQ neurodegenerative disorders include at least nine inherited disorders caused by CAG repeat expansions that encode polyQ in the disease protein. PolyQ expansion confers a dominant toxic property on the mutant protein that is associated with aberrant accumulation of the disease protein in neurons (Zoghbi, 2000). All polyQ diseases are progressive, ultimately fatal disorders that typically begin in adulthood. Huntington disease (HD) is the best known polyQ disease, but at least seven hereditary ataxias and one motor neuron disease are also due to CAG repeat/polyQ expansion. Although the clinical features and patterns of neuronal degeneration differ among the diseases, increasing evidence suggests that polyQ diseases share important pathogenic features. In particular, expansion of the CAG repeat/polyQ domain confers upon the encoded protein a dominant toxic property. Thus as a therapeutic strategy, efforts to lower expression of the mutant gene product prior to cell death could be highly beneficial to patients.

Expansions of poly-glutamine tracts in proteins that are expressed in the central nervous system can cause neurodegenerative diseases. Some neurodegenerative diseases are caused by a $(CAG)_n$ repeat that encodes poly-glutamine in a protein include Huntington disease (HD), spinocerebellar ataxia (SCA1, SCA2, SCA3, SCA6, SCAT), spinal and bulbar muscular atrophy (SBMA), and dentatorubropallidoluysian atrophy (DRPLA). In these diseases, the poly-glutamine expansion in a protein confers a novel toxic property upon the protein. Studies indicate that the toxic property is a tendency for the disease protein to misfold and form aggregates within neurons.

CAG triplet repeat expansion in exon 1 of Hdh causes Huntington's disease. Clinical characteristics of HD include progressive loss of striatal neurons and later, cortical thinning. Adult patients show choreiform movements, impaired coordination, progressive dementia and other psychiatric disturbances. The symptoms of juvenile HD patients include bradykinesia, dystonia and seizures. HD is a uniformly fatal disease, with death occurring one to two decades after disease onset.

The Hdh locus is on chromosome 4, spans 180 kb over 67 exons and encodes the protein huntingtin (htt). In non-HD individuals, the CAG repeat region is less than 35 CAG repeats. Expansions of 36 to ~50 repeats, or greater than ~50, cause late or early onset disease, respectively. The inverse correlation of repeat length with age of disease onset is a common characteristic of the CAG repeat disorders, and one that is recapitulated in mouse models. Evidence indicates that HD also may be a dose-dependent process. For example, in transgenic mouse models of polyQ disease, phenotypic severity usually correlates with expression levels of the disease protein, and homozygous transgenic mice develop disease more rapidly than heterozygous mice. In addition, the very rare human cases of homozygosity for polyQ disease suggest that disease severity correlates with the level of disease protein expression, again supporting the notion that reducing mutant protein expression would be clinically beneficial.

The function of htt is not known. It is clear from mouse models, however, that it is required during gastrulation, neurogenesis and in postnatal brain. Htt knock-out mice die during development. Also, removal of htt via Cre recombinase-mediated excision of a floxed Hdh allele causes progressive postnatal neurodegeneration. A CAG expansion introduced into the mouse allele (a knock-in) does not impair neurogenesis unless wildtype htt expression is reduced from normal levels, suggesting that the expanded allele does not impair wildtype htt function in neurogenesis. In adult mice mutant htt causes progressive depletion of normal htt. Htt is important in vesicle trafficking, NMDA receptor modulation, and regulation of BDNF transcription, and the expression of many genes is affected in the CNS of HD mice.

The therapeutic promise of silencing the mutant gene (and its toxic property) is best demonstrated in a tetracycline-regulated mouse model of HD (Yamamoto 2000). When mutant htt is inducibly expressed in these mice, pathological and behavioral features of the disease develop over time, including the characteristic formation of neuronal inclusions and abnormal motor behavior (Yamamoto 2000, On 2000). However, when expression of the transgene is repressed in affected mice, the pathological and behavioral features of disease fully resolve (Yamamoto 2000). This result indicates that if expression of mutant polyQ protein can be halted, protein clearance mechanisms within neurons can eliminate the aggregated mutant protein, and possibly normalize mutant htt-induced changes. It also suggests that gene silencing approaches may be beneficial even for individuals with fairly advanced disease.

One of skill in the art can select additional target sites for generating siRNA specific for other alleles beyond those specifically described in the experimental examples. Such allele-specific siRNAs made be designed using the guidelines provided by Ambion (Austin, Tex.). Briefly, the target cDNA sequence is scanned for target sequences that had AA dinucleotides. Sense and anti-sense oligonucleotides are generated to these targets (AA+3' adjacent 19 nucleotides) that contained a G/C content of 35 to 55%. These sequences are then compared to others in the human genome database to minimize homology to other known coding sequences (BLAST search).

To accomplish intracellular expression of the therapeutic siRNA, an RNA molecule is constructed containing two complementary strands or a hairpin sequence (such as a 21-bp hairpin) representing sequences directed against the gene of interest. The siRNA, or a nucleic acid encoding the siRNA, is introduced to the target cell, such as a diseased brain cell. The siRNA reduces target mRNA and protein expression.

The construct encoding the therapeutic siRNA is configured such that the one or more strands of the siRNA are encoded by a nucleic acid that is immediately contiguous to a promoter. In one example, the promoter is a pol II promoter. If a pol II promoter is used in a particular construct, it is selected from readily available pol II promoters known in the art, depending on whether regulatable, inducible, tissue or cell-specific expression of the siRNA is desired. The construct is introduced into the target cell, allowing for diminished target-gene expression in the cell.

I. Small Interfering RNA (siRNA)

A "small interfering RNA" or "short interfering RNA" or "siRNA" or "short hairpin RNA" or "shRNA" is a RNA duplex of nucleotides that is targeted to a nucleic acid sequence of interest, for example, ataxin-1 or huntingtin (htt). As used herein, the term "siRNA" is a generic term that encompasses the subset of shRNAs. A "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In certain embodiments, the siRNAs are targeted to the sequence encoding ataxin-1 or huntingtin. In some embodiments, the length of the duplex of siRNAs is less than 30 base pairs. In some embodiments, the duplex can be 29, 28, 27, 26, 25, 24, 23, 22, 21, 20, 19, 18, 17, 16, 15, 14, 13, 12, 11 or 10 base pairs in length. In some embodiments, the length of the duplex is 19 to 25 base pairs in length. In certain embodiment, the length of the duplex is 19 or 21 base pairs in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. In certain embodiments, the loop is 9 nucleotides in length. The hairpin structure can also contain 3' or 5' overhang portions. In some embodiments, the overhang is a 3' or a 5' overhang 0, 1, 2, 3, 4 or 5 nucleotides in length.

The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal.

"Knock-down," "knock-down technology" refers to a technique of gene silencing in which the expression of a target gene is reduced as compared to the gene expression prior to the introduction of the siRNA, which can lead to the inhibition of production of the target gene product. The term "reduced" is used herein to indicate that the target gene expression is lowered by 1-100%. In other words, the amount of RNA available for translation into a polypeptide or protein is minimized. For example, the amount of protein may be reduced by 10, 20, 30, 40, 50, 60, 70, 80, 90, 95, or 99%. In some embodiments, the expression is reduced by about 90% (i.e., only about 10% of the amount of protein is observed a cell as compared to a cell where siRNA molecules have not been administered). Knock-down of gene expression can be directed by the use of dsRNAs or siRNAs.

"RNA interference (RNAi)" is the process of sequence-specific, post-transcriptional gene silencing initiated by siRNA. During RNAi, siRNA induces degradation of target mRNA with consequent sequence-specific inhibition of gene expression. RNAi involving the use of siRNA has been successfully applied to knockdown the expression of specific genes in plants, *D. melanogaster, C. elegans*, trypanosomes, planaria, hydra, and several vertebrate species including the mouse. For a review of the mechanisms proposed to mediate RNAi, please refer to Bass et al., 2001 Elbashir, 2001a, 2001b, 2001c; or Brantl, 2002.

According to a method of the present invention, the expression of huntingtin or ataxin-1 can be modified via RNAi. For example, the accumulation of huntingtin or ataxin-1 can be suppressed in a cell. The term "suppressing" refers to the diminution, reduction or elimination in the number or amount of transcripts present in a particular cell. For example, the accumulation of mRNA encoding huntingtin or ataxin-1 can be suppressed in a cell by RNA interference (RNAi), e.g., the gene is silenced by sequence-specific double-stranded RNA (dsRNA), which is also called short interfering RNA (siRNA). These siRNAs can be two separate RNA molecules that have hybridized together, or they may be a single hairpin wherein two portions of a RNA molecule have hybridized together to form a duplex.

A mutant protein refers to the protein encoded by a gene having a mutation, e.g., a missense or nonsense mutation in one or both alleles of huntingtin or atxain-1. A mutant huntingtin or atxain-1 may be disease-causing, i.e., may lead to a disease associated with the presence of huntingtin or atxain-1 in an animal having either one or two mutant allele(s).

The term "gene" is used broadly to refer to any segment of nucleic acid associated with a biological function. Thus, genes include coding sequences and/or the regulatory sequences required for their expression. For example, "gene" refers to a nucleic acid fragment that expresses mRNA, functional RNA, or specific protein, including regulatory sequences. "Genes" also include nonexpressed DNA segments that, for example, form recognition sequences for other proteins. "Genes" can be obtained from a variety of sources, including cloning from a source of interest or synthesizing from known or predicted sequence information, and may include sequences designed to have desired parameters. An "allele" is one of several alternative forms of a gene occupying a given locus on a chromosome.

The term "nucleic acid" refers to deoxyribonucleic acid (DNA) or ribonucleic acid (RNA) and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues. A "nucleic acid fragment" is a portion of a given nucleic acid molecule.

A "nucleotide sequence" is a polymer of DNA or RNA that can be single- or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "polynucleotide" are used interchangeably and may also be used interchangeably with gene, cDNA, DNA and RNA encoded by a gene.

The invention encompasses isolated or substantially purified nucleic acid compositions. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived.

For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. Fragments and variants of the disclosed nucleotide sequences are also encompassed by the present invention. By "fragment" or "portion" is meant a full length or less than full length of the nucleotide sequence.

"Naturally occurring," "native," or "wild-type" is used to describe an object that can be found in nature as distinct from being artificially produced. For example, a protein or nucleotide sequence present in an organism (including a virus), which can be isolated from a source in nature and that has not been intentionally modified by a person in the laboratory, is naturally occurring.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of molecular biology techniques, as, for example, with polymerase chain reaction (PCR) and hybridization techniques. Variant nucleotide sequences also include synthetically derived nucleotide sequences, such as those generated, for example, by using site-directed mutagenesis, which encode the native protein, as well as those that encode a polypeptide having amino acid substitutions. Generally, nucleotide sequence variants of the invention will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

A "vector" is defined to include, inter alia, any viral vector, as well as any plasmid, cosmid, phage or binary vector in double or single stranded linear or circular form that may or may not be self transmissible or mobilizable, and that can transform prokaryotic or eukaryotic host either by integration into the cellular genome or exist extrachromosomally (e.g., autonomous replicating plasmid with an origin of replication).

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. The coding region usually codes for a functional RNA of interest, for example an siRNA. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of an regulatable promoter that initiates transcription only when the host cell is exposed to some particular stimulus. In the case of a multicellular organism, the promoter can also be specific to a particular tissue or organ or stage of development.

Such expression cassettes can include a transcriptional initiation region linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

The term "RNA transcript" or "transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" are nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, regulatable promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency (Turner et al., 1995).

"3' non-coding sequence" refers to nucleotide sequences located 3' (downstream) to a coding sequence and may include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

"Promoter" refers to a nucleotide sequence, usually upstream (5') to its coding sequence, which directs and/or controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. Examples of promoters that may be used in the present invention include the mouse U6 RNA promoters, synthetic human H1RNA promoters, SV40, CMV, RSV, RNA polymerase II and RNA polymerase III promoters.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, heterologous gene or nucleic acid segment, or a transgene in cells. For example, in the case of siRNA constructs, expression may refer to the transcription of the siRNA only. In addition, expression refers to the transcription and stable accumulation of sense (mRNA) or functional RNA. Expression may also refer to the production of protein.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Thus, the determination of percent identity between any two sequences can be accomplished using a mathematical algorithm.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g. BLASTN for nucleotide sequences) can be used. The BLASTN program (for nucleotide sequences) uses as defaults a wordlength (W) of 11, an expectation (E) of 10, a cutoff of 100, M=5, N=−4, and a comparison of both strands. Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide matches and an identical percent sequence identity when compared to the corresponding alignment generated by the preferred program.

(c) As used herein, "sequence identity" or "identity" in the context of two nucleic acid sequences makes reference to a specified percentage of nucleotides in the two sequences that are the same when aligned for maximum correspondence over a specified comparison window, as measured by sequence comparison algorithms or by visual inspection.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) The term "substantial identity" of polynucleotide sequences means that a polynucleotide comprises a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters.

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The Tm is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the Tm can be approximated from the equation of Meinkoth and Wahl (1984); Tm 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. Tm is reduced by about 1° C. for each 1% of mismatching; thus, Tm, hybridization, and/or wash conditions can be adjusted to hybridize to sequences of the desired identity. For example, if sequences with >90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen (1993). Generally, highly stringent hybridization and wash conditions are selected to be about 5° C. lower than the thermal melting point (Tm) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook and Russell 2001, for a description of SSC buffer). Often, a high stringency wash is preceded by a low stringency wash to remove background probe signal. For short nucleic acid sequences (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. Stringent conditions may also be achieved with the addition of destabilizing agents such as formamide. In general, a signal to noise ratio of 2× (or higher) than that observed for an unrelated probe in the particular hybridization assay indicates detection of a specific hybridization. Very stringent conditions are selected to be equal to the Tm for a particular nucleic acid molecule.

The term "transformation" refers to the transfer of a nucleic acid fragment into the genome of a host cell, resulting in genetically stable inheritance. A "host cell" is a cell that has been transformed, or is capable of transformation, by an exogenous nucleic acid molecule. Host cells containing the transformed nucleic acid fragments are referred to as "transgenic" cells.

"Transformed," "transduced," "transgenic" and "recombinant" refer to a host cell into which a heterologous nucleic acid molecule has been introduced. As used herein the term "transfection" refers to the delivery of DNA into eukaryotic (e.g., mammalian) cells. The term "transformation" is used herein to refer to delivery of DNA into prokaryotic (e.g., *E. coli*) cells. The term "transduction" is used herein to refer to infecting cells with viral particles. The nucleic acid molecule can be stably integrated into the genome generally known in the art. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome.

The term "untransformed" refers to normal cells that have not been through the transformation process.

"Genetically altered cells" denotes cells which have been modified by the introduction of recombinant or heterologous nucleic acids (e.g., one or more DNA constructs or their RNA counterparts) and further includes the progeny of such cells which retain part or all of such genetic modification.

As used herein, the term "derived" or "directed to" with respect to a nucleotide molecule means that the molecule has complementary sequence identity to a particular molecule of interest.

"Gene silencing" refers to the suppression of gene expression, e.g., transgene, heterologous gene and/or endogenous gene expression. Gene silencing may be mediated through processes that affect transcription and/or through processes that affect post-transcriptional mechanisms. In some embodiments, gene silencing occurs when siRNA initiates the degradation of the mRNA of a gene of interest in a sequence-specific manner via RNA interference (for a review, see Brantl, 2002). In some embodiments, gene silencing may be allele-specific. "Allele-specific" gene silencing refers to the specific silencing of one allele of a gene.

"Treating" as used herein refers to ameliorating at least one symptom of, curing and/or preventing the development of a disease or a condition.

"Neurological disease" and "neurological disorder" refer to both hereditary and sporadic conditions that are characterized by nervous system dysfunction, and which may be associated with atrophy of the affected central or peripheral nervous system structures, or loss of function without atrophy. A neurological disease or disorder that results in atrophy is commonly called a "neurodegenerative disease" or "neurodegenerative disorder." Neurodegenerative diseases and disorders include, but are not limited to, amyotrophic lateral sclerosis (ALS), hereditary spastic hemiplegia, primary lateral sclerosis, spinal muscular atrophy, Kennedy's disease, Alzheimer's disease, Parkinson's disease, multiple sclerosis, and repeat expansion neurodegenerative diseases, e.g., diseases associated with expansions of trinucleotide repeats such as polyglutamine (polyQ) repeat diseases, e.g., Huntington's disease (HD), spinocerebellar ataxia (SCA1, SCA2, SCA3, SCA6, SCAT, and SCA17), spinal and bulbar muscular atrophy (SBMA), dentatorubropallidoluysian atrophy (DRPLA). An example of a neurological disorder that does not appear to result in atrophy is DYT1 dystonia.

The siRNAs of the present invention can be generated by any method known to the art, for example, by in vitro transcription, recombinantly, or by synthetic means. In one example, the siRNAs can be generated in vitro by using a recombinant enzyme, such as T7 RNA polymerase, and DNA oligonucleotide templates.

II. Nucleic Acid Molecules of the Invention

The terms "isolated and/or purified" refer to in vitro isolation of a nucleic acid, e.g., a DNA or RNA molecule from its natural cellular environment, and from association with other components of the cell, such as nucleic acid or polypeptide, so that it can be sequenced, replicated, and/or expressed. For example, "isolated nucleic acid" may be a DNA molecule containing less than 31 sequential nucleotides that is transcribed into an siRNA. Such an isolated siRNA may, for example, form a hairpin structure with a duplex 21 base pairs in length that is complementary or hybridizes to a sequence in a gene of interest, and remains stably bound under stringent conditions (as defined by methods well known in the art, e.g., in Sambrook and Russell, 2001). Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

In addition to a DNA sequence encoding a siRNA, the nucleic acid molecules of the invention include double-stranded interfering RNA molecules, which are also useful to inhibit expression of a target gene.

As used herein, the term "recombinant nucleic acid", e.g., "recombinant DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. Therefore, "recombinant DNA" includes completely synthetic DNA sequences, semi-synthetic DNA sequences, DNA sequences isolated from biological sources, and DNA sequences derived from RNA, as well as mixtures thereof.

Nucleic acid molecules having base substitutions (i.e., variants) are prepared by a variety of methods known in the art. These methods include, but are not limited to, isolation from a natural source (in the case of naturally occurring sequence variants) or preparation by oligonucleotide-mediated (or site-directed) mutagenesis, PCR mutagenesis, and cassette mutagenesis of an earlier prepared variant or a non-variant version of the nucleic acid molecule.

Oligonucleotide-mediated mutagenesis is a method for preparing substitution variants. This technique is known in the art as described by Adelman et al. (1983). Briefly, nucleic acid encoding a siRNA can be altered by hybridizing an oligonucleotide encoding the desired mutation to a DNA template, where the template is the single-stranded form of a plasmid or bacteriophage containing the unaltered or native gene sequence. After hybridization, a DNA polymerase is used to synthesize an entire second complementary strand of the template that will thus incorporate the oligonucleotide primer, and will code for the selected alteration in the nucleic acid encoding siRNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art.

The DNA template can be generated by those vectors that are either derived from bacteriophage M13 vectors (the commercially available M13 mp 18 and M13 mp 19 vectors are suitable), or those vectors that contain a single-stranded phage origin of replication. Thus, the DNA that is to be mutated may be inserted into one of these vectors to generate single-stranded template. Production of the single-stranded template is described in Chapter 3 of Sambrook and Russell, 2001. Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the DNA, and the other strand (the original template) encodes the native, unaltered sequence of the DNA. This heteroduplex molecule is then transformed into a suitable host cell, usually a prokaryote such as *E. coli* JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-(*S) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(*S) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101.

There are well-established criteria for designing siRNAs (see, e.g., Elbashire et al., 2001a, 2001b, 2001c). Details can be found in the websites of several commercial vendors such as Ambion, Dharmacon and Oligoengine. However, since the mechanism for siRNAs suppressing gene expression is not entirely understood and siRNAs selected from different regions of the same gene do not work as equally effective, very often a number of siRNAs have to be generated at the same time in order to compare their effectiveness.

III. Expression Cassettes of the Invention

To prepare expression cassettes, the recombinant DNA sequence or segment may be circular or linear, double-stranded or single-stranded. Generally, the DNA sequence or segment is in the form of chimeric DNA, such as plasmid DNA or a vector that can also contain coding regions flanked by control sequences that promote the expression of the recombinant DNA present in the resultant transformed cell.

A "chimeric" vector or expression cassette, as used herein, means a vector or cassette including nucleic acid sequences from at least two different species, or has a nucleic acid sequence from the same species that is linked or associated in a manner that does not occur in the "native" or wild type of the species.

Aside from recombinant DNA sequences that serve as transcription units for an RNA transcript, or portions thereof, a portion of the recombinant DNA may be untranscribed, serving a regulatory or a structural function. For example, the recombinant DNA may have a promoter that is active in mammalian cells.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, stability of the siRNA, or the like. Such elements may be included in the DNA as desired to obtain the optimal performance of the siRNA in the cell.

Control sequences are DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

Operably linked nucleic acids are nucleic acids placed in a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, operably linked DNA sequences are DNA sequences that are linked are contiguous. However, enhancers do not have to be contiguous. Linking is accomplished by ligation at convenient restriction sites. If such sites do not exist, the synthetic oligonucleotide adaptors or linkers are used in accord with conventional practice.

The recombinant DNA to be introduced into the cells may contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. For example, reporter genes include the chloramphenicol acetyl transferase gene (cat) from Tn9 of *E. coli* and the luciferase gene from firefly *Photinus pyralis*. Expression of the reporter gene is assayed at a suitable time after the DNA has been introduced into the recipient cells.

The general methods for constructing recombinant DNA that can transfect target cells are well known to those skilled in the art, and the same compositions and methods of construction may be utilized to produce the DNA useful herein. For example, Sambrook and Russell, infra, provides suitable methods of construction.

The recombinant DNA can be readily introduced into the host cells, e.g., mammalian, bacterial, yeast or insect cells by transfection with an expression vector composed of DNA encoding the siRNA by any procedure useful for the introduction into a particular cell, e.g., physical or biological methods, to yield a cell having the recombinant DNA stably integrated into its genome or existing as a episomal element, so that the DNA molecules, or sequences of the present invention are expressed by the host cell. Preferably, the DNA is introduced into host cells via a vector. The host cell is preferably of eukaryotic origin, e.g., plant, mammalian, insect, yeast or fungal sources, but host cells of non-eukaryotic origin may also be employed.

Physical methods to introduce a preselected DNA into a host cell include calcium phosphate precipitation, lipofection, particle bombardment, microinjection, electroporation, and the like. Biological methods to introduce the DNA of interest into a host cell include the use of DNA and RNA viral vectors. For mammalian gene therapy, as described herein below, it is desirable to use an efficient means of inserting a copy gene into the host genome. Viral vectors, and especially retroviral vectors, have become the most widely used method for inserting genes into mammalian, e.g., human cells. Other viral vectors can be derived from poxviruses, herpes simplex virus I, adenoviruses and adeno-associated viruses, and the like. See, for example, U.S. Pat. Nos. 5,350,674 and 5,585,362.

As discussed above, a "transfected", or "transduced" host cell or cell line is one in which the genome has been altered or augmented by the presence of at least one heterologous or recombinant nucleic acid sequence. The host cells of the present invention are typically produced by transfection with a DNA sequence in a plasmid expression vector, a viral expression vector, or as an isolated linear DNA sequence. The transfected DNA can become a chromosomally integrated recombinant DNA sequence, which is composed of sequence encoding the siRNA.

To confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

To detect and quantitate RNA produced from introduced recombinant DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the recombinant DNA segment in question, they do not provide information as to whether the preselected DNA segment is being expressed. Expression may be evaluated by specifically identifying the peptide products of the introduced recombinant DNA sequences or evaluating the phenotypic changes brought about by the expression of the introduced recombinant DNA segment in the host cell.

The instant invention provides a cell expression system for expressing exogenous nucleic acid material in a mammalian recipient. The expression system, also referred to as a "genetically modified cell", comprises a cell and an expression vector for expressing the exogenous nucleic acid material. The genetically modified cells are suitable for administration to a mammalian recipient, where they replace the endogenous cells of the recipient. Thus, the preferred genetically modified cells are non-immortalized and are non-tumorigenic.

According to one embodiment, the cells are transfected or otherwise genetically modified ex vivo. The cells are isolated from a mammal (preferably a human), nucleic acid introduced (i.e., transduced or transfected in vitro) with a vector for expressing a heterologous (e.g., recombinant) gene encoding the therapeutic agent, and then administered to a mammalian recipient for delivery of the therapeutic agent in situ. The mammalian recipient may be a human and the cells to be modified are autologous cells, i.e., the cells are isolated from the mammalian recipient.

According to another embodiment, the cells are transfected or transduced or otherwise genetically modified in vivo. The cells from the mammalian recipient are transduced or transfected in vivo with a vector containing exogenous nucleic acid material for expressing a heterologous (e.g., recombinant) gene encoding a therapeutic agent and the therapeutic agent is delivered in situ.

As used herein, "exogenous nucleic acid material" refers to a nucleic acid or an oligonucleotide, either natural or synthetic, which is not naturally found in the cells; or if it is naturally found in the cells, is modified from its original or native form. Thus, "exogenous nucleic acid material" includes, for example, a non-naturally occurring nucleic acid that can be transcribed into an anti-sense RNA, a siRNA, as well as a "heterologous gene" (i.e., a gene encoding a protein that is not expressed or is expressed at biologically insignificant levels in a naturally-occurring cell of the same type). To illustrate, a synthetic or natural gene encoding human erythropoietin (EPO) would be considered "exogenous nucleic acid material" with respect to human peritoneal mesothelial cells since the latter cells do not naturally express EPO. Still another example of "exogenous nucleic acid material" is the introduction of only part of a gene to create a recombinant gene, such as combining an regulatable promoter with an endogenous coding sequence via homologous recombination.

IV. Methods for Introducing the Expression Cassettes of the Invention into Cells The condition amenable to gene inhibition therapy may be a prophylactic process, i.e., a process for preventing disease or an undesired medical condition. Thus, the instant invention embraces a system for delivering siRNA that has a prophylactic function (i.e., a prophylactic agent) to the mammalian recipient.

The inhibitory nucleic acid material (e.g., an expression cassette encoding siRNA directed to a gene of interest) can be introduced into the cell ex vivo or in vivo by genetic transfer methods, such as transfection or transduction, to provide a genetically modified cell. Various expression vectors (i.e., vehicles for facilitating delivery of exogenous nucleic acid into a target cell) are known to one of ordinary skill in the art.

As used herein, "transfection of cells" refers to the acquisition by a cell of new nucleic acid material by incorporation of added DNA. Thus, transfection refers to the insertion of nucleic acid into a cell using physical or chemical methods. Several transfection techniques are known to those of ordinary skill in the art including calcium phosphate DNA co-precipitation, DEAE-dextran, electroporation, cationic liposome-mediated transfection, tungsten particle-facilitated microparticle bombardment, and strontium phosphate DNA co-precipitation.

In contrast, "transduction of cells" refers to the process of transferring nucleic acid into a cell using a DNA or RNA virus. A RNA virus (i.e., a retrovirus) for transferring a nucleic acid into a cell is referred to herein as a transducing chimeric retrovirus. Exogenous nucleic acid material contained within the retrovirus is incorporated into the genome of the transduced cell. A cell that has been transduced with a chimeric DNA virus (e.g., an adenovirus carrying a cDNA encoding a therapeutic agent), will not have the exogenous nucleic acid material incorporated into its genome but will be capable of expressing the exogenous nucleic acid material that is retained extrachromosomally within the cell.

The exogenous nucleic acid material can include the nucleic acid encoding the siRNA together with a promoter to control transcription. The promoter characteristically has a specific nucleotide sequence necessary to initiate transcription. The exogenous nucleic acid material may further include additional sequences (i.e., enhancers) required to obtain the desired gene transcription activity. For the purpose of this discussion an "enhancer" is simply any non-translated DNA sequence that works with the coding sequence (in cis) to change the basal transcription level dictated by the promoter. The exogenous nucleic acid material may be introduced into the cell genome immediately downstream from the promoter so that the promoter and coding sequence are operatively linked so as to permit transcription of the coding sequence. An expression vector can include an exogenous promoter element to control transcription of the inserted exogenous gene. Such exogenous promoters include both constitutive and regulatable promoters.

Naturally-occurring constitutive promoters control the expression of essential cell functions. As a result, a nucleic acid sequence under the control of a constitutive promoter is expressed under all conditions of cell growth. Constitutive promoters include the promoters for the following genes which encode certain constitutive or "housekeeping" functions: hypoxanthine phosphoribosyl transferase (HPRT), dihydrofolate reductase (DHFR), adenosine deaminase, phosphoglycerol kinase (PGK), pyruvate kinase, phosphoglycerol mutase, the beta-actin promoter, and other constitutive promoters known to those of skill in the art. In addition, many viral promoters function constitutively in eukaryotic cells. These include: the early and late promoters of SV40; the long terminal repeats (LTRs) of Moloney Leukemia Virus and other retroviruses; and the thymidine kinase promoter of Herpes Simplex Virus, among many others.

Nucleic acid sequences that are under the control of regulatable promoters are expressed only or to a greater or lesser degree in the presence of an inducing or repressing agent, (e.g., transcription under control of the metallothionein promoter is greatly increased in presence of certain metal ions). Regulatable promoters include responsive elements (REs) that stimulate transcription when their inducing factors are bound. For example, there are REs for serum factors, steroid hormones, retinoic acid, cyclic AMP, and tetracycline and doxycycline. Promoters containing a particular RE can be chosen in order to obtain an regulatable response and in some cases, the RE itself may be attached to a different promoter, thereby conferring regulatability to the encoded nucleic acid sequence. Thus, by selecting the appropriate promoter (constitutive versus regulatable; strong versus weak), it is possible to control both the existence and level of expression of a nucleic acid sequence in the genetically modified cell. If the nucleic acid sequence is under the control of an regulatable promoter, delivery of the therapeutic agent in situ is triggered by exposing the genetically modified cell in situ to conditions for permitting transcription of the nucleic acid sequence, e.g., by intraperitoneal injection of specific inducers of the regulatable promoters which control transcription of the agent. For example, in situ expression of a nucleic acid sequence under the control of the metallothionein promoter in genetically modified cells is enhanced by contacting the genetically modified cells with a solution containing the appropriate (i.e., inducing) metal ions in situ.

Accordingly, the amount of siRNA generated in situ is regulated by controlling such factors as the nature of the promoter used to direct transcription of the nucleic acid sequence, (i.e., whether the promoter is constitutive or regulatable, strong or weak) and the number of copies of the exogenous nucleic acid sequence encoding a siRNA sequence that are in the cell.

In one embodiment of the present invention, an expression cassette may contain a pol II promoter that is operably linked to a nucleic acid sequence encoding a siRNA. Thus, the pol II promoter, i.e., a RNA polymerase II dependent promoter, initiates the transcription of the siRNA. In another embodiment, the pol II promoter is regulatable.

A pol II promoter may be used in its entirety, or a portion or fragment of the promoter sequence may be used in which the portion maintains the promoter activity. As discussed herein, pol II promoters are known to a skilled person in the art and include the promoter of any protein-encoding gene, e.g., an endogenously regulated gene or a constitutively expressed gene. For example, the promoters of genes regulated by cellular physiological events, e.g., heat shock, oxygen levels and/or carbon monoxide levels, e.g., in hypoxia, may be used in the expression cassettes of the invention. In addition, the promoter of any gene regulated by the presence of a pharmacological agent, e.g., tetracycline and derivatives thereof, as well as heavy metal ions and hormones may be employed in the expression cassettes of the invention. In an embodiment of the invention, the pol II promoter can be the CMV promoter or the RSV promoter. In another embodiment, the pol II promoter is the CMV promoter.

As discussed above, a pol II promoter of the invention may be one naturally associated with an endogenously regulated gene or sequence, as may be obtained by isolating the 5' non-coding sequences located upstream of the coding segment and/or exon. The pol II promoter of the expression cassette can be, for example, the same pol II promoter driving expression of the targeted gene of interest. Alternatively, the nucleic acid sequence encoding the siRNA may be placed under the control of a recombinant or heterologous pol II promoter, which refers to a promoter that is not normally associated with the targeted gene's natural environment. Such promoters include promoters isolated from any eukaryotic cell, and promoters not "naturally occurring," i.e., containing different elements of different transcriptional regulatory regions, and/or mutations that alter expression. In addition to producing nucleic acid sequences of promoters synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference).

In one embodiment, a pol II promoter that effectively directs the expression of the siRNA in the cell type, organelle, and organism chosen for expression will be employed. Those of ordinary skill in the art of molecular biology generally know the use of promoters for protein expression, for example, see Sambrook and Russell (2001), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The identity of tissue-specific promoters, as well as assays to characterize their activity, is well known to those of ordinary skill in the art.

In addition to at least one promoter and at least one heterologous nucleic acid sequence encoding the siRNA, the expression vector may include a selection gene, for example, a neomycin resistance gene, for facilitating selection of cells that have been transfected or transduced with the expression vector.

Cells can also be transfected with two or more expression vectors, at least one vector containing the nucleic acid sequence(s) encoding the siRNA(s), the other vector containing a selection gene. The selection of a suitable promoter, enhancer, selection gene and/or signal sequence is deemed to be within the scope of one of ordinary skill in the art without undue experimentation.

The following discussion is directed to various utilities of the instant invention. For example, the instant invention has utility as an expression system suitable for silencing the expression of gene(s) of interest.

The instant invention also provides methods for genetically modifying cells of a mammalian recipient in vivo. According to one embodiment, the method comprises introducing an expression vector for expressing a siRNA sequence in cells of the mammalian recipient in situ by, for example, injecting the vector into the recipient.

V. Delivery Vehicles for the Expression Cassettes of the Invention

Delivery of compounds into tissues and across the blood-brain barrier can be limited by the size and biochemical properties of the compounds. Currently, efficient delivery of compounds into cells in vivo can be achieved only when the molecules are small (usually less than 600 Daltons). Gene transfer for the correction of inborn errors of metabolism and neurodegenerative diseases of the central nervous system (CNS), and for the treatment of cancer has been accomplished with recombinant adenoviral vectors.

The selection and optimization of a particular expression vector for expressing a specific siRNA in a cell can be accomplished by obtaining the nucleic acid sequence of the siRNA, possibly with one or more appropriate control regions (e.g., promoter, insertion sequence); preparing a vector construct comprising the vector into which is inserted the nucleic acid sequence encoding the siRNA; transfecting or transducing cultured cells in vitro with the vector construct; and determining whether the siRNA is present in the cultured cells.

Vectors for cell gene therapy include viruses, such as replication-deficient viruses (described in detail below). Exemplary viral vectors are derived from Harvey Sarcoma virus, ROUS Sarcoma virus, (MPSV), Moloney murine leukemia virus and DNA viruses (e.g., adenovirus).

Replication-deficient retroviruses are capable of directing synthesis of all virion proteins, but are incapable of making infectious particles. Accordingly, these genetically altered retroviral expression vectors have general utility for high-efficiency transduction of nucleic acid sequences in cultured cells, and specific utility for use in the method of the present invention. Such retroviruses further have utility for the efficient transduction of nucleic acid sequences into cells in vivo. Retroviruses have been used extensively for transferring nucleic acid material into cells. Protocols for producing replication-deficient retroviruses (including the steps of incorporation of exogenous nucleic acid material into a plasmid, transfection of a packaging cell line with plasmid, production of recombinant retroviruses by the packaging cell line, collection of viral particles from tissue culture media, and infection of the target cells with the viral particles) are well known in the art.

An advantage of using retroviruses for gene therapy is that the viruses insert the nucleic acid sequence encoding the siRNA into the host cell genome, thereby permitting the nucleic acid sequence encoding the siRNA to be passed on to the progeny of the cell when it divides. Promoter sequences in the LTR region have can enhance expression of an inserted coding sequence in a variety of cell types. Some disadvantages of using a retrovirus expression vector are (1) insertional mutagenesis, i.e., the insertion of the nucleic acid sequence encoding the siRNA into an undesirable position in the target cell genome which, for example, leads to unregulated cell growth and (2) the need for target cell proliferation in order for the nucleic acid sequence encoding the siRNA carried by the vector to be integrated into the target genome.

Another viral candidate useful as an expression vector for transformation of cells is the adenovirus, a double-stranded DNA virus. The adenovirus is infective in a wide range of cell types, including, for example, muscle and endothelial cells.

Adenoviruses (Ad) are double-stranded linear DNA viruses with a 36 kb genome. Several features of adenovirus have made them useful as transgene delivery vehicles for therapeutic applications, such as facilitating in vivo gene delivery. Recombinant adenovirus vectors have been shown to be capable of efficient in situ gene transfer to parenchymal cells of various organs, including the lung, brain, pancreas, gallbladder, and liver. This has allowed the use of these vectors in methods for treating inherited genetic diseases, such as cystic fibrosis, where vectors may be delivered to a target organ. In addition, the ability of the adenovirus vector to accomplish in situ tumor transduction has allowed the development of a variety of anticancer gene therapy methods for non-disseminated disease. In these methods, vector containment favors tumor cell-specific transduction.

Like the retrovirus, the adenovirus genome is adaptable for use as an expression vector for gene therapy, i.e., by removing the genetic information that controls production of the virus itself. Because the adenovirus functions in an extrachromosomal fashion, the recombinant adenovirus does not have the theoretical problem of insertional mutagenesis.

Several approaches traditionally have been used to generate the recombinant adenoviruses. One approach involves direct ligation of restriction endonuclease fragments containing a nucleic acid sequence of interest to portions of the adenoviral genome. Alternatively, the nucleic acid sequence of interest may be inserted into a defective adenovirus by homologous recombination results. The desired recombinants are identified by screening individual plaques generated in a lawn of complementation cells.

Most adenovirus vectors are based on the adenovirus type 5 (Ad5) backbone in which an expression cassette containing the nucleic acid sequence of interest has been introduced in place of the early region 1 (E1) or early region 3 (E3). Viruses in which E1 has been deleted are defective for replication and are propagated in human complementation cells (e.g., 293 or 911 cells), which supply the missing gene E1 and pIX in trans.

In one embodiment of the present invention, one will desire to generate siRNA in a brain cell or brain tissue. A suitable vector for this application is an FIV vector (Brooks et al. (2002); Alisky et al. (2000a)) or an AAV vector. For example, one may use AAV5 (Davidson et al. (2000); Alisky et al. (2000a)). Also, one may apply poliovirus (Bledsoe et al. (2000)) or HSV vectors (Alisky et al. (2000b)).

Application of siRNA is generally accomplished by transfection of synthetic siRNAs, in vitro synthesized RNAs, or plasmids expressing short hairpin RNAs (shRNAs). More recently, viruses have been employed for in vitro studies and to generate transgenic mouse knock-downs of targeted genes (Hannon 2002, Rubinson 2003, Kunath 2003). Recombinant adenovirus, adeno-associated virus (AAV) and feline immunodeficiency virus (FIV) can be used to deliver genes in vitro and in vivo (Alisky 2000, Davidson 2000, Brooks 2000). Each has its own advantages and disadvantages (Davidson 2003). Adenoviruses are double stranded DNA viruses with large genomes (36 kb) and have been engineered by my laboratory and others to accommodate expression cassettes in distinct regions. We used recombinant adenoviruses expressing siRNAs to demonstrate successful viral-mediated gene suppression in brain (Xia 2002).

Adeno-associated viruses have encapsidated genomes, similar to Ad, but are smaller in size and packaging capacity (~30 nm vs. ~100 nm; packaging limit of ~4.5 kb). AAV contain single stranded DNA genomes of the + or the − strand. Eight serotypes of AAV (1-8) have been studied extensively, three of which have been evaluated in the brain (Davidson 2000, Passini 2003, Skorupa 1999, Frisella 2001, Xiao 1997, During 1998). An important consideration for the present application is that AAV5 transduces striatal and cortical neurons, and is not associated with any known pathologies.

FIV is an enveloped virus with a strong safety profile in humans; individuals bitten or scratched by FIV-infected cats do not seroconvert and have not been reported to show any signs of disease. Like AAV, FIV provides lasting transgene expression in mouse and nonhuman primate neurons (Brooks 2002, Lotery 2002), and transduction can be directed to different cell types by pseudotyping, the process of exchanging the viruses native envelope for an envelope from another virus (Kang 2002, Stein 2001).

Thus, as will be apparent to one of ordinary skill in the art, a variety of suitable viral expression vectors are available for transferring exogenous nucleic acid material into cells. The selection of an appropriate expression vector to express a therapeutic agent for a particular condition amenable to gene silencing therapy and the optimization of the conditions for insertion of the selected expression vector into the cell, are within the scope of one of ordinary skill in the art without the need for undue experimentation.

In another embodiment, the expression vector is in the form of a plasmid, which is transferred into the target cells by one of a variety of methods: physical (e.g., microinjection, electroporation, scrape loading, microparticle bombardment) or by cellular uptake as a chemical complex (e.g., calcium or strontium co-precipitation, complexation with lipid, complexation with ligand). Several commercial products are available for cationic liposome complexation including Lipofectin™ (Gibco-BRL, Gaithersburg, Md.) and Transfectam™ (ProMega, Madison, Wis.). However, the efficiency of transfection by these methods is highly dependent on the nature of the target cell and accordingly, the conditions for optimal transfection of nucleic acids into cells using the above-mentioned procedures must be optimized. Such optimization is within the scope of one of ordinary skill in the art without the need for undue experimentation.

VI. Diseases and Conditions Amendable to the Methods of the Invention

In the certain embodiments of the present invention, a mammalian recipient to an expression cassette of the invention has a condition that is amenable to gene silencing therapy. As used herein, "gene silencing therapy" refers to administration to the recipient exogenous nucleic acid material encoding a therapeutic siRNA and subsequent expression of the administered nucleic acid material in situ. Thus, the phrase "condition amenable to siRNA therapy" embraces conditions such as genetic diseases (i.e., a disease condition that is attributable to one or more gene defects), acquired pathologies (i.e., a pathological condition that is not attributable to an inborn defect), cancers, neurodegenerative diseases, e.g., trinucleotide repeat disorders, and prophylactic processes (i.e., prevention of a disease or of an undesired medical condition). A gene "associated with a condition" is a gene that is either the cause, or is part of the cause, of the condition to be treated. Examples of such genes include genes associated with a neurodegenerative disease (e.g., a trinucleotide-repeat disease such as a disease associated with polyglutamine repeats, Huntington's disease, and several spinocerebellar ataxias), and genes encoding ligands for chemokines involved in the migration of a cancer cells, or chemokine receptor. Also siRNA expressed from viral vectors may be used for in vivo antiviral therapy using the vector systems described.

Accordingly, as used herein, the term "therapeutic siRNA" refers to any siRNA that has a beneficial effect on the recipient. Thus, "therapeutic siRNA" embraces both therapeutic and prophylactic siRNA.

Differences between alleles that are amenable to targeting by siRNA include disease-causing mutations as well as polymorphisms that are not themselves mutations, but may be linked to a mutation or associated with a predisposition to a disease state. An example of a targetable polymorphism that is not itself a mutation is the polymorphism in exon 58 associated with Huntington's disease. Single nucleotide polymorphisms comprise most of the genetic diversity between humans. The major risk factor for developing Alzheimer's disease is the presence of a particular polymorphism in the apolipoprotein E gene.

VII. Dosages, Formulations and Routes of Administration of the Agents of the Invention The agents of the invention are preferably administered so as to result in a reduction in at least one symptom associated with a disease. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems, which are well known to the art.

Administration of siRNA may be accomplished through the administration of the nucleic acid molecule encoding the siRNA. Pharmaceutical formulations, dosages and routes of administration for nucleic acids are generally disclosed, for example, in Felgner 1987.

The present invention envisions treating a disease, for example, a neurodegenerative disease, in a mammal by the administration of an agent, e.g., a nucleic acid composition, an expression vector, or a viral particle of the invention. Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

One or more suitable unit dosage forms having the therapeutic agent(s) of the invention, which, as discussed below, may optionally be formulated for sustained release (for example using microencapsulation, see WO 94/07529, and U.S. Pat. No. 4,962,091 the disclosures of which are incorporated by reference herein), can be administered by a variety of routes including parenteral, including by intravenous and intramuscular routes, as well as by direct injection into the diseased tissue. For example, the therapeutic agent may be directly injected into the brain. Alternatively the therapeutic agent may be introduced intrathecally for brain and spinal cord conditions. In another example, the therapeutic agent may be introduced intramuscularly for viruses that traffic back to affected neurons from muscle, such as AAV, lentivirus and adenovirus. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules, as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions such as phosphate buffered saline solutions pH 7.0-8.0. saline solutions and water.

The invention will now be illustrated by the following non-limiting Examples.

EXAMPLE 1 siRNA-Mediated Silencing of Genes Using Viral Vectors

In this Example, it is shown that genes can be silenced in an allele-specific manner. It is also demonstrated that viral-mediated delivery of siRNA can specifically reduce expression of targeted genes in various cell types, both in vitro and in vivo. This strategy was then applied to reduce expression of a neurotoxic polyglutamine disease protein. The ability of viral vectors to transduce cells efficiently in vivo, coupled with the efficacy of virally expressed siRNA shown here, extends the application of siRNA to viral-based therapies and in vivo targeting experiments that aim to define the function of specific genes.

Experimental Protocols

Generation of the expression cassettes and viral vectors. The modified CMV (mCMV) promoter was made by PCR amplification of CMV by primers 5'-AAGGTACCAGATCT-TAGTTATTAATAGTAATCAATTACGG-3' (SEQ ID NO:1) and 5'-GAATCGATGCATGCCTCGAGACGGT-TCACTAAACCAGCTCTGC-3' (SEQ ID NO:2) with peG-FPN1 plasmid (purchased from Clontech, Inc) as template. The mCMV product was cloned into the KpnI and ClaI sites of the adenoviral shuttle vector pAd5KnpA, and was named pmCMVknpA. To construct the minimal polyA cassette, the oligonucleotides, 5'-CTAGAACTAGTAATAAAGGATC-CTTTATTTTCATTGGATCCGTGTGTTG-GTTTTTGTGTGCGGCCGCG-3' (SEQ ID NO:3) and 5'-TCGACGCGGCCGCACACAAAAACCAA-CACACGGATCCAATGAAAATAAAGGATC-CTTTATTACTAGTT-3' (SEQ ID NO:4), were used. The oligonucleotides contain SpeI and SalI sites at the 5' and 3' ends, respectively. The synthesized polyA cassette was ligated into SpeI, SalI digested pmCMVKnpA. The resultant shuttle plasmid, pmCMVmpA was used for construction of head-to-head 21 bp hairpins of eGFP (bp 418 to 438), human β-glucuronidase (bp 649 to 669), mouse β-glucuronidase (bp 646 to 666) or E. coli β-galactosidase (bp 1152-1172). The eGFP hairpins were also cloned into the Ad shuttle plasmid containing the commercially available CMV promoter and polyA cassette from SV40 large T antigen (pCMVsiGFPx). Shuttle plasmids were co-transfected into HEK293 cells along with the adenovirus backbones for generation of full-length Ad genomes. Viruses were harvested 6-10 days after transfection and amplified and purified as described (Anderson 2000).

Northern blotting. Total RNA was isolated from HEK293 cells transfected by plasmids or infected by adenoviruses using TRIZOL®Reagent (Invitrogen™ Life Technologies, Carlsbad, Calif.) according to the manufacturer's instruction. RNAs (30 µg) were separated by electrophoresis on 15% (wt/vol) polyacrylamide-urea gels to detect transcripts, or on 1% agarose-formaldehyde gel for target mRNAs analysis. RNAs were transferred by electroblotting onto hybond N+ membrane (Amersham Pharmacia Biotech). Blots were probed with $^{32}$P-labeled sense (5'-CACAAGCTGGAGTA-CAACTAC-3' (SEQ ID NO:5)) or antisense (5'-GTACTTG-TACTCCAGCTTTGTG-3' (SEQ ID NO:6)) oligonucleotides at 37° C. for 3 h for evaluation of siRNA transcripts, or probed for target mRNAs at 42° C. overnight. Blots were washed using standard methods and exposed to film overnight. In vitro studies were performed in triplicate with a minimum of two repeats.

In vivo studies and tissue analyses. Mice were injected into the tail vein (n=10 per group) or into the brain (n=6 per group) as described previously (Stein 1999) with the virus doses indicated. Animals were sacrificed at the noted times and tissues harvested and sections or tissue lysates evaluated for β-glucuronidase expression, eGFP fluorescence, or β-galactosidase activity using established methods (Xia 2001). Total RNA was harvested from transduced liver using the methods described above.

Cell Lines. PC12 tet off cell lines (Clontech Inc., Palo Alto, Calif.) were stably transfected with a tetracycline regulatable plasmid into which was cloned GFPQ19 or GFPQ80 (Chai 1999a). For GFP-Q80, clones were selected and clone 29 chosen for regulatable properties and inclusion formation. For GFP-Q19 clone 15 was selected for uniformity of GFP expression following gene expression induction. In all studies 1.5 µg/ml dox was used to repress transcription. All experiments were done in triplicate and were repeated 4 times.

Results and Discussion

Figure 1A:
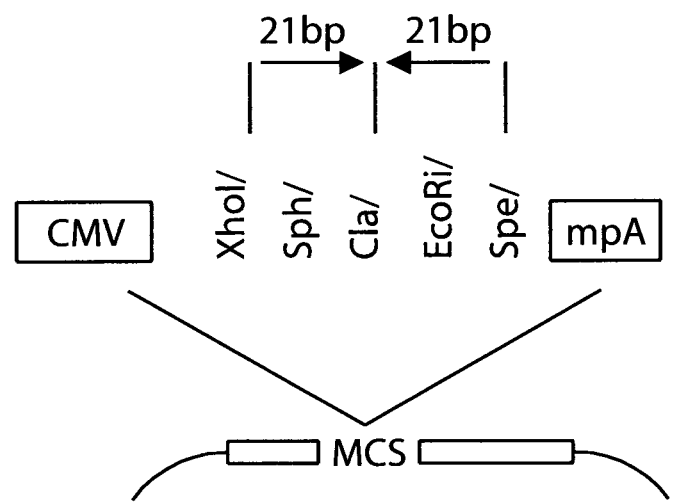
Figure 1B:
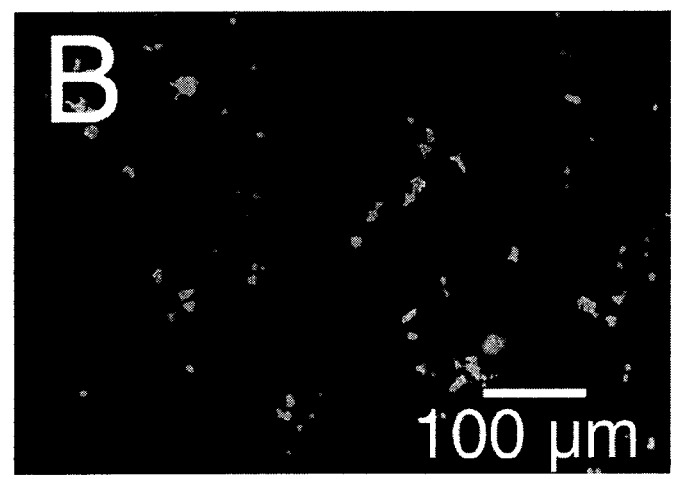
Figure 1C:
Figure 1D:
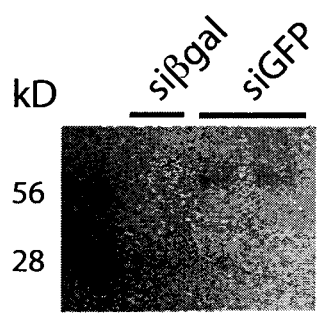
Figure 1E:
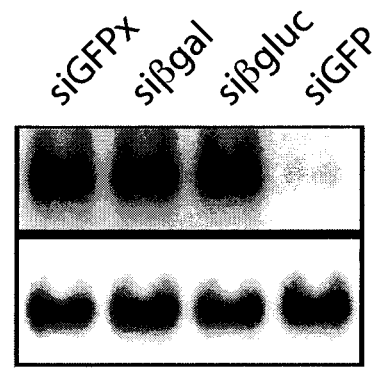

To accomplish intracellular expression of siRNA, a 21-bp hairpin representing sequences directed against eGFP was constructed, and its ability to reduce target gene expression in mammalian cells using two distinct constructs was tested. Initially, the siRNA hairpin targeted against eGFP was placed under the control of the CMV promoter and contained a full-length SV-40 polyadenylation (polyA) cassette (pCM-VsiGFPx). In the second construct, the hairpin was juxtaposed almost immediate to the CMV transcription start site (within 6 bp) and was followed by a synthetic, minimal polyA cassette (FIG. 1A, pmCMVsiGFPmpA) (Experimental Protocols), because we reasoned that functional siRNA would require minimal to no overhangs (Caplan 2001; Nykanen 2001). Co-transfection of pmCMVsiGFPmpA with pEG-FPN1 (Clontech Inc) into HEK293 cells markedly reduced eGFP fluorescence (FIG. 1C). pmCMVsiGFPmpA transfection led to the production of an approximately 63 bp RNA specific for eGFP (FIG. 1D), consistent with the predicted size of the siGFP hairpin-containing transcript. Reduction of target mRNA and eGFP protein expression was noted in pmCMVsiGFPmpA-transfected cells only (FIG. 1E, F). In contrast, eGFP RNA, protein and fluorescence levels remained unchanged in cells transfected with pEGFPN1 and pCMVsiGFPx (FIG. 1E, G), pEGFPN1 and pCMVsiβgluc-mpA (FIG. 1E, F, H), or pEGFPN1 and pCMVsiβgalmpA, the latter expressing siRNA against E. coli β-galactosidase (FIG. 1E). These data demonstrate the specificity of the expressed siRNAs.

Constructs identical to pmCMVsiGFPmpA except that a spacer of 9, 12 and 21 nucleotides was present between the transcription start site and the 21 bp hairpin were also tested. In each case, there was no silencing of eGFP expression (data not shown). Together the results indicate that the spacing of the hairpin immediate to the promoter can be important for functional target reduction, a fact supported by recent studies in MCF-7 cells (Brummelkamp 2002).

Figure 1I:
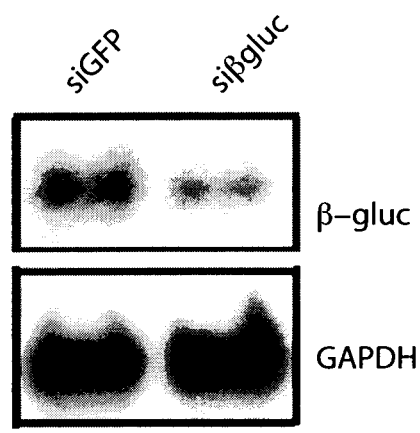
Figure 1J:
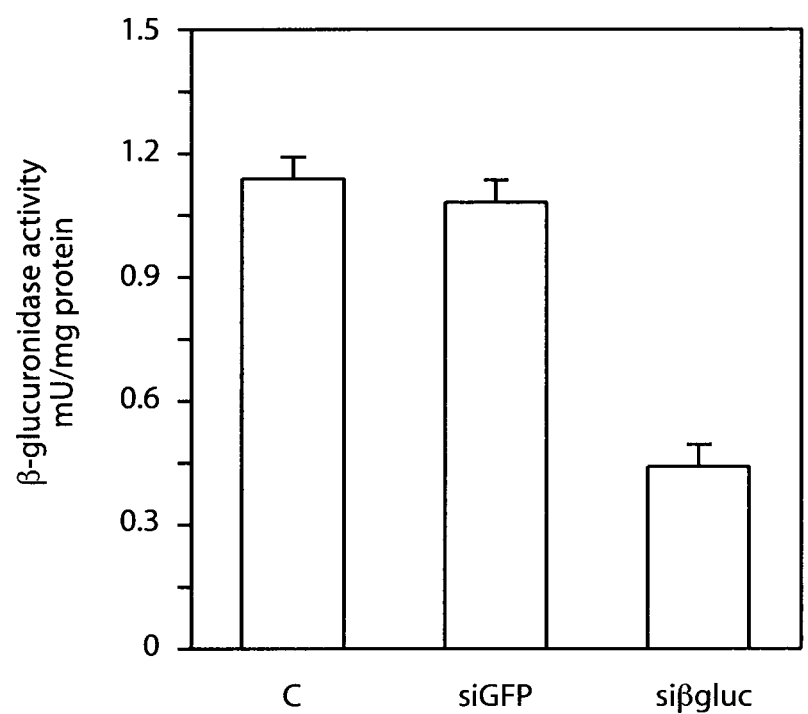

Recombinant adenoviruses were generated from the siGFP (pmCMVsiGFPmpA) and siβgluc (pmCMVsiβglucmpA) plasmids (Xia 2001; Anderson 2000) to test the hypothesis that virally expressed siRNA allows for diminished gene expression of endogenous targets in vitro and in vivo. HeLa cells are of human origin and contain moderate levels of the soluble lysosomal enzyme β-glucuronidase. Infection of HeLa cells with viruses expressing siβgluc caused a specific reduction in human β-glucuronidase mRNA (FIG. 1I) leading to a 60% decrease in β-glucuronidase activity relative to siGFP or control cells (FIG. 1J). Optimization of siRNA sequences using methods to refine target mRNA accessible sequences (Lee 2002) could improve further the diminution of β-glucuronidase transcript and protein levels.

The results in FIG. 1 are consistent with earlier work demonstrating the ability of synthetic 21-bp double stranded RNAs to reduce expression of target genes in mammalian cells following transfection, with the important difference that in the present studies the siRNA was synthesized intracellularly from readily available promoter constructs. The data support the utility of regulatable, tissue or cell-specific promoters for expression of siRNA when suitably modified for close juxtaposition of the hairpin to the transcriptional start site and inclusion of the minimal polyA sequence containing cassette (see, Methods above).

Figure 2A:
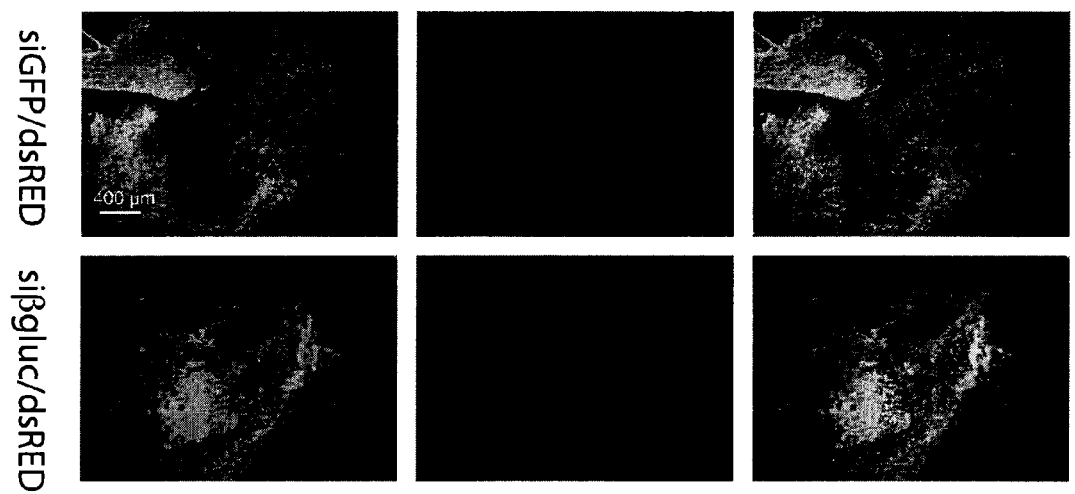
FIG. 2A-C. Viral vectors expressing siRNA reduce expression from transgenic and endogenous alleles in vivo. Recombinant adenovirus vectors were prepared from the siGFP and siβgluc shuttle plasmids described in FIG. 1. (A) Fluorescence microscopy reveals diminution of eGFP expression in vivo. In addition to the siRNA sequences in the E1 region of adenovirus, RFP expression cassettes in E3 facilitate localization of gene transfer. Representative photomicrographs of eGFP (left), RFP (middle), and merged images (right) of coronal sections from mice injected with adenoviruses expressing siGFP (top panels) or siβgluc (bottom panels) demonstrate siRNA specificity in eGFP transgenic mice striata after direct brain injection. (B) Full coronal brain sections (1 mm) harvested from AdsiGFP or Adsiβgluc injected mice were split into hemisections and both ipsilateral (il) and contralateral (cl) portions evaluated by western blot using antibodies to GFP. Actin was used as an internal control for each sample. (C) Tail vein injection of recombinant adenoviruses expressing siβgluc directed against mouse β-glucuronidase (AdsiMuβgluc) reduces endogenous β-glucuronidase RNA as determined by Northern blot in contrast to control-treated (Adsiβgal) mice.
Figure 2B:
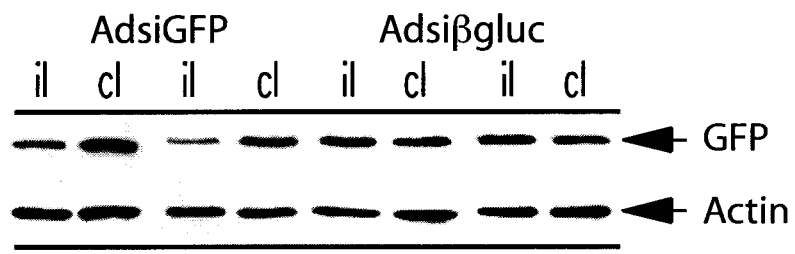

To evaluate the ability of virally expressed siRNA to diminish target-gene expression in adult mouse tissues in vivo, transgenic mice expressing eGFP (Okabe 1997) were injected into the striatal region of the brain with 1×10$^7$ infectious units of recombinant adenovirus vectors expressing siGFP or control siβgluc. Viruses also contained a dsRed expression cassette in a distant region of the virus for unequivocal localization of the injection site. Brain sections evaluated 5 days after injection by fluorescence (FIG. 2A) or western blot assay (FIG. 2B) demonstrated reduced eGFP expression. Decreased eGFP expression was confined to the injected hemisphere (FIG. 2B). The in vivo reduction is promising, particularly since transgenically expressed eGFP is a stable protein, making complete reduction in this short time frame unlikely. Moreover, evaluation of eGFP levels was done 5 days after injection, when inflammatory changes induced by the adenovirus vector likely enhance transgenic eGFP expression from the CMV enhancer (Ooboshi 1997).

Figure 2C:
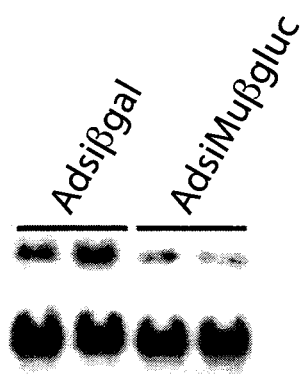

It was next tested whether virus mediated siRNA could decrease expression from endogenous alleles in vivo. Its ability to decrease β-glucuronidase activity in the murine liver, where endogenous levels of this relatively stable protein are high, was evaluated. Mice were injected via the tail vein with a construct expressing murine-specific siβgluc (AdsiMuβ-gluc), or the control viruses Adsiβgluc (specific for human β-glucuronidase) or Adsiβgal. Adenoviruses injected into the tail vein transduced hepatocytes as shown previously (Stein 1999). Liver tissue harvested 3 days later showed specific reduction of target β-glucuronidase RNA in AdsiMuβgluc treated mice only (FIG. 2C). Fluorometric enzyme assay of liver lysates confirmed these results, with a 12% decrease in activity from liver harvested from AdsiMuβgluc injected mice relative to Adsiβgal and Adsiβgluc treated ones (p<0.01; n=10). Interestingly, sequence differences between the murine and human siRNA constructs are limited, with 14 of 21 bp being identical. These results confirm the specificity of virus mediated siRNA, and indicate that allele-specific applications are possible. Together, the data are the first to demonstrate the utility of siRNA to diminish target gene expression in brain and liver tissue in vivo, and establish that allele-specific silencing in vivo is possible with siRNA.

Figure 3D:
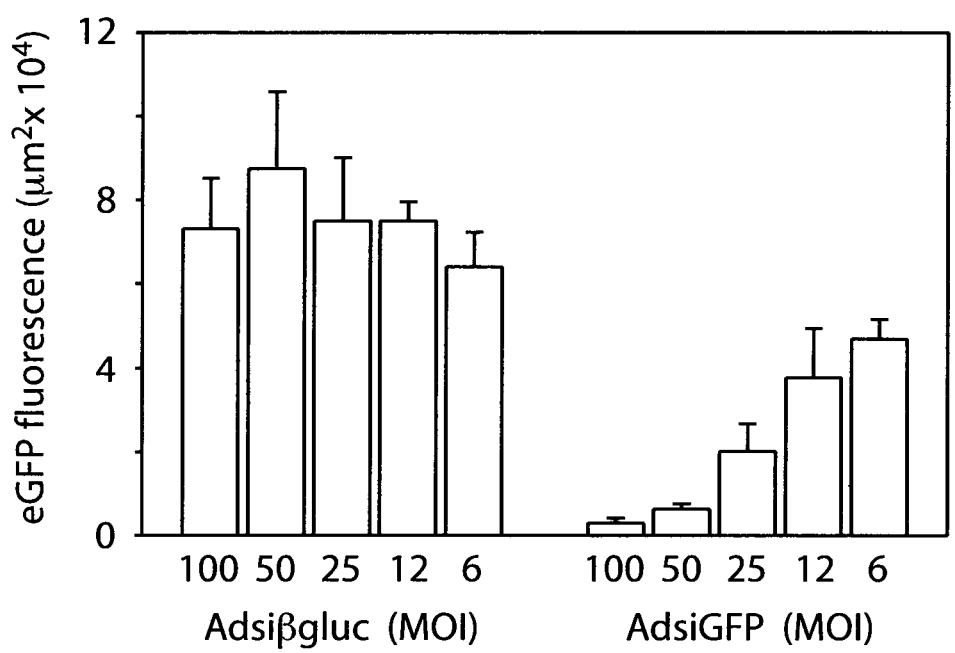

One powerful therapeutic application of siRNA is to reduce expression of toxic gene products in dominantly inherited diseases such as the polyglutamine (polyQ) neurodegenerative disorders (Margolis 2001). The molecular basis of polyQ diseases is a novel toxic property conferred upon the mutant protein by polyQ expansion. This toxic property is associated with disease protein aggregation. The ability of virally expressed siRNA to diminish expanded polyQ protein expression in neural PC-12 clonal cell lines was evaluated. Lines were developed that express tetracycline-repressible eGFP-polyglutamine fusion proteins with normal or expanded glutamine of 19 (eGFP-Q19) and 80 (eGFP-Q80) repeats, respectively. Differentiated, eGFP-Q19-expressing PC12 neural cells infected with recombinant adenovirus expressing siGFP demonstrated a specific and dose-dependent decrease in eGFP-Q19 fluorescence (FIG. 3A, C) and protein levels (FIG. 3B). Application of Adsiβgluc as a control had no effect (FIG. 3A-C). Quantitative image analysis of eGFP fluorescence demonstrated that siGFP reduced GFPQ19 expression by greater than 96% and 93% for 100 and 50 MOI respectively, relative to control siRNA (FIG. 3C). The multiplicity of infection (MOI) of 100 required to achieve maximal inhibition of eGFP-Q19 expression results largely from the inability of PC12 cells to be infected by adenovirus-based vectors. This barrier can be overcome using AAV- or lentivirus-based expression systems (Davidson 2000; Brooks 2002).

Figure 4A:
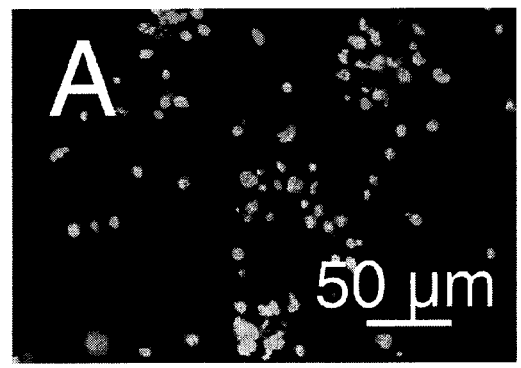
FIG. 4A-G. siRNA mediated reduction of expanded polyglutamine protein levels and intracellular aggregates. PC12 cells expressing tet-repressible eGFP-Q80 fusion proteins were washed to remove doxycycline and adenovirus vectors expressing siRNA were applied 3 days later. (A-D) Representative punctate eGFP fluorescence of aggregates in mock-infected cells (A), or those infected with 100 MOI of Adsiβ-gluc (B), AdsiGFPx (C) or Adsiβgal (D). (E) Three days after infection of dox-free eGFP-Q80 PC12 cells with AdsiGFP, aggregate size and number are notably reduced. (F) Western blot analysis of eGFP-Q80 aggregates (arrowhead) and monomer (arrow) following Adsiβgluc or AdsiGFP infection at the indicated MOIs demonstrates dose dependent siGFP-mediated reduction of GFP-Q80 protein levels. (G) Quantification of the total area of fluorescent inclusions measured in 4 independent fields/well 3 days after virus was applied at the indicated MOIs. The data are mean±standard deviation.
Figure 4B:
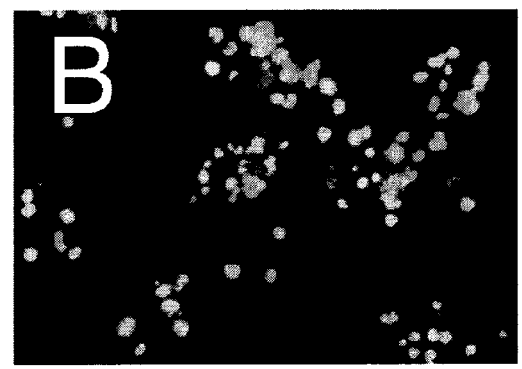
Figure 4C:
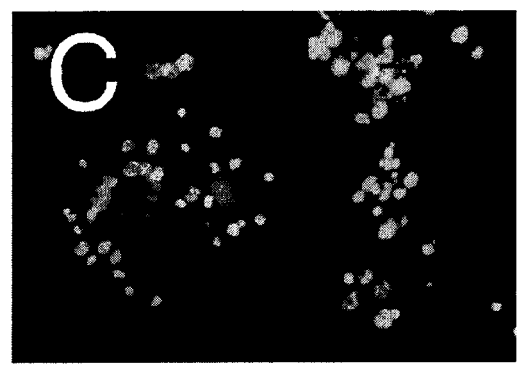
Figure 4D:
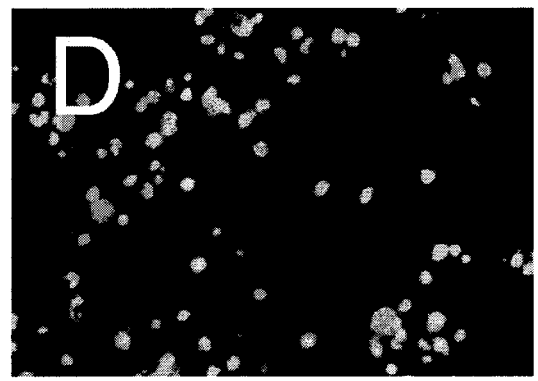
Figure 4E:
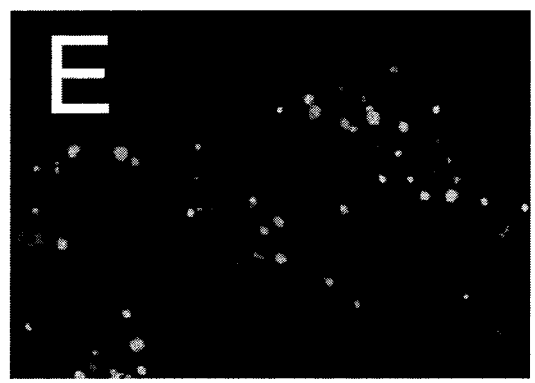
Figure 4F:
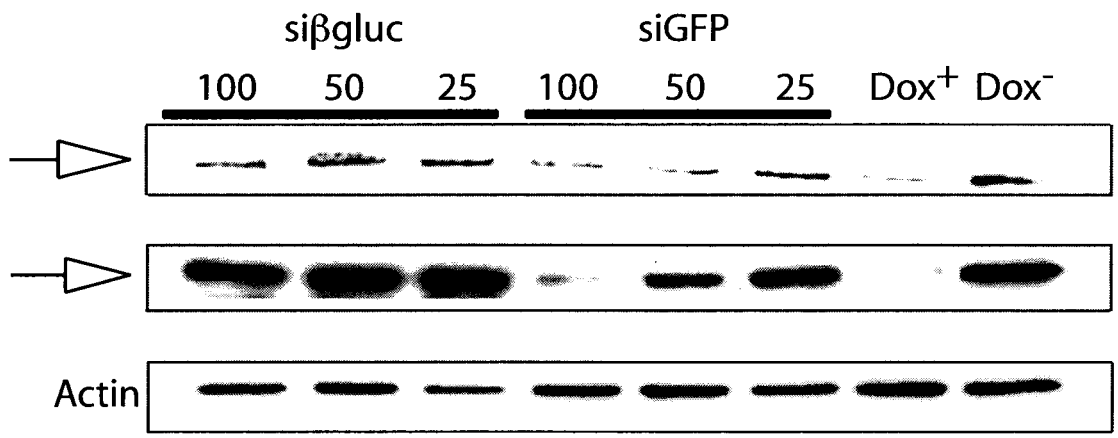
Figure 4G:
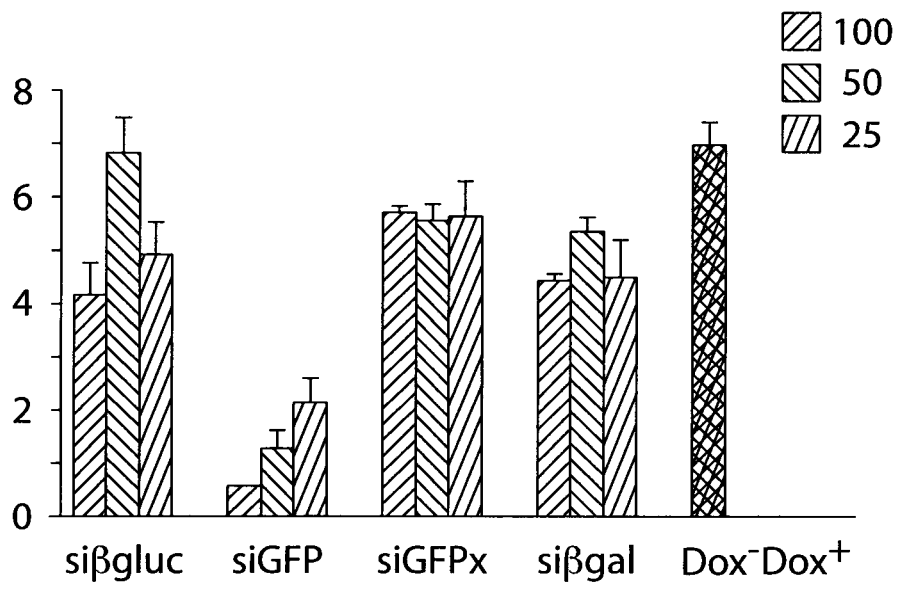

To test the impact of siRNA on the size and number of aggregates formed in eGFP-Q80 expressing cells, differentiated PC-12/eGFP-Q80 neural cells were infected with AdsiGFP or Adsiβgluc 3 days after doxycycline removal to induce GFP-Q80 expression. Cells were evaluated 3 days later. In mock-infected control cells (FIG. 4A), aggregates were very large 6 days after induction as reported by others (Chai 1999a; Moulder 1999). Large aggregates were also seen in cells infected with Adsiβgluc (FIG. 4B), AdsiGFPx, (FIG. 4C, siRNA expressed from the normal CMV promoter and containing the SV40 large T antigen polyadenylation cassette), or Adsiβgal (FIG. 4D). In contrast, polyQ aggregate formation was significantly reduced in AdsiGFP infected cells (FIG. 4E), with fewer and smaller inclusions and more diffuse eGFP fluorescence. AdsiGFP-mediated reduction in aggregated and monomeric GFP-Q80 was verified by Western blot analysis (FIG. 4F), and quantitation of cellular fluorescence (FIG. 4G). AdsiGFP caused a dramatic and specific, dose-dependent reduction in eGFP-Q80 expression (FIG. 4F, G).

It was found that transcripts expressed from the modified CMV promoter and containing the minimal polyA cassette were capable of reducing gene expression in both plasmid and viral vector systems (FIGS. 1-4). The placement of the hairpin immediate to the transcription start site and use of the minimal polyadenylation cassette was of critical importance. In plants and *Drosophila*, RNA interference is initiated by the ATP-dependent, processive cleavage of long dsRNA into 21-25 bp double-stranded siRNA, followed by incorporation of siRNA into a RNA-induced silencing complex that recognizes and cleaves the target (Nykanen 2001; Zamore 2000; Bernstein 2001; Hamilton 1999; Hammond 2000). Viral vectors expressing siRNA are useful in determining if similar mechanisms are involved in target RNA cleavage in mammalian cells in vivo.

In summary, these data demonstrate that siRNA expressed from viral vectors in vitro and in vivo specifically reduce expression of stably expressed plasmids in cells, and endogenous transgenic targets in mice. Importantly, the application of virally expressed siRNA to various target alleles in different cells and tissues in vitro and in vivo was demonstrated. Finally, the results show that it is possible to reduce polyglutamine protein levels in neurons, which is the cause of at least nine inherited neurodegenerative diseases, with a corresponding decrease in disease protein aggregation. The ability of viral vectors based on adeno-associated virus (Davidson 2000) and lentiviruses (Brooks 2002) to efficiently transduce cells in the CNS, coupled with the effectiveness of virally-expressed siRNA demonstrated here, extends the application of siRNA to viral-based therapies and to basic research, including inhibiting novel ESTs to define gene function.

EXAMPLE 2 siRNA Specific for Huntingtin's Disease

The present inventors have developed huntingtin siRNA focused on two targets. One is non-allele specific (siH-Dexon2), the other is targeted to the exon 58 codon deletion, the only known common intragenic polymorphism in linkage dysequilibirum with the disease mutation (Ambrose et al, 1994). Specifically, 92% of wild type huntingtin alleles have four GAGs in exon 58, while 38% of HD patients have 3 GAGs in exon 58. To assess a siRNA targeted to the intragenic polymorphism, PC6-3 cells were transfected with a full-length huntingtin containing the exon 58 deletion. Specifically, PC6-3 rat pheochromocytoma cells were co-transfected with CMV-human Htt (37Qs) and U6 siRNA hairpin plasmids. Cell extracts were harvested 24 hours later and western blots were performed using 15 μg total protein extract. Primary antibody was an anti-huntingtin monoclonal antibody (MAB2166, Chemicon) that reacts with human, monkey, rat and mouse Htt proteins.

Figure 5A:
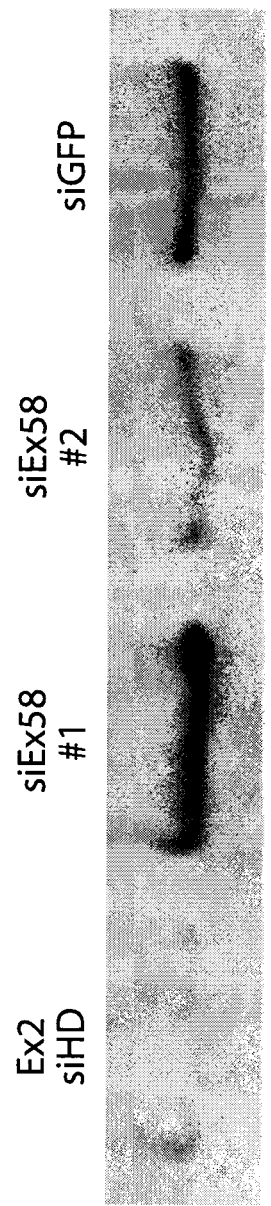
FIG. 5A-B. (A) Allele-specific silencing of mutant huntingtin by siRNA. PC6-3 cells were co-transfected with plasmids expressing siRNA specific for the polymorphism encoding the transcript for mutant huntingtin. (B) The original target for testing hairpins with putative specificity for the 3 GAG-repeat disease linked polymorphism, shEx58.1 and shEx58.2. In this preliminary test, shEx58.1 is best.
Figure 5B:
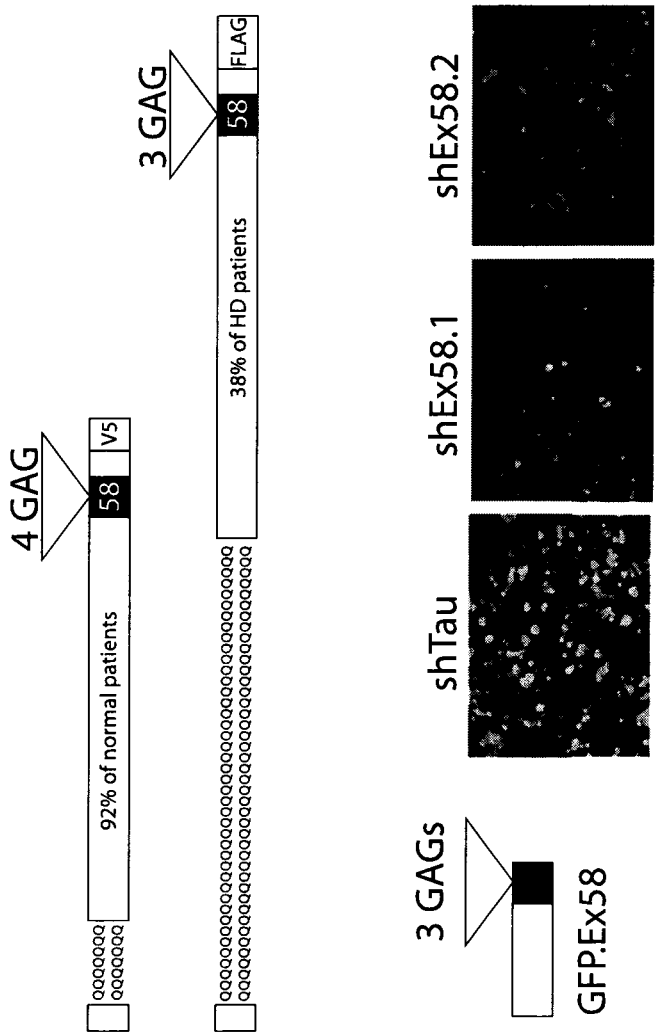

As seen in FIG. 5, the siRNA lead to silencing of the disease allele. As a positive control, a non-allele specific siRNA targeted to exon 2 of the huntingtin gene was used. siRNA directed against GFP was used as a negative control. It was noted that siEx58# 2 functional. The sequence for siEX58#2 is the following: 5'-AAGAGGAGGAGGC-CGACGCCC-3' (SEQ ID NO:17). siEX58#1 was only minimally functional.

EXAMPLE 3 siRNA Specific for SCA1

Spinocerebellar ataxia type 1 (SCA1) is a dominantly inherited, progressive neurodegenerative disease caused by an expanded polyglutamine tract in ataxin-1. SCA1 is one of at least nine neurodegenerative diseases caused by polyglutamine expansion, which includes Huntington's disease (HD) and several other ataxias (Orr 1993, Zoghbi 1995). SCA1 is characterized by progressive ataxia, cerebellar atrophy, and loss of cerebellar Purkinje cells and brainstem neurons. A feature common to all polyglutamine diseases, is the formation of intracellular aggregates containing the disease protein, molecular chaperones, and components of the ubiquitin-proteasome pathway (Orr 1993, Zoghbi 1995). In SCA1, as in many other polyQ diseases, the inclusions are intranuclear (Skinner 1997).

Disease allele expansion ranges from 44 to 82 glutamines in SCA1, with repeat length inversely correlated to age of disease onset (Zoghbi 1995). Work in *Drosophila* models and transgenic mice demonstrate that the expansion confers a toxic gain of function on ataxin-1 (Fernandez-Funez 2000, Burright 1995, Klement 1998). Recent work has also shown that phosphorylation of serine 776 of ataxin-1 by AKT, but not nuclear aggregation, is required for SCA1 pathogenesis (Emamian 2003, Chen 2003). Together, work in these model organisms has identified manipulation of molecular chaperones, or inhibition of AKT phosphorylation of ataxin-1, as potential therapeutic routes (Fernandez-Funez 2000, Emamian 2003, Cummings 1998). As yet, however, there is no effective therapy for SCA1 or the other dominant neurodegenerative diseases caused by polyglutamine expansion.

Inhibition of mutant allele expression provides a direct approach to SCA1 therapy. In past years, antisense- or ribozyme-based techniques held promise in culture systems, but proved difficult to translate to animal models. More recently, gene silencing through RNA interference (RNAi) has emerged as a powerful method to reduce target gene expression in cell culture and, importantly, in brain (Caplen 2002, Miller 2003, Xia 2002, Davidson 2004). In the present experiments, the inventors tested whether the introduction of viral vectors expressing short hairpin RNAs (shRNAs) directed against the transgenic human mutant ataxin-1 gene would reduce pathology and ataxia in a mouse SCA1 model.

Vector construction and in vitro screening. Different target sites (F1 to F11) were made based on the 2.4 kb human ataxin-1 ORF (gene accession number: X79204). Sites were as follows: F1, by 144-64; F2 bp 576-96; F3, by 679-99; F4, 1334-54; F5, by 490-510; F6, by 2250-70; F7, by 18-38; F8, by 863-82; F9, by 1876-96; F10, bp 574-94; F11, by 670-90. *E. coli* β-galactosidase (bp 1152-1172) was used as control shRNA. Hairpins with loops 5'-ACTAGT-3' (SEQ ID NO:15), or 5'-CTTCCTGTCA-3' (SEQ ID NO:16) from mir23, were cloned into vectors containing the human U6 promoter, or the modified CMV promoter, by a two-step method as previously described (Xia 2002).

Flag-tagged ataxin-1 with normal (30Q) or expanded (82Q) polyglutamine regions were cloned into the AAV shuttle plasmid for testing hairpin silencing. Plasmids expressing hairpins and plasmids expressing ataxin-1 were co-transfected into HEK 293 cells or PC6-3 cells (4:1 ratio, hairpin to target), and cells lysed 48 to 72 h later. Western blots with anti-Flag were done to assess ataxin-1 levels. Actin was used a loading control.

Quantitative RT-PCR. HEK293 cells were transfected (Lipofectamine-2000, Invitrogen) with shLacZ, shScaI.F10 (571-592, ScaI—shSCA1.F10, 5'-GGACACAAGGCT-GAGCAGCAG-3' (SEQ ID NO:13)), or shScaI.F11 (595-615, HScaI—shSCA1.F11, 5'-CAGCAGCACCTCAG-CAGGGCTGCAGGATTAGTCAACCACCTCAGCAGGG CT-3' (SEQ ID NO:14)) and a human Seal expression plasmid in 2:1, 4:1, or 8:1 molar ratios of shRNA:ScaI. RNA was harvested 24 hours post-transfection using Trizol reagent (Invitrogen). Following DNase treatment (DNA-free, Ambion), random-primed, first-strand cDNA was generated from 1 μg total RNA (Taqman Reverse Transcription Reagents, Applied Biosystems) according to the manufacturer's protocol. cDNA was diluted four-fold and then used as template for real-time PCR. Taqman Assays were performed on an ABI Prism 7000 Sequence Detection System using Taqman 2× Universal PCR Master Mix (Applied Biosystems) and Applied Biosystems Assays-on-Demand Taqman primers/probe sets specific for human Seal and mammalian rRNA. Relative gene expression was determined using the relative standard curve method (Applied Biosystems User Bulletin #2). Human Seal expression levels were normalized to rRNA levels and all samples were calibrated to the shLacZ 8:1 sample.

AAV vectors. pAAVshLacZ and pAAVshSCA1 contain human U6 driven hairpins and CMV-hrGFP-SV40 polyA expression cassettes cloned between two AAV2 ITR sequences. Flanking the AAV provirus are left and right arm sequences from the Baculovirus *Autographa californica*, which are used to generate recombinant Bacmid DNA through homologous recombination in *E. coli*. Recombinant Baculovirus were generated as described in the Bac-to-Bac Baculovirus Expression System (InVitrogen), and AAV virus was purified as described in Urabe et al (Urabe 2002). AAV titers were determined by DNA slot blot using an hrGFP-specific radiolabeled probe.

AAV injections. Injections into cerebella were as described by Alisky et al. (Alisky 2000), except that injections were administered 1 mm lateral to the midline, with a total of 3 μl injected into three separate sites. Transduction was targeted to midline lobules IV/V, with transduction spreading anterior-posterior to lobules III and VI, respectively. Virus titers were $\sim 1 \times 10^{12}$ vector genomes/ml as assessed by Q-PCR.

Northern Analysis. Total RNA was isolated using TRI-ZOL® Reagent (InVitrogen™ Life Technologies, Carlsbad, Calif.) according to the manufacturer's instructions. RNAs (30 μg) were separated by electrophoresis on 15% (wt/vol) polyacrylamide-urea gels to detect transcripts. RNAs were transferred by electroblotting onto Hybond N+ membranes (Amersham Pharmacia Biotech). Blots were probed with $^{32}$P-labeled sense oligonucleotides at 36° C. for 3 h for evaluation of transcripts. Blots were washed in 2×SSC twice for 15 min at 36° C. and exposed to film overnight (Miyagishi 2002).

Immunohistochemistry and quantitation. Mice were perfused and fixed overnight with 4% paraformaldehyde in 0.2M phosphate buffer (pH 7.4). Tissues were cryoprotected by immersion in 25% sucrose and frozen in O.C.T. compound (Sakura Finetek U.S.A. Inc, Torrance, Calif.). Sagittal cryostat sections (10 μm) were cut and mounted onto gelatin-coated slides. For calbindin staining, no unmasking procedure was used. Ataxin-1 staining was done as described (Skinner 1997). Sections were analyzed using a Leica DM RBE and images acquired with a SPOT RT camera and associated software (Diagnostics Instruments, Sterling Heights, Mich.). Measurement of molecular layer thickness and quantitation of Purkinje cells were done using BioQuant system software (R & M Biometrics, Nashville, Tenn.) (Williams 1988).

Rotarod analysis. The Rotarod (Ugo Basile Biological Research Apparatus, model 7650) was used for these studies. Five-week-old mice were habituated on the rotarod for 4 min, and then tested for 4 consecutive days, 4 trials per day (~30 minutes rest between trial). Mice were retested two weeks after intracerebellar injection, and every two weeks until sacrifice at 16 wks. Additional groups of animals were tested out to 20 weeks. For each trial, the rod was accelerated from 4 to 40 rpm over 5 min, then maintained at 40 rpm until trial completion. Latency to fall (or if they hung on or rotated for two consecutive rotations without running) was recorded for each mouse. Any mouse remaining on the apparatus for 500 sec. was removed and scored as 500 sec.

Results

Optimization of Ataxin-1-Targeting shRNAs

Figure 6A:
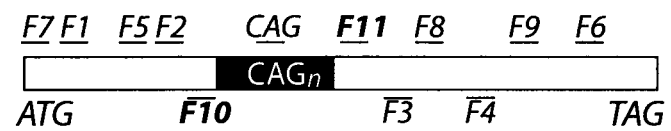
FIG. 6A-F. Silencing ataxin-1. (A) Cartoon of the ataxin-1 cDNA and regions tested for silencing (lines). The CAG repeat region is indicated. The most effective hairpins identified, F10 and F11, are bolded. (B) Screening of shSCA1s for ataxin-1 silencing. HEK 293 cells were transfected with shRNA- and ataxin-1-expressing plasmids (4:1 ratio), and FLAG-tagged ataxin-1 (ataxin-1FLAG) expression was screened by western blot two days later. Actin was used as a loading control. ShLacZ was included as a negative hairpin control. Data shown are from U6-expressed shRNAs. (C) Dose dependent decline in hSCA-1 mRNA as assessed by Q-RTPCR. HEK 293 cells were transfected with shRNA- and ataxin-1-expressing plasmids at the ratios indicated, and RNA isolated 24 hrs later. RNA levels were measured by Q-PCR as described in the methods. (D) Comparison of mCMV- and U6-expressed shRNAs in neuronal cells. PC6-3 cells were transfected with plasmids expressing the indicated shRNAs, and expression of ataxin assessed 2 days later by western blot. shCAG was targeted to the CAG repeat region and was used as a positive control for silencing (E) The loop from miR23 improves silencing from the hU6 promoter. HEK 293 cells were transfected with plasmids expressing the indicated hairpins and ataxin-1FLAG, and silencing evaluated 2 days later by western blot. The loop improves silencing of shSCA1.F10 and shSCA1.F11. (F) shSCA1.F10 and shSCA1.F11 silence mutant (Q82) ataxin-1. HEK 293 cells were transfected with plasmids expressing the indicated hairpins, and a plasmid expressing human ataxin-1 with an expanded poly(Q) tract (FLAG-tagged). Silencing of the human mutant ataxin-1 was assessed by western blot 2 days later.
Figure 6B:
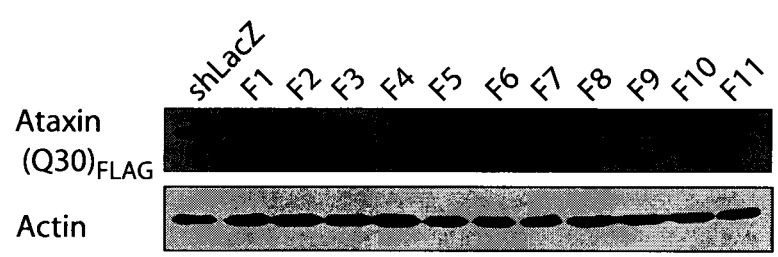
Figure 6C:
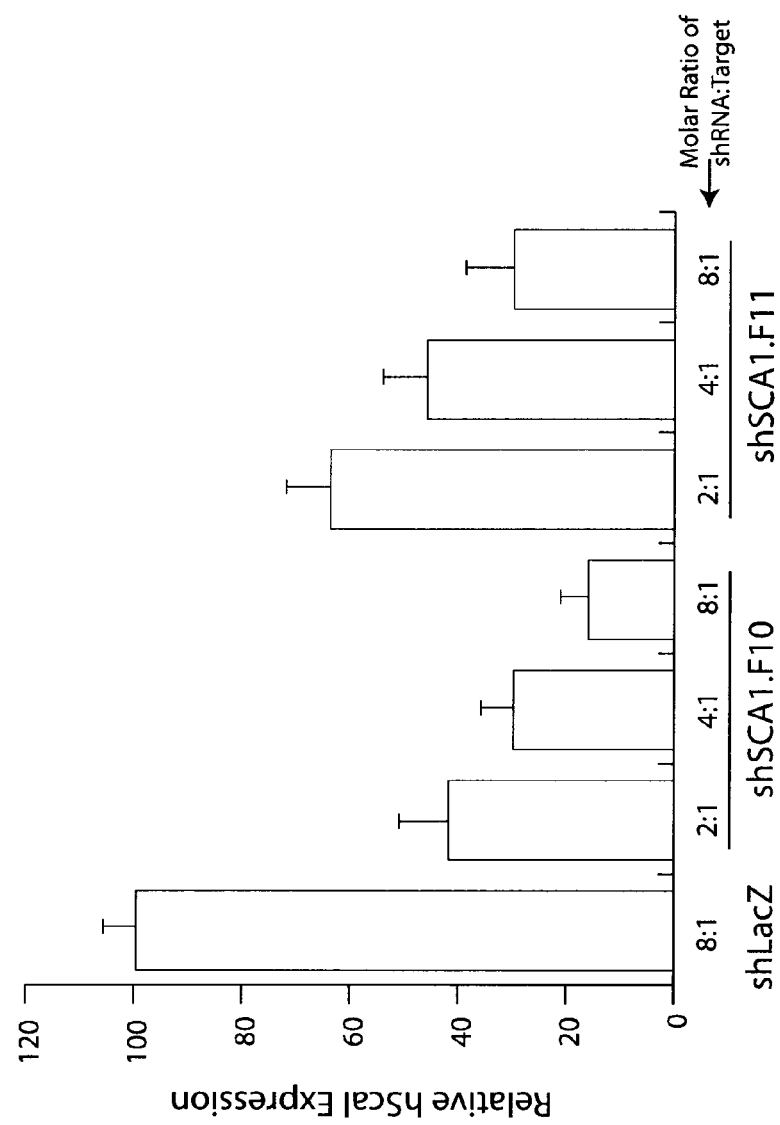
Figure 6D:
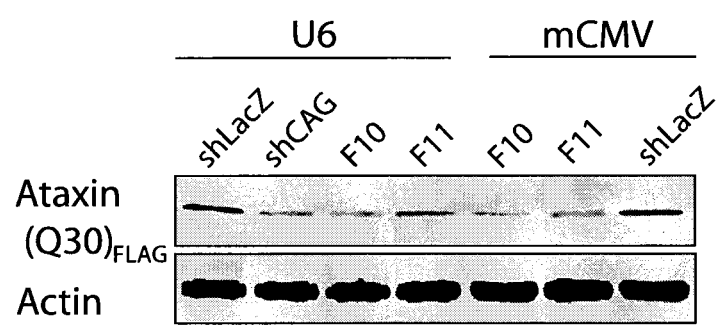

To accomplish RNAi for ataxin-1, the inventors developed short hairpins (shRNA) directed to the human 2.4 kb ataxin-1 cDNA for primary screening in vitro. Short hairpin RNA (shRNA)-expressing plasmids were co-transfected into HEK 293 cells with ataxin-1 (FLAG-tagged) expression plasmids. Candidate hairpin sequences expressed from pol III (human U6; hU6) and pol II (modified CMV; mCMV) (Xia 2002) promoters were tested. The initial screen of hairpins directed against ataxin-1 sequences dispersed along the ataxin-1 cDNA (FIG. 6A) was unsuccessful regardless of promoter (0 of 4 tested). An expanded evaluation identified two constructs (shSCA1.F10 and shSCA1.F11; 2 of 7 tested) that reduced RNA levels up to 80% and ataxin-1 protein levels by 50-60% (FIG. 6B, 6C). Q-PCR analysis showed that shSCA1.F10- and shSCA1.F11-mediated silencing of the ataxin-1 transcript was dose dependent (FIG. 6C). To determine if shSCA1s were functional in neural cells the inventors used PC6-3 cells, a PC-12 cell derivative that displays more uniform neuronal phenotypes (Pittman 1993). PC6-3 cells were transfected with AAV shuttle vectors expressing shSCA1.F10, shSCA1.F11, or control shRNAs, and silencing of ataxin-1 expression was assessed by western blot. Interestingly, mCMV-expressed shSCA1.F11 appeared more efficient than the same construct expressed from the hU6 promoter (FIG. 6D).

Figure 6E:
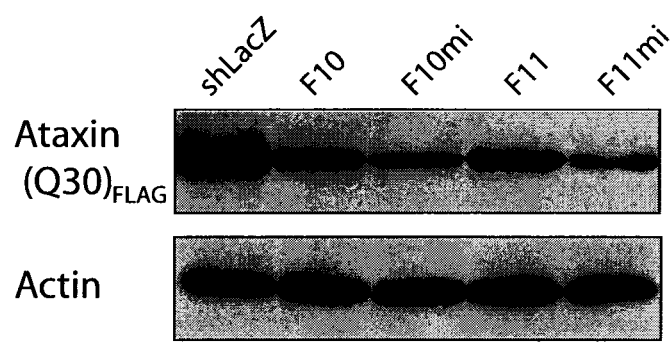
Figure 6F:
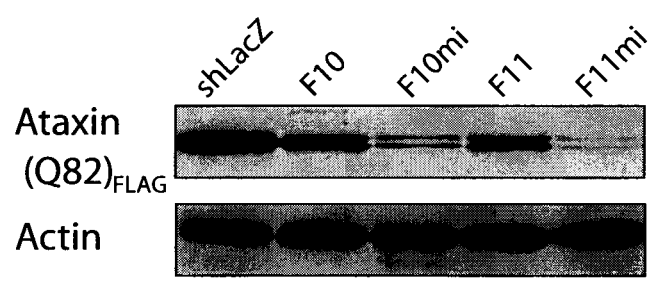

A recent study by Kawasaki and colleagues (Kawasaki 2003) suggested that one caveat of Pol III-based promoters for expressing shRNAs is inefficient export of transcripts to the cytoplasm. Replacement of the loop structure of their shRNAs with those derived from endogenously expressed miRNAs improved nuclear export and gene silencing (Kawasaki 2003). To test if similar modifications improved Pol III-directed expression of shRNAs for ataxin-1 silencing, the loops of hairpins from shSCA1.F10 and shSCA1.F11, (originally 5'-ACTAGT-3' (SEQ ID NO:15)), were replaced with the loop from miR23 (5'-CTTCCTGTCA-3' (SEQ ID NO:16); designated F10 ml). While there was no effect of the miRNA loop on CMV-shRNA-based silencing (not shown), miR23 loops improved the silencing activity of Pol III-expressed shSCA1.F10 and shSCA1.F11 against normal human ataxin-1 (FIG. 6E) and importantly, human ataxin-1 with an 82Q expansion (FIG. 6F).

Effects of shSCA1 on Motor Coordination in SCA1 Transgenic Mice

Figure 7A:
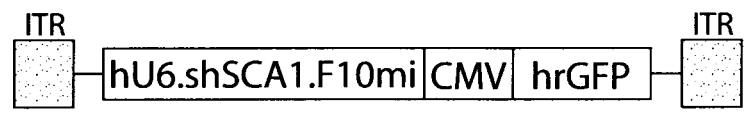
FIG. 7A-D. AAV vectors for shRNA expression in vivo. (A) Cartoon of AAV construct. The construct for shSCA.F11mi and shLacZ expression was similar except that shSCA1.F10mi was replaced with shSCA.F11mi or shLacZ sequences, respectively. Note that the hrGFP expression cassette is distinct from the shRNA expression cassette. (B) AAVshSCA1 with hrGFP reporter leads to extensive transduction of cerebellar Purkinje cells (Purkinje cell layer denoted by arrowheads). Wildtype mice were injected with AAVshSCA1.F10mi (left panel) or injected with saline (right panel) and sacrificed 3 weeks later to evaluate eGFP expression. g, granule cell layer; m, molecular layer. Bar=100 µm. (C) shSCA1 and shLacZ transcripts are expressed in vivo. Wildtype mice were injected with AAVshLacZ or AAVshSCA1.F10mi, and RNA isolated from cerebella 10 days later. Northern blots were probed with $^{32}$P-labeled oligonucleotides specific for the antisense strand of the hairpin. L, RNA ladder; (sizes indicated at left). Lanes, 2 and 3, RNA from AAVshSCA1.F10mi and AAVshLacZ transduced brains, respectively. The arrowhead denotes the unprocessed transcript, the arrow the processed siRNA. (D) Rotarod performance of wildtype (triangles) and SCA1 (squares) mice treated with shRNA-expressing AAV1s or mock infected, as indicated in the legend. Mice were injected with virus or saline at age 7 weeks and re-tested every two weeks (weeks 5, 11, 15, and 21 are shown). From weeks 11-21 significant differences in performance between AAVshSCA1 and AAVshLacZ treated SCA1 mice were noted (P<0.001). There were no significant differences between wildtype mice treated with shLacZ (not shown), shSCA1.F10mi or saline. For week 5, n=10 and 11 for shSCA1 and shLacZ treated SCA1 mice, respectively; n=6 and 5 for shSCA1 and control treated age-matched wildtype littermates, respectively. For weeks 7-21, n=14 and 12 for shSCA1 and shLacZ treated SCA1 mice, respectively; n=12 and 11 for shSCA1 and control treated age-matched wildtype littermates, respectively.
Figure 7B:
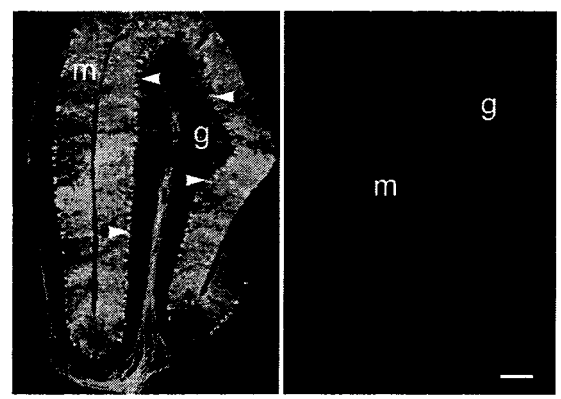
Figure 7C:
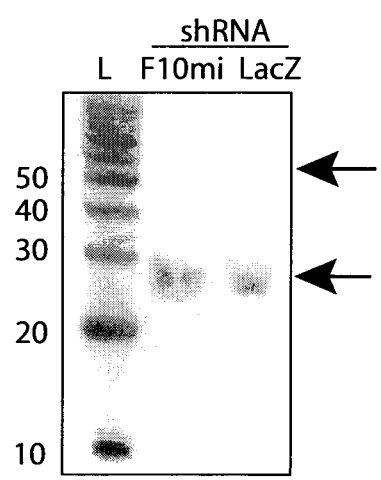

The inventors next generated recombinant adeno-associated virus serotype 1 (AAV1) expressing shSCA1.F10mi and shSCA1.F11mi to evaluate hairpin efficacy in the transgenic mouse model of SCA1 (denoted AAVshSCA1.F10mi or AAVshSCA1.F11mi). The virus was also engineered to express the hrGFP reporter for detection of transduced cells (FIG. 7A). In SCA1 mice, transgenic human disease allele (ataxin-1-Q82) expression is confined to the cerebellar Purkinje cells by PCP-2, a Purkinje cell-specific promoter (Burright 1995, Clark 1997). Thus the inventors initially tested AAV1's ability to transduce Purkinje cells, since its transduction profile in cerebella was unknown. As shown in FIG. 7B, AAVshSCA1 readily transduces Purkinje cells. Northern blot of RNA harvested from cerebella 10 days after viral injection also showed that shRNAs are expressed in vivo (FIG. 7C). The fast expression kinetics from AAV1 is similar to AAV serotype 5, which also shows tropism for Purkinje cells (Alisky 2000).

Figure 7D:
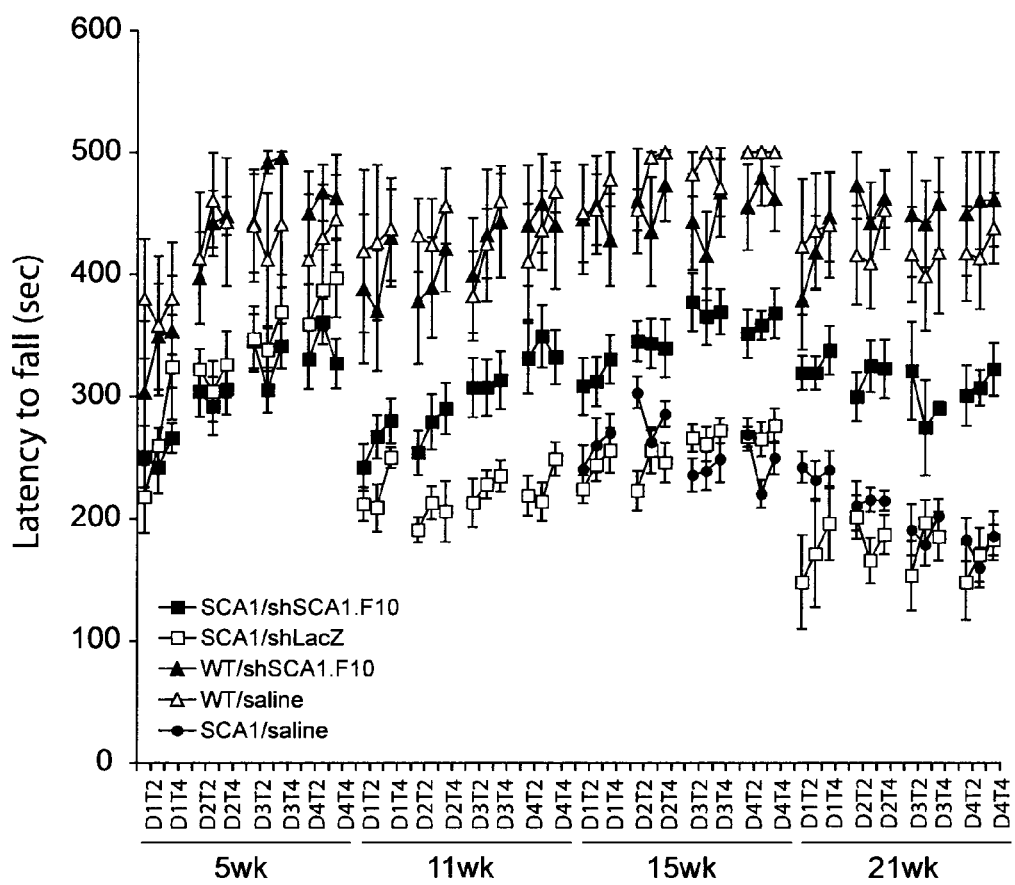

Heterozygous SCA1 transgenic mice display many of the characteristics of human SCA1, including progressive ataxia, Purkinje cell degeneration, and thinning of cerebellar molecular layers. The rotarod test for motor performance is a valid indicator of the progressive ataxia; proper foot placement in response to a changing environment (i.e., the rotating rod) challenges the cerebellum. To determine the effects of AAVshSCA1, or AAVs expressing control hairpins (AAVshLacZ), on the ataxic phenotype, mice were analyzed for baseline rotarod performance, followed by injection at 7 weeks of age with shRNA-expressing viruses into midline cerebellar lobules. Rotorod analyses were repeated every two weeks until sacrifice. Mock-transduced animals (saline injection) were also assessed. The data in FIG. 7D demonstrate that transduction with viruses expressing shSCA1.F10mi, but not shLacZ, significantly improves SCA1 mice motor performance. Also of note is the observation that expression of shSCA1.F10mi did not negatively affect the rotarod performance of wildtype mice, indicating that intracellular expression of shRNAs is not overtly toxic to Purkinje cells.

Improved Neuropathology in shSCA1-Expressing Purkinje Cells

The inventors next tested if the improved rotarod performance was attributable to improvements in neuropathology. The progressive pathological changes in SCA1 transgenic mice have been well characterized, and include intranuclear inclusions of ataxin-1, Purkinje cell dendritic pruning, Purkinje cell loss and concomitant thinning of the cerebellar molecular layer (Burright 1995).

Cerebellar lobules from SCA1 and wildtype mice injected with AAVshLacZ or AAVshSCA1 were evaluated for hrGFP expression and calbindin staining to assess if shSCA1 reduced the progressive thinning of the molecular layer in SCA1 transgenic mice. FIG. 8A shows representative sections from virus-injected mice cerebella. The juxtaposition of untransduced regions (hrGFP−) to transduced ones (hrGFP+) allowed for direct comparisons of the effects of shSCA1. Calbindin staining remained robust in hrGFP+ molecular layers from SCA1 transgenic mice treated with AAVshSCA1, but was notably diminished in untransduced areas. HrGFP+ molecular layers from SCA1 transgenic mice injected with AAVshLacZ showed reduced calbindin staining, indistinguishable from untransduced layers. In wildtype mice injected with AAVshSCA1 (FIG. 8A), AAVshLacZ or saline (not shown), calbindin staining was uniform in all regions examined. The data show that shSCA1-mediated improvements are confined to transduced neurons.

Molecular layer widths were quantified in wildtype mice and SCA1 transgenic mice treated with AAV. FIG. 8B confirms the morphological observation that expression of shRNAs did not affect the molecular layers of wildtype mice. The data also show that molecular layer widths in hrGFP+ regions from shSCA1-treated SCA1 mice (162 µm±16) are indistinguishable from wildtype controls (untransduced, 158 µm±20; AAVshSCA1 treated, 156 µm±20), in contrast to the markedly thinned molecular layer in SCA1 mice given AAVshLacZ (109 µm±12), or mock injected (109 µm±11).

The inventors next determined the effects of AAVshSCA1 on human ataxin-1 expression and the formation of ataxin-1 nuclear inclusions. In cerebella from SCA1 mice harvested 1 week after injection of AAVshSCA1.F10 or AAVshSCA1.F11, ataxin-1 immuno-reactivity was markedly reduced in transduced (hrGFP+) relative to non-transduced (GFP−) cells (FIG. 9). There was no effect of transduction on ataxin-1 levels in mock or AAVshLacZ treated SCA1 mice.

Prior work in the Orr and Zoghbi laboratories (Clark 1997) established that mutant ataxin-1 forms single intranuclear inclusions in ~50% of Purkinje cells at 16 weeks of age. In tissues from SCA1 mice harvested 9 weeks after injection of saline or AAVshLacZ, ataxin-1 immunofluorescence (IF) was robust and present throughout Purkinje cell nuclei. The inventors found punctate intranuclear inclusions in 49% of cells (FIG. 10A left panels; FIG. 10B top panel), independent of their transduction status. In contrast, transduced (hrGFP+) cells from AAVshSCA1 treated mice displayed greatly diminished ataxin-1 nuclear staining, with complete resolution of inclusions in transduced cells (FIGS. 10A, 10B and FIG. 11).

Discussion

The present results demonstrate in vivo efficacy of RNAi and support the utility of RNAi gene therapy for SCA1 and other polyglutamine neurodegenerative diseases. In the SCA1 mouse model, cerebellar delivery of AAV1 vectors expressing ataxin-1-targeting shRNAs reduced ataxin-1 expression in Purkinje cells, improved motor performance and normalized the cerebellar pathology in transduced regions. In these studies, the inventors directed delivery to midline cerebellar lobules because of their importance in axial and gait coordination in mammals. In tissues harvested 9 weeks after injection, the inventors found near 100% transduction of targeted lobules, with a transduction efficiency of 5-10% of all cerebellar Purkinje cells. This supports that directed correction could have a major impact on human disease characteristics.

SCA1 mice show progressive neurodegenerative disease similar to SCA1 patients. In recent work using an inducible mouse model of SCA1, reversal of disease phenotypes was more difficult as the disease progressed, suggesting that earlier treatments will be more beneficial (Zu 2004). In the inducible SCA1 model, inhibition of mutant ataxin-1 expression at week 12 led to rotarod performance improvements.

The intranuclear, ataxin-1 inclusions are characteristic of SCA1 patient brain tissue and SCA1 mice cerebellar Purkinje cells (Burright 1995). The inventors found complete resolution of inclusions in transduced cells, which correlated with improved neuropathology. In the inducible SCA1 model, inclusions resolved several days after inhibition of mutant allele expression. AAV1 expressed shRNAs reduced mutant ataxin-1 expression as early as one week after introduction of vector, indicating that shSCA1-mediated inhibition of ataxin-1 (Q82) expression could improve disease-associated neuropathological changes almost immediately after gene transfer.

In the inventors' initial in vitro screen, it was difficult to identify effective shRNAs for ataxin-1 silencing. The two functional shRNAs discovered by the inventors flanked the CAG repeat region. The generalizability of this finding was tested in studies targeting a mutant huntingtin and found that the CAG-repeat expansion in huntingtin did not confer accessibility to RNAi. Interestingly, shRNAs shSca1.F10 and shSCA.F11 adhere less well to the model criteria (Reynolds 2004) than those that did not reduce ataxin-1 expression. This suggests the potential requirement for screening many hairpins (perhaps up to 20) prior to identifying one suitably potent for gene silencing.

Heterozygous SCA1 mice provide a tool for allele-specific silencing of the disease gene; SCA1 mice retain two wildtype ataxin-1 genes in addition to the human disease transgene. In SCA1 patients, however, shSCA1 would target both the disease and the wildtype allele. For SCA1 this may not be problematic because ataxin-1 knock out mice do not display cerebellar or brainstem pathology and have only mild ataxia measured by rotarod performance. Moreover, shRNAs probably do not reduce mRNA and protein levels to zero. The significant but non-ablative reduction of ataxin-1 would enable cellular machinery to 'catch up' with existent inclusions.

In summary, the inventors have shown that RNAi therapy can dramatically improve cellular and behavioral characteristics in a mouse model of a human dominant neurodegenerative disease, SCA1. The present findings have relevance to other polyglutamine-repeat disorders including Huntington's disease, and neurodegenerative disorders such as Alzheimer's disease, where inhibiting expression of a disease-linked protein would directly protect, or even reverse, disease phenotypes.

EXAMPLE 4

Huntington's Disease (HD)

Huntington's disease (HD) is one of several dominant neurodegenerative diseases that result from a similar toxic gain of function mutation in the disease protein: expansion of a polyglutamine (polyQ)-encoding tract. It is well established that for HD and other polyglutamine diseases, the length of the expansion correlates inversely with age of disease onset. Animal models for HD have provided important clues as to how mutant huntingtin (htt) induces pathogenesis. Currently, no neuroprotective treatment exists for HD. RNA interference has emerged as a leading candidate approach to reduce expression of disease genes by targeting the encoding mRNA for degradation.

As discussed in Example 3 above, short hairpin RNAs (shRNAs) were generated that significantly inhibited human htt expression in cell lines. Importantly, the shRNAs were designed to target sequences present in HD transgenic mouse models. The present studies test the efficacy of the shRNAs in HD mouse models by determining if inclusions and other pathological and behavioral characteristics that are representative of HD can be inhibited or reversed. In a transgenic model of inducible HD, pathology and behavior improved when mutant gene expression was turned off. These experiments show that RNAi can prevent or reverse disease.

Although the effect of partial reduction of wildtype htt in adult neurons is unknown, it is advantageous to target only mutant htt for degradation, if possible. One polymorphism in linkage disequilibrium with HD has been identified in the coding sequence for htt, and others are currently being investigated. Disease allele-specific RNAi are designed using approaches that led to allele specific silencing for other neurogenetic disease models. This would allow directed silencing of the mutant, disease-causing expanded allele, leaving the normal allele intact.

Constitutive expression of shRNA can prevent the neuropathological and behavioral phenotypes in a mouse model of Spinocerebellar Ataxia type I, a related polyQ disease. However, the constitutive expression of shRNA may not be necessary, particularly for pathologies that take many years to develop but may be cleared in a few weeks or months. For this reason, and to reduce long-term effects that may arise if nonspecific silencing or activation of interferon responses is noted, controlled expression may be very important. In order to regulate RNAi for disease application, doxycycline-responsive vectors have been developed for controlled silencing in vitro.

HD researchers benefit from a wealth of animal models including six transgenic and four knock-in mouse models (Bates 2003). Expression is from the endogenous human promoter, and the CAG expansion in the R6 lines ranges from 110 to approximately 150 CAGs. The R6/2 line is the most extensively studied line from this work. R6/2 mice show aggressive degenerative disease, with age of symptom onset at 8-12 weeks, and death occurring at 10 to 13 weeks. Neuronal intranuclear inclusions, a hallmark of HD patient brain, appear in the striatum and cortex of the R6/2 mouse (Meade 2002).

Adding two additional exons to the transgene and restricting expression via the prion promoter led to an HD mouse model displaying important HD characteristics but with less aggressive disease progression (Shilling 1999, Shilling 2001). The Borchelt model, N171-82Q, has greater than wild-type levels of RNA, but reduced amounts of mutant protein relative to endogenous htt. N171-82Q mice show normal development for the first 1-2 months, followed by failure to gain weight, progressive incoordination, hypokinesis and tremors. There are statistically significant differences in the rotarod test, alterations in gait, and hindlimb clasping. Mice show neuritic pathology characteristic of human HD. Unlike the Bates model, there is limited neuronal loss.

Detloff and colleagues created a mouse knock-in model with an extension of the endogenous mouse CAG repeat to approximately 150 CAGs. This model, the CHL2 line, shows more aggressive phenotypes than prior mouse knock-in models containing few repeats (Lin 2001). Measurable neurological deficits include clasping, gait abnormalities, nuclear inclusions and astrogliosis.

The present studies utilize the well-characterized Borchelt mouse model (N171-82Q, line 81), and the Detloff knock-in model, the CHL2 line. The initial targets for htt silencing were focused on sequences present in the N171-82Q transgene (exons 1-3). The use of this model was advantageous in the preliminary shRNA development because the RNAi search could focus on only the amino-terminal encoding sequences rather than the full length 14 kb mRNA. FIG. 12 depicts the one-step cloning approach used to screen hairpins (Harper 2004). No effective shRNAs were found in exon 1, but several designed against exon 2, denoted shHDEx2.1 (5'-AAGAAAGAACTTTCAGCTACC-3', SEQ ID NO:7), shHDEx2.2 19 nt (5'-AGAACTTTCAGCTACCAAG-3' (SEQ ID NO:8)), or shHDEx2.2 21 nt 5'-AAA-GAACTTTCAGCTACCAAG-3' (SEQ ID NO:9)) and exon 3 (shHDEx3.1 19 nt 5'-TGCCTCAACAAAGTTATCA-3' (SEQ ID NO:10) or shHDEx3.1 21 nt 5'-AATGCCTCAA-CAAAGTTATCA-3' (SEQ ID NO:11)) sequences were effective. In co-transfection experiments with shRNA expressing plasmids and the N171-82Q transcript target, shHDEx2.1 reduced N171-Q82 transcript levels by 80%, and protein expression by 60%.

In transient transfection assays shHDex2.1 did not silence a construct spanning exons 1-3 of mouse htt containing a 79 CAG repeat expansion, the mouse equivalent of N171-82Q. Next shHDEx2 into NIH 3T3 cells were transfected to confirm that endogenous mouse htt, which is expressed in NIH 3T3 cells, would not be reduced. Surprisingly, shHDEx2.1 and shHDEx3.1 silenced full-length mouse htt. In contrast, shHDEx2.2 silenced only the human N171-82Q transgene.

Yamamoto and colleagues and others have demonstrated that preformed inclusions can resolve (Yamamoto 2000). To test if RNAi could also reduce preformed aggregates, the inventors used a neuronal cell line, which, upon induction of Q80-eGFP expression, showed robust inclusion formation (Xia 2002). Cells laden with aggregates were mock-transduced, or transduced with recombinant virus expressing control shRNA, or shRNAs directed against GFP. The inventors found dramatic reduction in aggregates as assessed by fluorescence. Quantification showed dose dependent effects (FIG. 13) that were corroborated by western blot (Xia 2002).

As indicated in Example 1 above, viral vectors expressing siRNAs can mediate gene silencing in the CNS (Xia 2002). Also, as indicated in Example 3 above, these studies were extended to the mouse model of spinocerebellar ataxia type 1 (SCA1). The data are important as they demonstrate that shRNA is efficacious in the CNS of a mouse model of human neurodegenerative disease. The data also support that shRNA expression in brain is not detrimental to neuronal survival.

shRNAs can target the Exon 58 polymorphism. As described in Example 2 above, a polymorphism in htt exon 58 is in linkage disequilibrium with HD (Ambrose 1994). Thirty eight percent of the HD population possesses a 3-GAG repeat in exon 58, in contrast to the 4-GAG repeat found in 92% of non-HD patients. The polymorphism likely has no affect on htt, but it provides a target for directing gene silencing to the disease allele. As indicated in Example 2 above, in experiments to test if allele-specific silencing for HD was possible, plasmids were generated that expressed shRNAs that were specific for the exon 58 polymorphism. The exon 58 3-GAG-targeting shRNAs were functional.

Developing vectors for control of RNAi in vivo. As demonstrated above, shRNA expressed from viral vectors is effective at directing gene silencing in brain. Also, viral vectors expressing shSCA1 inhibited neurodegeneration in the SCA1 mouse model. ShRNA expression was constitutive in both instances. However, constitutive expression may not be necessary, and could exacerbate any noted nonspecific effects. The present inventors have developed and tested several doxycycline-regulated constructs. The construct depicted in FIG. 14 showed strong suppression of target gene (GFP) expression after addition of doxycycline and RNAi induction.

RNAi can Protect, and/or Reverse, the Neuropathology in Mouse Models of Human Huntington's Disease Two distinct but complimentary mouse models are used, the N171-82Q transgenic and CHL2 knock-in mice. The former express a truncated NH2-terminal fragment of human htt comprising exons 1-3 with an 82Q-repeat expansion. The knock-in expresses a mutant mouse allele with a repeat size of ~150. Neither shows significant striatal or cortical cell loss. Both therefore are suitable models for the early stages of HD. They also possess similarities in mid- and end-stage neuropathological phenotypes including inclusions, gliosis, and motor and behavioral deficits that will permit comparison and validation. On the other hand, the differences inherent in the two models provide unique opportunities for addressing distinct questions regarding RNAi therapy. For example, N171-82Q transgenic mice have relatively early disease onset. Thus efficacy can be assessed within a few months, in contrast to 9 months or more in the CHL2 line. Because the data showed that shHDEx2.2 targets the human transgene and not mouse HD, evaluate disease-allele specific silencing in N171-82Q mice is evaluated. In contrast, the CHL2 knock-in is important for testing how reducing expression of both the mutant and wildtype alleles impacts on the HD phenotype. Finally, both models should be investigated because any therapy for HD should be validated in two relevant disease models.

siRNA Against Human htt Protects Against Inclusion Formation in N171-82Q Mice

The data show that it is possible to silence the human N171-82Q transgene in vitro, and work in reporter mice and SCA1 mouse models demonstrated efficacy of RNAi in vivo in brain. shHDEx2.2 constructs, expressed from two vector systems with well-established efficacy profiles in CNS, are now tested for their capacity to reduce mutant transgenic allele expression in vivo. Further, the impact of shHDEx2.2 on inclusion formation is assessed. Inclusions may not be pathogenic themselves, but they are an important hallmark of HD and their presence and abundance correlates with severity of disease in many studies.

Recombinant feline immunodeficiency virus (FIV) and adeno-associated virus (AAV) expressing shHDs are injected into N171-82Q. The levels of shHDs expressed from FIV and AAV are evaluated, as is the ability to reduce htt mRNA and protein levels in brain, and subsequently affect inclusion formation.

Mice. N171-82Q mice developed by Borchelt and colleagues are used for these experiments (Shilling 1999, Shilling 2001). The colony was set up from breeders purchased from Jackson Laboratories (N171-82Q, line 81) and are maintained as described (Shilling 1999, Shilling 2001). F1 pups are genotyped by PCR off tail DNA, obtained when tagging weaned litters.

IC2 and EM48 have been used previously to evaluate N171-82Q transgene expression levels in brain by immunohistochemistry (IHC) and western blot (Zhou 2003, Trottier 1995). EM48 is an antibody raised against a GST-NH2 terminal fragment of htt that detects both ubiquitinated and non-ubiquitinated htt-aggregates (Li 2000), and the IC2 antibody recognizes long polyglutamine tracts (Trottier 1995). By 4 weeks N171-82Q mice show diffuse EM48-positive staining in striata, hippocampus, cerebellar granule cells, and cortical layers IV and V (Shilling 1999, Shilling 2001). The present experiments focus on the striatum and cortex because they are the major sites of pathology in human HD. TUNEL positivity and GFAP immunoreactivity are also significant in striatal sections harvested from 3 month old N171-82Q mice (Yu 2003). At 4 months, punctate nuclear and cytoplasmic immunoreactivity is also seen (Yu 2003).

Viruses. It is difficult to directly compare the two viruses under study at equivalent doses; FIV is enveloped and can be concentrated and purified, at best, to titers of $5 \times 10^8$ infectious units/ml (iu/ml). FIV pseudotyped with the vesicular stomatitus glycoprotein (VSVg) are used because of its tropism for neurons in the striatum (Brooks 2002). In contrast, AAV is encapsidated and can be concentrated and purified to titers ranging from $1 \times 10^9$ to $1 \times 10^{11}$ iu/ml, with $1 \times 10^{10}$ titers on average. AAV serotype 5 is used because it is tropic for neurons in striatum and cortex, our target brain regions. Also, it diffuses widely from the injection site (Alisky 2000, Davidson 2000). Ten-fold dilutions of FIV and AAV generally results in a greater than 10-fold drop in transduction efficiency, making comparisons at equal titers, and dose escalation studies, unreasonable. Thus, both viruses are tested at the highest titers routinely available to get a fair assessment of their capacities for efficacy in N171-82Q mice. All viruses express the humanized *Renilla reniformis* green fluorescent protein (hrGFP) reporter transgene in addition to the shRNA sequence (FIG. 15). This provides the unique opportunity to look at individual, transduced cells, and to compare pathological improvements in transduced vs. untransduced cells.

Injections. Mice are placed into a David Kopf frame for injections. Mice are injected into the striatum (5 microliters; 100 nl/min) and the cortex (3 microliters; 75 nl/min) using a Hamilton syringe and programmable Harvard pump. The somatosensory cortex is targeted from a burr hole at −1.5 mm from Bregma, and 1.5 mm lateral. Depth is 0.5 mm. The striatum is targeted through a separate burr hole at +1.1 mm from Bregma, 1.5 mm lateral and 2 mm deep. Only the right side of the brain is injected, allowing the left hemisphere to be used as a control for transgene expression levels and presence or absence of inclusions.

Briefly, groups of 4 week-old mice heterozygous for the N171-82Q transgene and their age-matched wildtype littermates are injected with FIV (FIV groups are VSVg.FIV.shHDEx2.2, VSVg.FIVshlacZ, VSVg.hrGFP, saline) or AAV (AAV groups are AAV5.shHDEx2.2, AAV5shlacZ, AAV5hrGFP, saline) (n=18/group; staggered injections because of the size of the experiment). [Names of shHDEx2.2 and shlacZ expressing viruses have been shortened from shlacZ.hrGFP, for example, to make it easier to read—but all vectors express hrGFP as reporter.] Nine mice/group are sacrificed at 12 weeks of age to assess the extent of transduction (eGFP fluorescence; viral copy number/brain region), shRNA expression (northern for shRNAs, and inhibition of expression of the transgenic allele (QPCR and western blot). The remaining groups are sacrificed at 5 months of age. This experimental set up is repeated (to n=6/group) to confirm results and test inter-experiment variability.

All mice in all groups are weighed bi-weekly (every other week) after initial weekly measurements. N171-82Q mice show normal weight gain up to approximately 6 weeks, after which there are significant differences with their wildtype littermates.

PCR Analyses. Brains are harvested from mice sacrificed at 12 weeks of age, and grossly evaluated for GFP expression to confirm transduction. The cortex and striatum from each hemisphere is dissected separately, snap frozen in liquid N2, pulverized with a mortar and pestle, and resuspended in Trizol (Gibco BRL). Separate aliquots are used for Q-RTPCR for N171-82Q transgenes and DNA PCR for viral genomes. A coefficient of correlation is determined for transgene silencing relative to viral genomes for both vector systems, for the regions analyzed and compared to contralateral striata and mice injected with control vectors or saline.

The RNA harvested is used to evaluate activation of interferon-responsive genes. Bridges et al (Bridges 2003) and Sledz and colleagues (Sledz 2003) found activation of 2'5' oligo(A) polymerase (OAS) in cell culture with siRNAs and shRNAs, the latter expressed from lentivirus vectors. Gene expression changes are assessed using QPCR for OAS, Stat1, interferon-inducible transmembrane proteins 1 and 2 and protein kinase R (PKR). PKR activation is an initial trigger of the signaling cascade of the interferon response.

Protein analyses. A second set of 3 brains/group are harvested for protein analysis. Regions of brains are micro dissected as described above, and after pulverization are resuspended in extraction buffer (50 mM Tris, pH 8.0, 150 mM NaCl, 1% NP-40, 0.5% deoxycholate, 0.1% SDS, 1 mM BetaME, 1× complete protease inhibitor cocktail) for analysis by western blot. HrGFP expression are evaluated and correlated to diminished levels of soluble N171-82Q using anti-GFP and antibodies to the NH2-terminal region of htt (EM48) or the polyglutamine tract (IC2).

Histology. Histology is done on the remaining animals. Mice are perfused with 2% paraformaldehyde in PBS, brains blocked to remove the cerebellum, post-fixed ON, and then cryoprotected in 30% sucrose. Full coronal sections (40 µm) of the entire cerebrum are obtained using a Microtome (American Products Co #860 equipped with a Super Histo Freeze freezing stage). Briefly, every section is collected, and sections 1-6 are placed into 6 successive wells of a 24-well plate. Every 400 microns, two sections each of 10 microns are collected for Nissl and H&E staining. The process is repeated.

EM-48 immuno-staining reveals diffuse nuclear accumulations in N171-82Q mice as early as 4 weeks of age. In 6 mo. old mice inclusions are extensive (Shilling 2001). The increase in cytoplasmic and nuclear EM48 immuno-reactivity, and in EM48 immuno-reactive inclusions over time allow quantitative comparisons between transduced and untransduced cells. Again, control values are obtained from mice injected with shlacZ-expressing vectors, saline injected mice, and wt mice. The contralateral region is used as another control, with care taken to keep in mind the possibility of retrograde and anterograde transport of virus from the injection site.

Quantitation of nuclear inclusions is done using BioQuant™ software in conjunction with a Leitz DM RBE upright microscope equipped with a motorized stage (Applied Scientific Instruments). Briefly, floating sections are stained with anti-NeuN (AMCA secondary) and EM48 antibodies (rhodamine secondary) followed by mounting onto slides. The regions to be analyzed are outlined, and threshold levels for EM48 immunoreactivity set using sections from control injected mice. A minimum of 50 hrGFP-positive and hrGFP negative neurons cells are evaluated per slide (5 slides/mouse), and inclusion intensity measured (arbitrary units). This is done for both striata and cortices. To quantitate cytoplasmic inclusions, the striatum is outlined and total EM48 aggregate density measured. Threshold values are again done using control hemispheres and control injected mice.

Additional wells of sections are stained with anti-GFAP, anti-neurofilament, and the lectin GSA to assay for viral or viral+hairpin induced gliosis, neuritic changes, and microglial activation, respectively. GFAP-stained brain sections from N171-82Q mice show gliosis by 4 months (Yu 1998), although earlier time points have not been reported.

Stereology. In a separate experiment on N171-82Q mice and wt mice, unbiased stereology using BioQuant™ software is done to assess transduction efficiency. Stereology allows for an unbiased assessment of efficiency of transduction (number of cells transduced/input). AAV5 (AAV5hrGFP, AAV5shHD.hrGFP) and FIV (VSVg.FIVhrGFP, VSVg.FIVshHD.hrGFP) transduction efficiency is compared in the striatum and somatosensory cortex in HD and wildtype mice, with n=5 each. Mice are harvested at 12 and 20 weeks. The cerebrum is sectioned in its entirety and stored at −20° C. until analysis. Briefly, six weeks after gene transfer with VSVg.FIVhrGFP (n=3) or AAV5hrGFP (n=3), every section of an HD mouse cerebrum is mounted and an initial assessment of the required numbers of sections and grid and dissector size done using the coefficient of error (as determined by Martheron's quadratic approximation formula) as a guide.

The 171-82Q HD mouse model has important neuropathological and behavioral characteristics relevant to HD. Onset of disease occurs earlier than HD knock-in or YAC transgenic models, allowing an initial, important assessment of the protective effects of RNAi on the development of neuropathology and dysfunctional behavior, without incurring extensive long term housing costs. Admittedly, disease onset is slower and less aggressive than the R6/2 mice created by Bates and colleagues (Mangiarini 1996), but the R6/2 line is difficult to maintain and disease is so severe that it may be less applicable and less predicative of efficacy in clinical trials.

N171-82Q mice (n=6/group) and age-matched littermates (n=6/group) are be weighed twice a month from 4 wks on, and baseline rotarod tests performed at 5 and 7 weeks of age. Numbers of mice per group are as described in Schilling et al (Shilling 1999) in which statistically significant differences between N171-82Q and wildtype littermates were described. At 7 weeks of age (after testing is complete), AAV (AAVshHDEx2.2, AAVshlacZ, AAVhrGFP, saline) or FIV (FIVshEx2.2, FIVshlacZ, FIVhrGFP, saline) is injected bilaterally into the striatum and cortex. Rotarod tests are repeated at 3-week intervals starting at age 9 weeks, until sacrifice at 6 months. The clasping behavior is assessed monthly starting at 3 months.

Behavioral testing. N171-82Q mice are given four behavioral tests, all of which are standard assays for progressive disease in HD mouse models. The tests allow comparisons of behavioral changes resulting from RNAi to those incurred in HD mouse models given other experimental therapies. For example, HD mice given cystamine or creatine therapy showed delayed impairments in rotarod performance, and in some cases delayed weight loss (Ferrante 2000, Dedeoglu 2002, Dedeogu 2003) In addition to the rotarod, which is used to assay for motor performance and general neurological dysfunction, the activity monitor allows assessment of the documented progressive hypoactivity in N171-82Q mice. The beam analysis is a second test of motor performance that has also been used in HD mice models (Carter 1999). Clasping, a phenotype of generalized neurological dysfunction, is straightforward and takes little time. Clasping phenotypes were corrected in R. Hen's transgenic mice possessing an inducible mutant htt.

Accelerated rotarod. N171-82Q and age-matched littermates are habituated to the rotarod at week 4, and 4 trials per day for 4 days done on week 5 and 7, and every 3 weeks hence using previously described assays (Shilling 1999, Clark 1997) in use in the lab. Briefly, 10 min trials are run on an Economex rotarod (Columbus Instruments) set to accelerate from 4 to 40 rpm over the course of the assay. Latency to fall is recorded and averages/group determined and plotted. Based on prior work (Shilling 1999) 6 mice will give sufficient power to assess significance.

Clasping behavior. Normal mice splay their limbs when suspended, but mice with neurological deficits can exhibit the opposite, with fore and hind limbs crunched into the abdomen (clasping). All mice are suspended and scored for clasping monthly. The clasp must be maintained for at least 30 sec. to be scored positive.

Activity monitor. Most HD models demonstrate hypokinetic behavior, particularly later in the disease process. This can be measured in several ways. One of the simplest methods is to monitor home cage activity with an infrared sensor (AB-system 4.0, Neurosci Co., LTD). Measurements are taken over 3 days with one day prior habituation to the testing cage (standard 12-hour light/dark cycle). Activity monitoring is done at 12, 17, and 20 and 23 weeks of age.

Beam walking. N171Q-82Q and age matched littermates are assayed for motor performance and coordination using a series of successively more difficult beams en route to an enclosed safety platform. The assay is as described by Carter et al (Carter 1999). Briefly, 1 meter-length beams of 28, 17 or 11 mm diameter are placed 50 cm above the bench surface. A support stand and the enclosed goal box flank the ends. Mice are trained on the 11 mm beam at 6 weeks of age over 4 days, with 3 trials per day. If mice can traverse the beam in <20 sec. trials are initiated. A trial is then run on each beam, largest to smallest, with a 60 sec cutoff/beam and one minute rest between beams. A second trial is run and the mean scores of the two trials evaluated.

RNAi cannot replace neurons; it only has the potential to protect non-diseased neurons, or inhibit further progression of disease at a point prior to cell death. N171-82Q mice do not show noticeable cellular loss, and is therefore an excellent model of early HD in humans. The general methodology is the similar to that described above, except that the viruses are injected at 4 months, when N171-82Q mice have measurable behavioral dysfunction and inclusions. Animals are sacrificed at end stage disease or at 8 months, whichever comes first. Histology, RNA and protein in harvested brains are analyzed as described above.

It is important to confirm the biological effects of virally expressed shHDs in a second mouse model, as it is with any therapy. The Detloff knock-in mouse (the CHL2 line, also notated as HdhCAGQ150) is used as a second model of early HD disease phenotypes. These mice have a CAG expansion of approximately 150 units, causing brain pathologies similar to HD including gliosis and neural inclusions in the cortex and striatum. They also show progressive motor dysfunction and other behavioral manifestations including rotarod deficits, clasping, gait abnormalities and hypoactivity.

Heterozygous CHL2 mice express the mutant and wildtype allele at roughly equivalent levels, and shRNAs directed against mouse HD silence both transcripts. shmHDEx2.1 causes reductions in gene expression, but not complete silencing. Disease severity in mouse models is dependent on mutant htt levels and CAG repeat length.

The inventors created shmHDEx2 (shRNA for murine HD) directed against a region in mouse exon 2 that reduces expression of the full-length mouse Hdh transcript in vitro. Transduction of neurons with shmHDEx2-expressing viruses, and its impacts on neuropathological progression, behavioral dysfunction and the appearance of EM48 immuno-reactive inclusions in CHL2 mice is tested. shmHD- or shlacZ-expressing vectors in CHL2 and wildtype brain is tested. In this experiment, virus is injected into the striatum of wt or CHL2 mice (10/group) using the coordinates described above, at 3 months of age. Two months later mice are sacrificed and brains removed and processed for RNA (n=5/group) and protein (n=5).

A second study tests the vectors in the Detloff model. Briefly, 15 mice per group are injected into the striatum and cortex at 3 months of age with AAV (AAVshmHD, AAVshlacZ, AAVhrGFP, saline) or FIV (VSVg.FIV.shmHD, VSVg.FIVshlacZ, VSVg.FIVhrGFP, saline) expressing the transgenes indicated. To assess the impact of RNAi, activity performed. The mice are sacrificed at 16-18 months of age and five brains/group are processed for histology and sections banked in 24-well tissue culture plates. The remaining brains are processed for RNA (n=6) and protein analysis (n=5). Northern blots or western blots are required to analyze wildtype and mutant htt expression because the only distinguishing characteristic is size.

Development of Effective Allele-Specific siRNAs

Mutant htt leads to a toxic gain of function, and inhibiting expression of the mutant allele has a profound impact on disease (Yamamoto 2000). Also, selectively targeting the disease allele would be desirable if non-disease allele silencing is deleterious. At the present time, there is one documented disease linked polymorphism in exon 58 (Lin 2001). Most non-HD individuals have 4 GAGs in Hdh exon 58 while 38% of HD patients have 3 GAGs. As described above, RNAi can be accomplished against the 3-GAG repeat.

Prior work by the inventors showed the importance of using full-length targets for testing putative shRNAs. In some cases, shRNAs would work against truncated, but not full-length targets, or vice-versa. Thus, it is imperative that testable, full-length constructs are made to confirm allele-specific silencing. The V5 and FLAG tags provide epitopes to evaluate silencing at the mRNA and protein levels. This is important as putative shRNAs may behave as miRNAs, leading to inhibition of expression but not message degradation.

Designing the siRNAs. Methods are known for designing siRNAs (Miller 2003, Gonzalez-Alegre 2003, Xia 2002, Kao 2003). Information is also know about the importance of maintaining flexibility at the 5' end of the antisense strand for loading of the appropriate antisense sequence into the RISC complex (Khvorova 2003 Schwarz 2003). DNA sequences are generated by PCR. This method allows the rapid generation of many candidate shRNAs, and it is significantly cheaper than buying shRNAs. Also, the inserts can be cloned readily into our vector shuttle plasmids for generation of virus. The reverse primer is a long oligonucleotide encoding the antisense sequence, the loop, the sense sequence, and a portion of the human U6 promoter. The forward primer is specific to the template in the PCR reaction. PCR products are cloned directly into pTOPO blunt from InVitrogen, plasmids transformed into DH5a, and bacteria plated onto Kan$^r$ plates (the PCR template is Amp$^r$). Kan$^r$ clones are picked and sequenced. Sequencing is done with an extended 'hot start' to allow effective read-through of the hairpin. Correct clones are transfected into cells along with plasmids expressing the target or control sequence (HttEx58.GAG3V5 and HttEx58.GAG4FLAG, respectively) and silencing evaluated by western blot. Reductions in target mRNA levels are assayed by Q-RTPCR. The control for western loading is neomycin phosphotransferase or hrGFP, which are expressed in the target-containing plasmids and provide excellent internal controls for transfection efficiency. The control for Q-RT-PCR is HPRT.

Cell lines expressing targets with the identified polymorphism or control wildtype sequences are created. Target gene expression are under control of an inducible promoter. PC6-3, Tet repressor (TetR+) cells, a PC-12 derivative with a uniform neuronal phenotype (Xia 2002) are used. PC6-3 cells are transfected with plasmids expressing HDEx58.GAG3V5 (contains neo marker) and HDEx58GAG4FLG (contains puro marker), and G418+/puromycin+ positive clones selected and characterized for transcript levels and htt-V5 or htt-Flag protein levels.

FIV vectors expressing the allele specific shRNAs are generated and used to test silencing in the inducible cell lines. FIV vectors infect most epithelial and neuronal cell lines with high efficiency and are therefore useful for this purpose. They also efficiently infect PC6-3 cells. AAV vectors are currently less effective in in vitro screening because of poor transduction efficiency in many cultured cell lines.

Cells are transduced with 1 to 50 infectious units/cell in 24-well dishes, 3 days after induction of mutant gene expression. Cells are harvested 72 h after infection and the effects on HDEx58.GAG3V5 or HDEx58GAG4FLG expression monitored.

EXAMPLE 5

Micro RNAi-Therapy for Polyglutamine Disease

Post-transcriptional gene silencing occurs when double stranded RNA (dsRNA) is introduced or naturally expressed in cells. RNA interference (RNAi) has been described in plants (quelling), nematodes, and *Drosophila*. This process serves at least two roles, one as an innate defense mechanism, and another developmental (Waterhouse 2001 Fire 1999, Lau 2001, Lagos-Quintana 2001, Lee 2001). RNAi may regulate developmental expression of genes via the processing of small, temporally expressed RNAs, also called microRNAs (Knight 2001, Grishok 2001). Harnessing a cell's ability to respond specifically to small dsRNAs for target mRNA degradation has been a major advance, allowing rapid evaluation of gene function (Gonczy 2000, Fire 1998, Kennerdell 1998, Hannon 2002, Shi 2003, Sui 2002).

Most eukaryotes encode a substantial number of small noncoding RNAs termed micro RNAs (miRNAs) (Zeng 2003, Tijsterman 2004, Lee 2004, Pham 2004). mir-30 is a 22-nucleotide human miRNA that can be naturally processed from a longer transcript bearing the proposed miR-30 stem-loop precursor. mir-30 can translationally inhibit an mRNA-bearing artificial target sites. The mir-30 precursor stem can be substituted with a heterologous stem, which can be processed to yield novel miRNAs and can block the expression of endogenous mRNAs.

Huntington's disease (HD) and Spinocerebellar ataxia type I (SCA1) are two of a class of dominant, neurodegenerative diseases caused by a polyglutamine (polyQ) expansion. The mutation confers a toxic gain of function to the protein, with polyQ length predictive of age of onset and disease severity. There is no curative or preventative therapy for HD or SCA1, supporting the investigation of novel strategies. As described above, the inventors showed that gene silencing by RNA interference (RNAi) can be achieved in vitro and in vivo by expressing short hairpin RNAs (shRNAs) specific for mRNAs encoding ataxin-1 or huntingtin. Currently, strong, constitutive polIII promoters (U6 and Hp are used to express shRNAs, which are subsequently processed into functional small interfering RNAs (siRNAs). However, strong, constitutive expression of shRNAs may be inappropriate for diseases that take several decades to manifest. Moreover, high-level expression may be unnecessary for sustained benefit, and in some systems may induce a non-specific interferon response leading to global shut-down of gene expression. The inventors therefore generated polII-expressed microRNAs (miRNAs) as siRNA shuttles as an alternative strategy. Due to their endogenous nature, miRNA backbones may prevent the induction of the interferon response.

Using human mir-30 as a template, miRNA shuttles were designed that upon processing by dicer released siRNAs specific for ataxin-1. Briefly, the constructs were made by cloning a promoter (such as an inducible promoter) and an miRNA shuttle containing an embedded siRNA specific for a target sequence (such as ataxin-1) into a viral vector. By cloning the construct into a viral vector, the construct can be effectively introduced in vivo using the methods described in the Examples above. Constructs containing polII-expressed miRNA shuttles with embedded ataxin-1-specific siRNAs were co-transfected into cells with GFP-tagged ataxin-1, and gene silencing was assessed by fluorescence microscopy and western analysis. Dramatic arid dose-dependent gene silencing relative to non-specific miRNAs carrying control siRNAs was observed. This polII-based expression system exploits the structure of known miRNAs and supports tissue-specific as well as inducible siRNA expression, and thus, serves as a unique and powerful alternative to dominant neurodegenerative disease therapy by RNAi.

Briefly, the constructs were made by cloning a promoter (such as an inducible promoter) and an miRNA shuttle containing an embedded siRNA specific for a target sequence (such as ataxin-1) into a viral vector. By cloning the construct into a viral vector, the construct can be effectively introduced in vivo using the methods described in the Examples above.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

Citations

Adelman et al., *DNA*, 2, 183 (1983).
Alisky et al., *Hum Gen Ther*, 11, 2315 (2000b).
Alisky et al., *NeuroReport*, 11, 2669 (2000a).
Ambrose et al, Somat Cell Mol Genet. 20, 27-38 (1994)
Anderson et al., *Gene Ther.*, 7(12), 1034-8 (2000).
Bass, *Nature*, 411, 428 (2001).
Bates et al., Curr Opin Neurol 16:465-470, 2003.
Bernstein et al., *Nature*, 409, 363 (2001).
Bledsoe et al., *NatBiot*, 18, 964 (2000).
Brantl, *Biochemica and Biophysica Acta,* 1575, 15 (2002).
Bridge et al., Nat Genet 34:263-264, 2003.
Brooks et al., *Proc. Natl. Acad. Sci. U.S.A.,* 99, 6216 (2002).
Brummelkamp, T. R. et al., *Science* 296:550-553 (2002).
Burright, E. N. et al., Cell, 82, 937-948 (1995)
Caplan et al., *Proc. Natl. Acad. Sci. U.S.A.,* 98, 9742 (2001).
Caplen et al., *Hum. Mol. Genet.,* 11(2), 175-84 (2002).
Carter et al., J Neurosci 19:3248, 1999.
Chai et al., *Hum. Mol. Genet.,* 8, 673-682 (1999b).
Chai et al., *J. Neurosci.,* 19, 10338 (1999).
Chen, H. K. et al., Cell, 113, 457-68 (2003)
Clark, H. B. et al., J. Neurosci., 17(19), 7385-7395 (1997)
Cummings, C. J. et al., Nat. Genet., 19(2), 148-154 (1998)
Davidson, B. L. et al., The Lancet Neurol., 3, 145-149 (2004)
Davidson et al., PNAS USA 97(7):3428-3432, 2000.
Davidson et al., Nat Rev Neurosci 4:353-364, 2003.
Dedeoglu et al., J Neurochem 85:1359-1367, 2003.
Dedeoglu et al., J Neurosci 22:8942-8950, 2002.
During et al., Gene Ther 5:820-827, 1998.
Elbashir et al, *EMBO J.,* 20(23), 6877-88 (2001c).
Elbashir et al., *Genes and Development,* 15, 188 (2001).
Elbashir et al., *Nature,* 411, 494 (2001).
Emamian, E. S. et al., Neuron, 38, 375-87 (2003)
Felgner et al., *Proc. Natl. Acad. Sci.,* 84, 7413 (1987).
Fernandez-Funez, P. et al., Nature, 408, 101-106 (2000)
Ferrante et al., J Neurosci 20:4389-4397, 2000.
Fire et al., *Nature,* 391(6669), 806-11 (1998).
Fire A. Trends Genet 15(9):358-363, 1999
Frisella et al., Mol Ther 3(3):351-358, 2001.
Gitlin et al., *Nature,* 418(6896), 430-4 (2002).
Gonczy et al., Nature 408:331-336, 2000.
Gonzalez-Alegre et al., Nat Genet 3:219-223, 1993.
Grishok et al., Cell 106:23-34, 2001.
Hamilton and Baulcombe, *Science,* 286, 950 (1999).
Hammond et al., *Nature,* 404, 293 (2000).
Hannon G J. Nature 418:244-251, 2002.
Harper et al., Meth Mol. Biol. In Press 2004.
Jacque et al., *Nature,* 418(6896), 435-8 (2002).
Kang et al., J Virol 76:9378-9388, 2002.
Kao et al., J Biol Chem 2003.
Kawasaki, H., et al., Nucleic Acids Res, 31, 981-7 (2003)
Kennerdell and Carthew, *Cell,* 95, 1017 (1998).
Khvorova, A., et al., Cell, 115, 505 (2003)
Klement, I. A. et al., Cell, 95, 41-53 (1998)
Knight et al., Science 293:2269-2271, 2001.
Kunath et al., Nat Biotechnol 21:559-561, 2003.
Lagos-Quintana et al., Science 294:853-858, 2001.
Lau et al., Science 294:858-862, 2001.
Lee et al., Science 294:862-864, 2001.
Lee, N. S., et al., *Nat. Biotechnol.* 19:500-505 (2002).
Lee et al., Cell, 117, 69-81 (2004)
Li et al., Nat Genet 25:385-389, 2000.
Lin et al., *Hum. Mol. Genet.,* 10(2), 137-44 (2001).
Lotery et al., Hum Gene Ther 13:689-696, 2002.
Mangiarini et al., Cell 87(3):493-506, 1996.
Margolis and Ross, *Trends Mol. Med.,* 7, 479 (2001).
McCaffrey et al., *Nature,* 418(6893), 38-9 (2002).
McManus and Sharp, *Nat. Rev. Genet.* 3(10), 737-47 (2002).
Meade et al., J Comp Neurol 449:241-269, 2002.
Meinkoth and Wahl, *Anal. Biochem.,* 138, 267 (1984).
Miller, V. M. et al., PNAS USA, 100, 7195-200 (2003)
Miyagishi, M. & Taira, K. *Nat. Biotechnol.* 19:497-500 (2002).
Moulder et al., *J. Neurosci.,* 19, 705 (1999).
Needleman and Wunsch, *JMB,* 48, 443 (1970).
Nykanen et al., *Cell,* 107, 309 (2001).
Okabe et al., *FEBS Lett.,* 407, 313 (1997).

Ooboshi et al., *Arterioscler. Thromb. Vasc. Biol.*, 17, 1786 (1997).
Orr et al., Nat. Genet. 4, 221-226 (1993)
Orr et al., Cell 101:1-4, 2000.
Passini et al., J Virol 77:7034-7040, 2003.
Pham et al., Cell, 117:83-94 (2004)
Pittman et al., *J. Neurosci.*, 13(9), 3669-80 (1993).
Plasterk et al., Cell, 117, 1-4 (2004)
Reynolds, A. et al., Nat. Biotechnol., 22, 326-30 (2004)
Rubinson et al., Nat Genet 33:401-406, 2003.
Sambrook and Russell, *Molecular Cloning: A Laboratory Manual*, Cold Spring
Schilling et al., Hum Mol Genet 8(3):397-407, 1999.
Schilling et al., Neurobiol Dis 8:405-418, 2001.
Schwarz et al., *Mol. Cell.*, 10(3), 537-48 (2002).
Schwarz et al., Cell 115:199-208, 2003.
Shi Y, Trends Genet 19:9-12, 2003.
Skinner, P. J. et al., Nature, 389, 971-234 (1997)
Skorupa et al., Exp Neurol 160:17-27, 1999.
Sledz et al., Nat Cell Biol 5:834-839, 2003.
Stein et al., *J. Virol.*, 73, 3424 (1999).
Stein et al., Mol Ther 3(6):850-856, 2001.
Stein et al., *RNA*, 9(2), 187-192 (2003).
Sui et al., PNAS USA 99(8):5515-5520, 2002
Tijssen, *Laboratory Techniques in Biochemistry and Molecular Biology Hybridization with Nucleic Acid Probes*, part I chapter 2 "Overview of principles of hybridization and the strategy of nucleic acid probe assays" Elsevier, N.Y. (1993).
Trottier et al., *Nature*, 378(6555), 403-6 (1995).
Turner et al., *Mol. Biotech.*, 3, 225 (1995).
Tuschl, *Nat. Biotechnol.*, 20, 446-8 (2002).
Urabe, M., et al., Hum. Gene Ther., 13, 1935-1943 (2002)
Waterhouse et al., *Proc. Natl. Acad. Sci. U.S.A.*, 95, 13959 (1998).
Waterhouse et al., Nature 411:834-842, 2001.
Williams, R. W. et al., J. Comp. Neurol., 278, 344-52 (1988)
Xia et al., *Nat. Biotechnol.*, 19, 640 (2001).
Xia et al., *Nat. Biotechnol.*, 20(10), 1006-10 (2002).
Xiao et al., Exp Neurol 144:113-124, 1997.
Yamamoto et al., *Cell*, 101(1), 57-66 (2000).
Yu et al., Proc. Natl. Acad. Sci., 99, 6047-6052 (2002).
Yu et al., J Neurosci 23:2193-2202, 2003.
Zamore et al., *Cell*, 101, 25 (2000).
Zeng et al., *RNA*, 9:112-123 (2003)
Zhou et al., J Cell Biol 163:109-118, 2003.
Zoghbi and Orr, *Annu. Rev. Neurosci.*, 23, 217-47 (2000).
Zoghbi et al., Semin Cell Biol., 6, 29-35 (1995)
Zu, T. et al., In Preparation (2004)

---

What is claimed is:

1. An RNA duplex comprising a first strand of RNA and a second strand of RNA, wherein the first strand comprises at least 15 contiguous nucleotides encoded by
   (a) shHDEx2.1 (SEQ ID NO:7),
   (b) shHDEx2.2 19 nt (SEQ ID NO:8),
   (c) shHDEx2.2 21 nt (SEQ ID NO:9),
   (d) shHDEx3.1 19 nt (SEQ ID NO:10), or
   (e) shHDEx3.1 21 nt (SEQ ID NO:11),
   and wherein the second strand is complementary to at least 12 contiguous nucleotides of the first strand.

2. The RNA duplex of claim 1, wherein the duplex is between 15 and 30 base pairs in length.

3. The RNA duplex of claim 1, wherein the first and/or second strand further comprises an overhang region.

4. The RNA duplex of claim 3, wherein the overhang region is from 1 to 10 nucleotides in length.

5. The RNA duplex of claim 1, wherein the first strand and the second strand are operably linked by means of an RNA loop strand to form a hairpin structure comprising a duplex structure and a loop structure.

6. The RNA duplex of claim 5, wherein the loop structure contains from 4 to 10 nucleotides.

7. An expression cassette comprising a nucleic acid encoding at least one strand of the RNA duplex of claim 1.

8. The expression cassette of claim 7, further comprising a promoter.

9. The expression cassette of claim 8, wherein the promoter is a regulatable promoter.

10. The expression cassette of claim 8, wherein the promoter is a constitutive promoter.

11. The expression cassette of claim 8, wherein the promoter is a CMV, RSV, pol II or pol III promoter.

12. The expression cassette of claim 7, wherein the expression cassette further comprises a polyadenylation signal.

13. The expression cassette of claim 7, further comprising a marker gene.

14. A vector comprising the expression cassette of claim 7.

15. A vector comprising two expression cassettes, a first expression cassette comprising a nucleic acid encoding the first strand of the RNA duplex of claim 1 and a second expression cassette comprising a nucleic acid encoding the second strand of the RNA duplex of claim 1.

16. A cell comprising the expression cassette of claim 7.

17. A viral vector comprising a promoter and an miRNA shuttle containing an embedded siRNA that specifically targets a sequence associated with a condition amenable to siRNA therapy, wherein the siRNA comprises an RNA duplex comprising a first strand of RNA and a second strand of RNA, wherein the first strand comprises at least 15 contiguous nucleotides encoded by
 (a) shHDEx2.1 (SEQ ID NO:7),
 (b) shHDEx2.2 19 nt (SEQ ID NO:8),
 (c) shHDEx2.2 21 nt (SEQ ID NO:9),
 (d) shHDEx3.1 19 nt (SEQ ID NO:10), or
 (e) shHDEx3.1 21 nt (SEQ ID NO:11),
 and wherein the second strand is complementary to at least 12 contiguous nucleotides of the first strand.

18. The vector of claim 17, wherein the promoter is an inducible promoter.

19. The vector of claim 17, wherein the vector is an adenoviral, lentiviral, adeno-associated viral (AAV), poliovirus, HSV, or murine Maloney-based viral vector.

20. The vector of claim 17, wherein the vector is an adenoviral viral vector.

21. The vector of claim 20, wherein the condition amenable to siRNA therapy is a neurodegenerative disease.

22. The vector of claim 21, wherein the neurodegenerative disease is a trinucleotide-repeat disease.

23. The vector of claim 22, wherein the trinucleotide-repeat disease is a disease associated with polyglutamine repeats.

24. The vector of claim 23, wherein the trinucleotide-repeat disease is Huntington's disease.

25. The vector of claim 24, wherein the target sequence is a sequence encoding huntingtin.

* * * * *